United States Patent
Roy et al.

(10) Patent No.: US 12,022,832 B2
(45) Date of Patent: Jul. 2, 2024

(54) COMPOUNDS AND METHODS FOR TREATING NEMATODE INFECTIONS

(71) Applicant: The Governing Council of The University of Toronto, Toronto (CA)

(72) Inventors: Peter John Roy, Toronto (CA); Sean Harrington, Toronto (CA); Andrew Burns, Toronto (CA); Jacob Edward Pyche, Peterborough (CA); Genna M. Luciani, Toronto (CA); Jessica Knox, Hamilton (CA); Mark Lautens, Toronto (CA); Ken Loon Choo, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 297 days.

(21) Appl. No.: 17/275,849

(22) PCT Filed: Sep. 10, 2019

(86) PCT No.: PCT/CA2019/051271
§ 371 (c)(1),
(2) Date: Mar. 12, 2021

(87) PCT Pub. No.: WO2020/051689
PCT Pub. Date: Mar. 19, 2020

(65) Prior Publication Data
US 2022/0354117 A1    Nov. 10, 2022

Related U.S. Application Data

(60) Provisional application No. 62/730,286, filed on Sep. 12, 2018.

(51) Int. Cl.
*A01N 43/40*    (2006.01)
*A01N 43/54*    (2006.01)
(Continued)

(52) U.S. Cl.
CPC ............. *A01N 43/40* (2013.01); *A01N 43/54* (2013.01); *A01N 43/60* (2013.01); *A01P 5/00* (2021.08);
(Continued)

(58) Field of Classification Search
None
See application file for complete search history.

(56) References Cited

U.S. PATENT DOCUMENTS

| 9,096,608 B2 | 8/2015 | Eickohoff et al. |
| 9,567,345 B2 | 2/2017 | Eichkoff |

(Continued)

FOREIGN PATENT DOCUMENTS

| EP | 3042645 A1 | 7/2016 |
| JP | 4716672 B2 | 7/2011 |

(Continued)

OTHER PUBLICATIONS

Harrington, Sean et al., Seminar, Characterizing Novel Inhibitors of Neuromuscular Function that May Arrest Worm Infections. (ppt titled: "180518—SH Donnelly Talk—Draft 6", Donnelly Centre for Cellular & Biomolecular Research—2nd Annual Retreat. Niagara-on-the-lake, ON, Canada; May 10, 2018.

(Continued)

*Primary Examiner* — Bethany P Barham
*Assistant Examiner* — Barbara S Frazier
(74) *Attorney, Agent, or Firm* — Bereskin & Parr LLP/S.E.N.C.R.L., s.r.l.; Patricia Folkins

(57) ABSTRACT

The present application relates to the treatment of nematode infections. For example, the application relates to the use of compounds of Formula (III) as defined herein for treatment of a nematode infection or a disease, disorder or condition arising from a nematode infection.

(Continued)

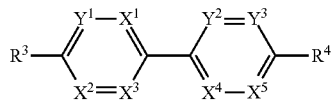

(III)

13 Claims, 9 Drawing Sheets

(51) Int. Cl.
*A01N 43/60* (2006.01)
*A01P 5/00* (2006.01)
*A61K 31/44* (2006.01)
*A61K 31/4418* (2006.01)
*A61K 31/445* (2006.01)
*A61K 31/495* (2006.01)
*A61K 31/505* (2006.01)
*A61P 33/10* (2006.01)

(52) U.S. Cl.
CPC .......... *A61K 31/44* (2013.01); *A61K 31/4418* (2013.01); *A61K 31/445* (2013.01); *A61K 31/495* (2013.01); *A61K 31/505* (2013.01); *A61P 33/10* (2018.01)

(56) References Cited

U.S. PATENT DOCUMENTS

| | | |
|---|---|---|
| 9,714,219 B2 | 7/2017 | Gauvry et al. |
| 2011/0160054 A1 | 6/2011 | Breuningger et al. |
| 2017/0267657 A1 | 3/2017 | Buysse et al. |

FOREIGN PATENT DOCUMENTS

| | | |
|---|---|---|
| JP | 2015131815 A | 7/2015 |
| WO | 20010154507 A1 | 8/2001 |
| WO | 20030088970 A1 | 10/2003 |
| WO | 2019147893 A1 | 8/2019 |

OTHER PUBLICATIONS

Harrington, Sean et al.,Caenorhabditis elegans Satellite Meeting. Mont Tremblant, QC, Canada; Mar. 18-19, 2018 Poster Title: A Pipeline for the Discovery of Novel Neuroactive Small Molecule Tools and Candidate Anthelmintics. (pdf titled: "Sean Harrington—Tremblant Poster—final", (Year: 2018).

Harrington, Sean et al.,Genetics Society of America—2017 C. elegans International Meeting. Los Angeles, CA, USA; Jun. 22-25, 2017 Poster Title: The discovery of neuroactive small molecule tools using a high-throughput egg-laying screening pipeline. (ppt titled: "170615—LA Worm Meeting Poster Draft 1", (Year: 2017).

Harrington, Sean et al.,Donnelly Centre Centre for Cellular & Biomolecular Research Retreat. Muskoka, ON, Canada; May 4, 2017 Poster Title: Exploiting the Egg Laying Neuro-circuitry of Caenorhabditis elegans to Identify Novel Modulators of Conserved Regulators of Neuromuscular Control. (ppt titled: 170428—SH Donnelly Retreat Poster, (Year: 2017).

Liquid crystal-related compound-induced cell growth suppression and apoptosis in the chronic myelogenous leukemia K562 cell line, Yukako Fukushi et al. Invest New Drugs, vol. 29, pp. 827-832, 2011.

Block Copolymer Micelles for Controlled Delivery of Glycolytic Enzyme Inhibitors, Shjida Akter et al. Pharmaceutical Resarch vol. 29(3), pp. 847-855, 2012.

Corrected International Search Report and Written Opinion of corresponding International Application No. PCT/CA2019/051271, dated Jan. 16, 2020, 14 pages.

COMPOUNDS AND METHODS FOR TREATING NEMATODE INFECTIONS

RELATED APPLICATIONS

The present application is a national stage application of International Application no. PCT/CA2019/051271, filed on Sep. 10, 2019, which claims the benefit of priority of U.S. provisional patent application No. 62/730,286 filed on Sep. 12, 2018, the contents of each of which are incorporated herein by reference in their entirety.

FIELD

The present application relates to the treatment of nematode infections. For example, the application relates to the use of one or more compounds of Formula (III) as defined herein for treatment of a nematode infection or a disease, disorder or condition arising from a nematode infection.

INTRODUCTION

The burden of parasitic nematodes on humanity is severe. The WHO estimates that over two billion people are infected with at least one parasitic nematode species. Chronic infection can cause dietary deficiency, anemia, developmental delay, elephantiasis, blindness, and death. Human infection in the west is increasing, coincident with a warming climate and the movement of sub-tropical species northward. Soil-transmitted helminth (STH) species, including the hookworms *Ancylostoma duodenale* and *Necator americanus*, the roundworm *Ascaris lumbricoides*, and the whipworm *Trichuris trichiura*, currently infect more than 1.5 billion people. Infection from STHs and other nematode species can cause malnutrition, anemia, developmental delay, intellectual impairment, elephantiasis, blindness, and death. Over 130,000 deaths per year are attributed to severe nematode infection. Intestinal nematode infections alone are responsible for an estimated disease burden of 3.4 million disability-adjusted life-years.

Nearly all anthelmintics (compounds that kill parasitic nematodes of animals) used to treat humans were first developed for the purpose of curing nematode infections of livestock. This is because humans infected with nematodes are typically from impoverished nations, while western farms suffer severe losses due to nematodes. Western agriculture therefore provides the economic incentive for anthelmintic development and these molecules are later adopted for human use. The most common anthelmintics that have been adopted to treat human nematode infections include the benzimidazoles, pyrantel, levamisole, ivermectin, and nitazoxanide.

Most anthelmintics disrupt the worm's nervous system, which ultimately allows the mammalian host to clear the infection. For example, key targets of ivermectin are glutamate-gated chloride channels of the nervous system. Ivermectin agonizes these channels and hyperpolarizes the cell, in turn leading to paralysis. Similarly, levamisole agonizes nicotinic acetylcholine receptors leading to depolarization of muscles and, in turn, paralysis.

There is '. . . a clear need for new anthelmintic drugs to ensure access to efficacious treatment options in the future.' This is a direct quote from a consortium of global public health scientists, published in a 2018 Policy Platform document in the Public Library of Science (PLoS). While anthelmintic resistance has been reported in humans, our understanding of resistance is not clear because these diseases are endemic to under-developed countries with few resources for epidemiological studies. What is clear is that anthelmintic resistance in agriculture develops very quickly. It is therefore widely anticipated that as human anthelmintic drug administration intensifies, nematode resistance to the anthelmintics is certain to flourish.

Further, it is estimated that over 350 billion dollars worth of crops are destroyed by plant parasitic nematodes (PPNs) every year. Staple food crops that are impacted by these parasites include small grains, potatoes, and soybeans to name just a few. Countries around the world are phasing out or outright banning popular nematicides because of health or environmental concerns. The decreasing number of tools to manage nematode infestation limits the farmer's ability to optimize crop production. Given the world's increasing population, decreasing arable land, and reduced crop yields because of changing weather patterns its important that the destruction of crops by pests be minimized to feed the world in a cost-efficient manner.

Good cultural practices, biologicals, and GMOs, are often not sufficient to control PPNs. Chemical nematicides have consequently been a key part of a complete PPN control strategy for decades. However, concerns over environmental toxicity and human safety have justifiably prompted restrictions and bans on many effective nematicides, including the fumigant methyl bromide, and neurotoxic organophosphates and carbamates. Regulations have limited the number of available nematicides such that there are no longer reliable control options for several PPN species, including *Meloidogyne hapla* that parasitizes Canadian potatoes, onion, tomatoes and other crops.

Furthermore, nematode infestation of food increases costs and contributes to malnutrition. Nematodes have evolved widespread resistance to nearly every anthelmintic (anti-worm) drug on the market. Hence, there is a dire need for the development of new compounds that kill parasitic worms.

SUMMARY

It has been shown herein that compounds of Formula (III) provide inhibitory activity against species of nematodes such as *Cooperia oncophora, Haemonchus contortus, Caenorhabditis elegans, Pristionchus pacificus, Phasmarhabditis hermaphrodita, Necator americanis, Trichuris muris, Strongyloides ratti, Meloidogyne incognita* and *Meloidogyne chitwoodi*.

Accordingly, the present application includes methods and uses for treating or preventing a nematode infection comprising administering an effective amount of one or more compounds of Formula (III)

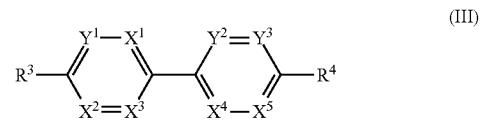

(III)

and/or a pharmaceutically acceptable salt and/or solvate thereof to a subject in need thereof, wherein:

$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;

$R^4$ is H, OH, halo, $C_{1-10}$alkyl, $C_{2-10}$alkenyl, $C_{2-10}$alkynyl, $OC_{1-10}$alkyl, $OC_{1-10}$haloalkyl, $SC_{1-10}$alkyl or $SC_{1-10}$haloalkyl, the latter seven groups being unsubstituted or substituted with CN, or $C(O)NH_2$;

$X^1$, $X^2$, $X^3$, $X^4$ and $X^5$ are independently $CR^7$ or N;
$Y^1$, $Y^2$ and $Y^3$ are independently $CR^8$;
$R^5$ and $R^6$ are independently H or $C_{1-6}$alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and
$R^9$ and $R^{10}$ are independently H or $C_{1-6}$alkyl.

In some embodiments, the present application includes methods and uses of treating or preventing a disease, disorder or condition arising from a nematode infection comprising administering an effective one or more compounds of Formula (III)

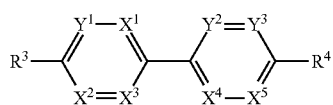
(III)

and/or a pharmaceutically acceptable salt and/or solvate thereof to a subject in need thereof, wherein:
$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;
$R^4$ is H, OH, halo, $C_{1-10}$alkyl, $C_{2-10}$alkenyl, $C_{2-10}$alkynyl, $OC_{1-10}$alkyl, $OC_{1-10}$haloalkyl, $SC_{1-10}$alkyl or $SC_{1-10}$haloalkyl, the latter seven groups being unsubstituted or substituted with CN, or $C(O)NH_2$;
$X^1$, $X^2$, $X^3$, $X^4$ and $X^5$ are independently $CR^7$ or N;
$Y^1$, $Y^2$ and $Y^3$ are independently $CR^8$;
$R^5$ and $R^6$ are independently H or $C_{1-6}$alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and
$R^9$ and $R^{10}$ are independently H or $C_{1-6}$alkyl.

In some embodiments, the present application includes pharmaceutical compositions comprising a pharmaceutically acceptable carrier and one or more compounds of Formula (III)

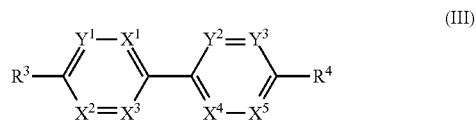
(III)

and/or a pharmaceutically acceptable salt and/or solvate thereof to a subject in need thereof, wherein:
$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;
$R^4$ is H, OH, halo, $C_{1-10}$alkyl, $C_{2-10}$alkenyl, $C_{2-10}$alkynyl, $OC_{1-10}$alkyl, $OC_{1-10}$haloalkynl, $SC_{1-10}$alkyl or $SC_{1-10}$haloalkyl, the latter seven groups being unsubstituted or substituted with CN, or $C(O)NH_2$;
$X^1$, $X^2$, $X^3$, $X^4$ and $X^5$ are independently $CR^7$ or N;
$Y^1$, $Y^2$ and $Y^3$ are independently $CR^8$;
$R^5$ and $R^6$ are independently H or $C_{1-6}$alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and
$R^9$ and $R^{10}$ are independently H or $C_{1-6}$alkyl.

In some embodiments, the present application includes uses of pharmaceutical compositions comprising a compound of Formula (III) for treating or preventing a nematode infection or a disease, a disorder, or a condition arising from a nematode infection in a subject in need thereof.

In some embodiments, the present application includes a nematicidal composition comprising a carrier and one or more compounds of Formula (III)

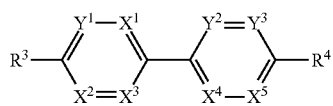
(III)

and/or a pharmaceutically acceptable salt and/or solvate thereof to a subject in need thereof, wherein:
$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;
$R^4$ is H, OH, halo, $C_{1-10}$alkyl, $C_{2-10}$alkenyl, $C_{2-10}$alkynyl, $OC_{1-10}$alkyl, $OC_{1-10}$haloalkyl, $SC_{1-10}$alkyl or $SC_{1-10}$haloalkyl, the latter seven groups being unsubstituted or substituted with CN, or $C(O)NH_2$;
$X^1$, $X^2$, $X^3$, $X^4$ and $X^5$ are independently $CR^7$ or N;
$Y^1$, $Y^2$ and $Y^3$ are independently $CR^8$;
$R^5$ and $R^6$ are independently H or $C_{1-6}$alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and
$R^9$ and $R^{10}$ are independently H or $C_{1-6}$alkyl.

The present application also includes one or more compounds of Formula (III-A)

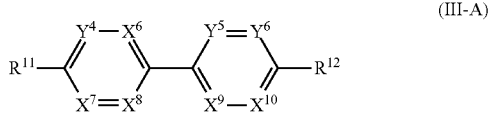
(III-A)

or a pharmaceutically acceptable salt and/or solvate thereof, wherein:
$R^{11}$ is H, $C_{1-4}$alkyl, $C_{2-10}$alkenyl, $C_{2-10}$alkynyl, $C_{1-10}$alkyleneNR$^{13}$R$^{14}$, $C_{2-10}$alkenyleneNR$^{13}$R$^{14}$ or $C_{2-10}$alkynyleneNR$^{13}$R$^{14}$;
$R^{12}$ is H, OH, $C_{1-8}$alkyl, $C_{2-10}$alkenyl, $C_{2-10}$alkynyl, $C_{1-10}$haloalkyl, $OC_{1-6}$alkyl, $OC_{2-10}$alkenyl, $OC_{2-10}$alkynyl, $OC_{1-10}$haloalkyl, $SC_{1-10}$alkyl or $SC_{1-10}$haloalkyl;
$X^6$, $X^7$, $X^8$, $X^9$ and $X^{10}$ are independently $CR^{15}$ or N;
$Y^4$, $Y^5$ and $Y^6$ are independently $CR^{16}$;
$R^{13}$ and $R^{14}$ are independently H or $C_{1-6}$alkyl;
$R^{15}$ and $R^{16}$ are independently H, halo, $C_{1-6}$alkyl, $C_{1-6}$haloalkyl, $OC_{1-10}$alkyl or $OC_{1-6}$haloalkyl the latter four groups being unsubstituted or substituted with $NR^{17}R^{18}$; and
$R^{17}$ and $R^{18}$ are independently H or $C_{1-6}$alkyl;
provided the compound is not 2-(4-(trifluoromethoxy)phenyl)-5-propylpyridine or 2-(4-(difluoromethoxy)phenyl)-5-propylpyridine.

In some embodiments, the present application includes uses of the nematicidal composition described herein for treating or preventing a nematode infection or a disease, a disorder, or a condition arising from a nematode infection in a subject in need thereof.

In some embodiments, the present application includes methods of treating or preventing a nematode infection comprising administering an effective amount of a nematicidal composition described herein to a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 shows movement defects induced by exemplary compound IIIc. Panel A shows a negative control healthy *C. elegans* worm without drug. Panel B shows the "rubber band" phenotype of a *C. elegans* worm in presence of exemplary compound IIIc.

FIG. 2 shows a time-course analysis of the behavioural defects induced by exemplary compound IIIa (wact-55-1) and exemplary compound II (wact-55-12-1). Panel A shows a time-course analysis of animal's behaviour on 60 uM of exemplary compound IIIa (wact-55-1). Panel B shows a time-course analysis of animal's behaviour on 60 uM of exemplary compound II (wact-55-12-1). Biological replicates =2; error bars show the standard deviation.

FIG. 3 shows exemplary compound IIIa (wact-55-1) does not decrease the proliferation of HEK293 or HEPG2 cells. Panel A shows the impact of exemplary compound IIIa (wact-55-1) on human-derived HEK293 cell proliferation. Panel B shows the impact of exemplary compound IIIa (wact-55-1) on human liver-derived HEPG2 cell proliferation. Panel C shows the impact of exemplary compound II (wact-55-12-1) on human liver-derived HEPG2 cell proliferation. Error bars shows the standard deviation (SD) of three biological repeats.

FIG. 4 shows exemplary compound IIIa (wact-55-1) does not disrupt zebrafish physiology in obvious ways. Zebrafish were incubated with the indicated treatment and heartbeat was recorded either at 10 minutes (for carbaryl) or before a 60 minute time point. Data is the average of two biological replicates (with 3 animals per replicate)±s.e.m.

Figure 7:
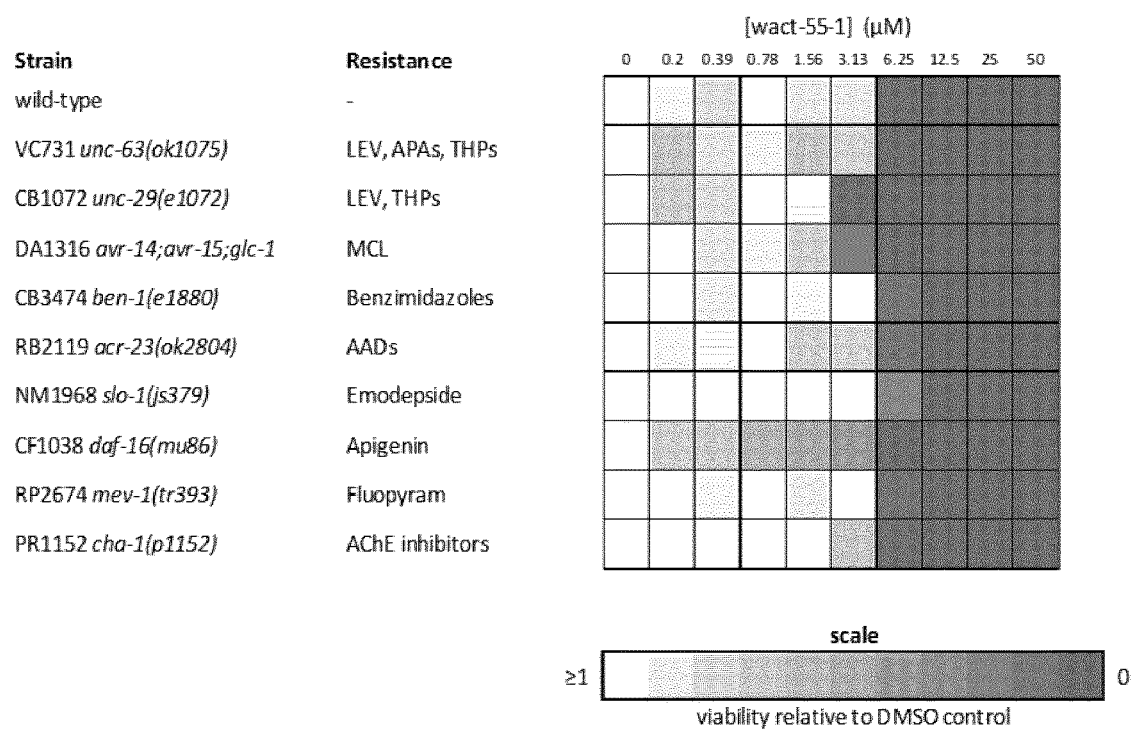

FIG. 7 shows exemplary compound IIIa (wact-55-1) kills canonical anthelmintic and nematicide resistant *C. elegans* strains. The exemplary compound IIIa (wact-55-1) dose-response of the *C. elegans* wild-type N2 strain and 9 *C. elegans* mutant strains that are resistant to established anthelmintics and nematicides are shown. The dose-response assays were performed using 25 L1 larvae per well. The number of viable worms in each condition after a 72 hour incubation relative to the DMSO controls is indicated by the colour-coded scale. The anthelmintic or nematicide resistance of each strain is indicated. Abbreviations: LEV, levamisole; APA, aminophenylamidine; THP, tetrahydropyrimidine; MCL, Macrocyclic Lactone; AAD, aminoacetonitrile derivative; AchE, acetylcholinesterase. The assay was done with technical duplicates and one biological replicate.

Figure 8:
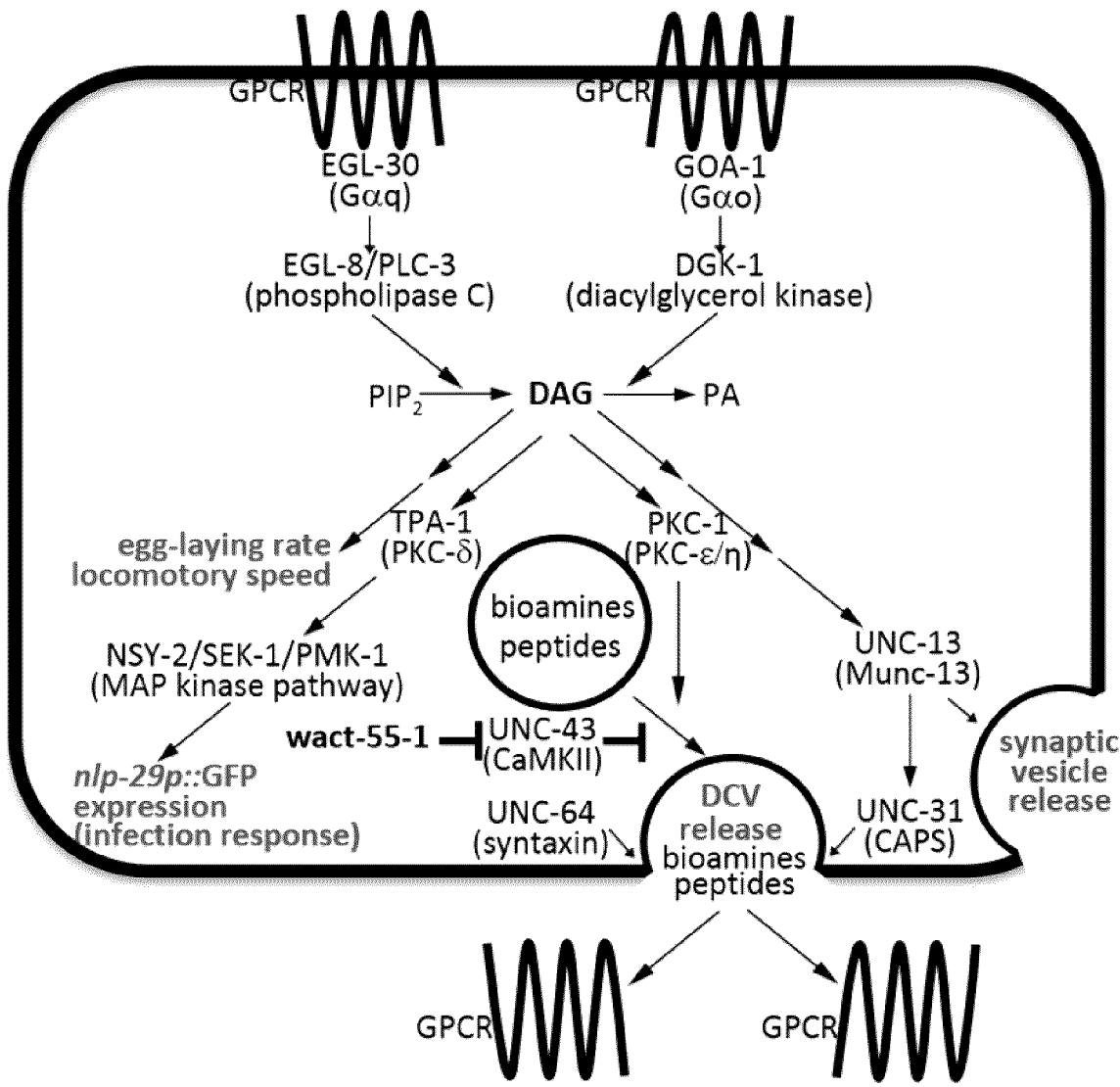

FIG. 8 shows a model for how exemplary compound IIIa (wact-55-1) induces motor defects. The data herein supports a model wherein UNC-43/CaMKII is inhibited. Given that UNC-43 negatively regulates dense core vesicles (DCVs) release, it suggests that exemplary compound IIIa (wact-55-1) indirectly promotes DCV release. DAG, diacylglycerol; PA, phosphatidic acid.

Figure 9:
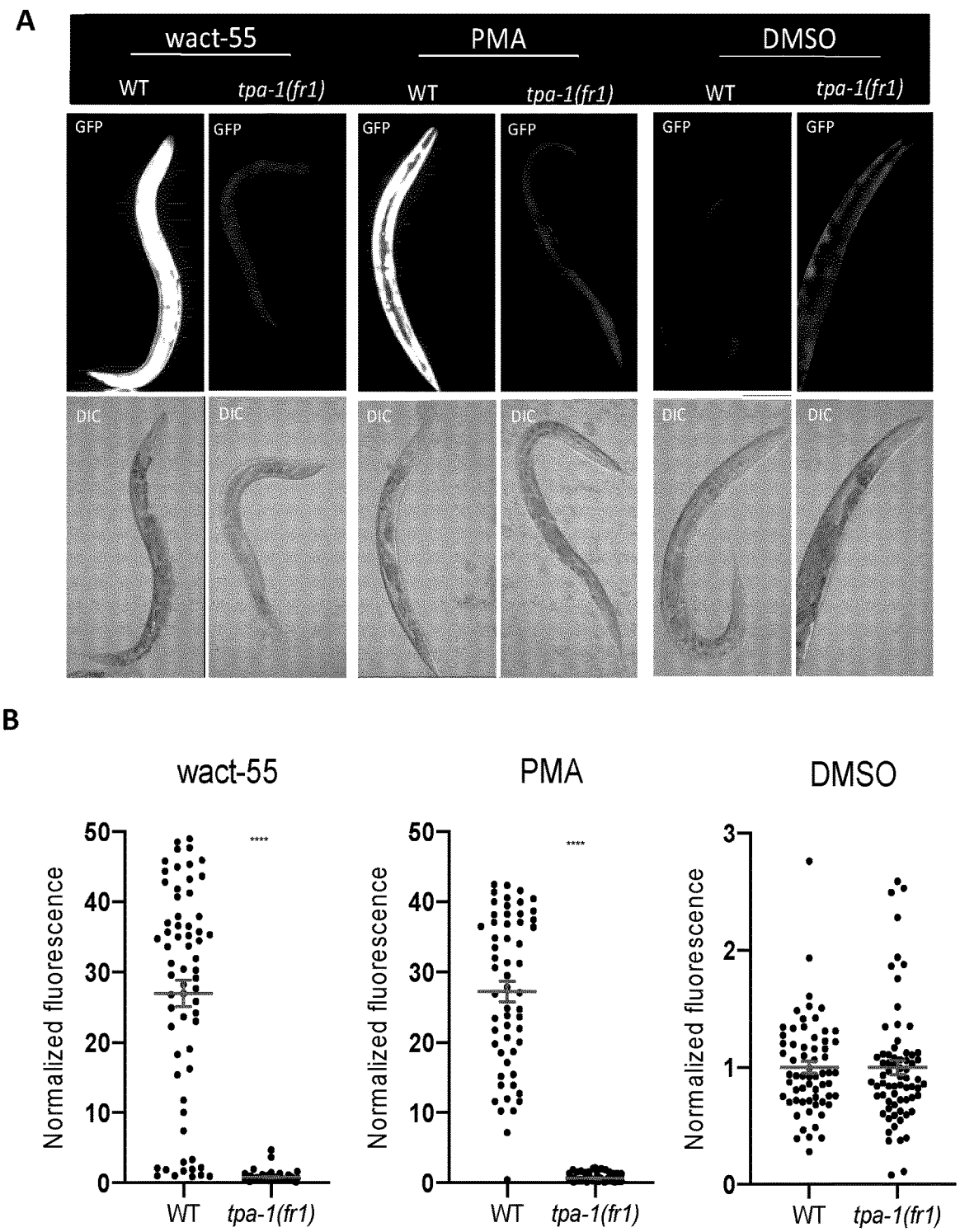

FIG. 9 shows exemplary compound IIIa (wact-55-1) treatment results DAG production in a protein kinase c d (tpa-1)-dependent manner. Panel A shows representative images are shown of the nlp-29p::GFP expressing wild type and tpa-1(fr1) L4 larvae treated with 15 μM of exemplary compound IIIa (wact-55-1) 1 or 0.5 μg/mL of phorbol myristate acetate (PMA) for 24 hours in liquid culture. Panel B shows a dot-plot quantification of the fluorescent signal emitted by the reporter strain in the indicated genetic background over three biological replicates. Mean grey values of worms treated with exemplary compound IIIa (wact-55) and PMA were normalized to controls in the dimethylsulfoxide (DMSO) (1% (v/v)) vehicle control. * $p<0.05$; * $p<0.001$; ** $p<0.0001$.

Figure 10:
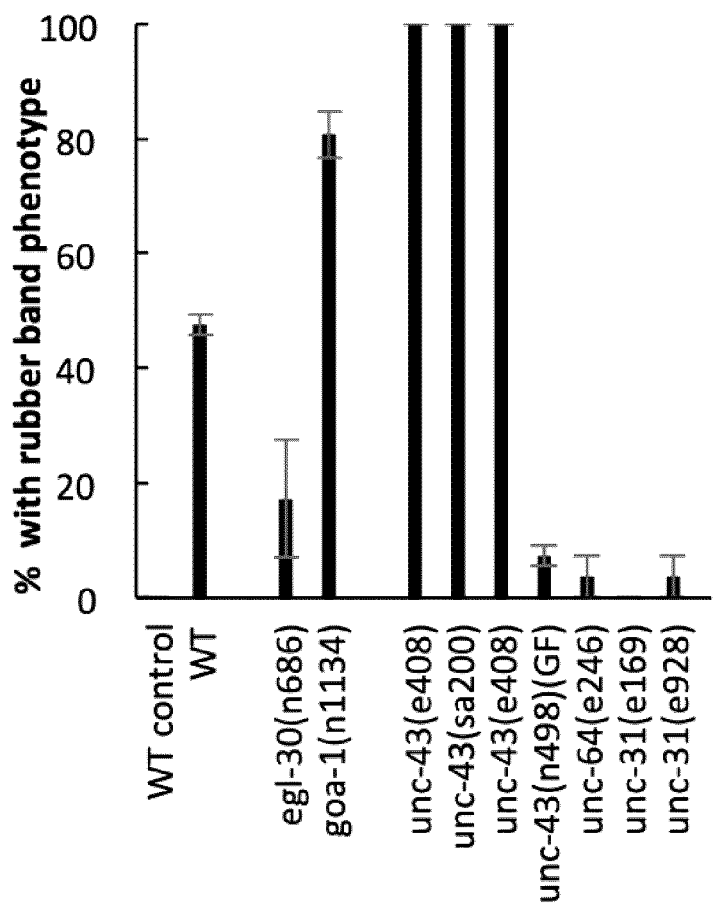

FIG. 10 shows genetic Interactions with exemplary compound IIIa (wact-55-1). Animals with the indicated genotype were scored for convulsions after incubating for 80 minutes on solid agar substrate containing 60 mM exemplary compound IIIa (wact-55-1). 'WT control' was tested in response to vehicle only. All characterized alleles are reduction-of-function (RF) except for the indicated GF. The data are from 2-9 biological replicates scoring 18 animals each. Standard of deviation is shown.

Figure 11:
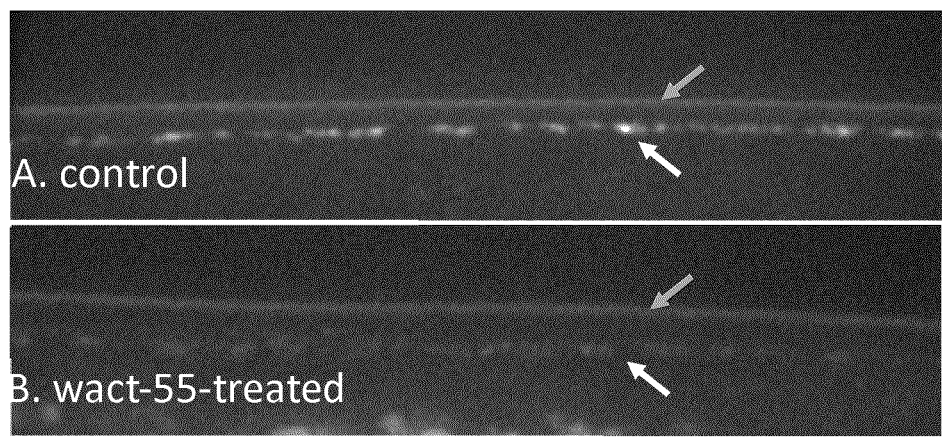

FIG. 11 shows exemplary compound IIIa (wact-55-1) induces DCV release. GFP-marked DCVs in motor neurons are indicated with the arrow on the bottom of each image. The cuticle is indicated using the arrow on the top of each panel. Animals were treated with either DMSO control (Panel A) or 60 mM compound IIIb (wact-55b) (Panel B) for 4 hours and then imaged. The signal was quantified (not shown) and found to be significantly lower in wact-55 treated animals ($p<0.001$).

DESCRIPTION OF VARIOUS EMBODIMENTS

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. The term "and/or" with respect to pharmaceutically acceptable, salts and/or solvates thereof means that referenced compounds exist as individual salts or hydrates, as well as a combination of, for example, a salt of a solvate of a compound.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "compounds of the application" as used herein includes compounds of Formula (III) as well as salts and/or solvates thereof, including compounds of Formula (III-A) and salts and/or solvates thereof.

The compounds of the application may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "alkenylene", whether it is used alone or as part of another group, means straight or branched chain, unsaturated alkenylene group, that is, an unsaturated carbon chain that contains at least one double bond and substituents on two of its ends. The number of carbon atoms that are possible in the referenced alkenylene group are indicated by the prefix "$C_{n1-n2}$". For example, the term $C_{2-6}$alkenylene means an alkylene group having 2, 3, 4, 5 or 6 carbon atoms.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms.

The term "alkynylene", whether it is used alone or as part of another group, means straight or branched chain, unsaturated alkynylene group, that is, an unsaturated carbon chain that contains at least one triple bond and substituents on two of its ends. The number of carbon atoms that are possible in the referenced alkynylene group are indicated by the prefix "$C_{n1-n2}$". For example, the term $C_{2-6}$alkynylene means an alkynylene group having 2, 3, 4, 5 or 6 carbon atoms.

The term "amine" or "amino," as used herein, whether it is used alone or as part of another group, refers to groups of the general formula NR'R", wherein R' and R" are each independently selected from hydrogen or $C_{1-6}$alkyl.

The term "haloalkyl" as used herein, refers to the substitution of one or more, including all, available hydrogens in a referenced group with halo.

The terms "halo" or "halogen" as used herein, whether it is used alone or as part of another group, refers to a halogen atom and includes fluoro, chloro, bromo and iodo.

The term "fluoroalkyl" as used herein, refers to the substitution of one or more, including all, available hydrogens in a referenced group with F.

The term "chloroalkyl" as used herein, refers to the substitution of one or more, including all, available hydrogens in a referenced group with Cl.

The term "chlorofluoroalkyl" as used herein, refers to the substitution of two or more, including all, available hydrogens in a referenced group with a combination of Cl and F.

The term "available", as in "available hydrogen atoms" or "available atoms" refers to atoms that would be known to a person skilled in the art to be capable of replacement by a substituent. The term "nematode infection" as used herein refers to an invasion of cells or bodily tissues by a foreign undesirable nematode.

The term "anthelmintic" or "anthelmintics" as used herein refers to a group of antiparasitic drug used in the treatment and prevention of nematode infections.

As used herein, a compound with "anthelmintic activity" is a compound, which when tested, has measurable nematode-killing activity or results in sterility or reduced fertility in the nematodes such that fewer viable or no offspring result, or compromises the ability of the nematode to infect or reproduce in its host, or interferes with the growth or development of a nematode. The compound may also display nematode repellant properties.

The term "pharmaceutically acceptable salt" means an acid addition salt or a basic addition salt suitable for, or compatible with, the treatment of subjects.

The term "pharmaceutically acceptable salts" embraces salts commonly used to form addition salts of free acids or free bases. The nature of the salt is not critical, provided that it is pharmaceutically-acceptable. Suitable pharmaceutically acceptable acid addition salts are prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids include, for example, aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine.

The term "solvates" as used herein refers to complexes formed between a compound and a solvent from which the compound is precipitated or in which the compound is made. Accordingly, the term "solvate" as used herein means a compound, or a salt a compound, wherein molecules of a suitable solvent are incorporated in the crystal lattice. Examples of suitable solvents are ethanol, water and the like. When water is the solvent, the molecule is referred to as a "hydrate".

The term "pharmaceutically acceptable solvate" means a solvate suitable for, or compatible with, the treatment of subjects. For pharmaceutically acceptable solvates, a suitable solvent is physiologically tolerable at the dosage used or administered.

The term "wact-55", "w-55" or "wact-55-1" is used interchangeably herein and refers to compound IIIa of Formula (III). The term "compounds of wact-55 family" or "compounds of w-55 family" refers to compounds of Formula (III).

The term "wact-55b" or "w-55b" as used herein refers to the compound of Formula IIIb.

The term "wact-12-1" as used herein refers to the compound of Formula IIIi.

The expression "disease, disorder or condition arising from a nematode infection" as used herein refers to any disease, disorder or condition that is directly or indirectly caused by the presence of a nematode infection in a subject.

The term "subject" as used herein includes plants, seeds, soil, and all members of the animal kingdom including mammals and birds, and their food. Thus, the methods of the present application are applicable to plant treatment, human therapy and veterinary applications.

When used, for example, with respect to the methods of treatment, uses, compositions and kits of the application, a subject, for example a subject "in need thereof" is a subject who has been diagnosed with, is suspected of having, may come in to contact with, and/or was previously treated for a nematode infection or a disease, disorder or condition arising from a nematode infection.

When used, for example, in respect to plant treatments, the compounds and/or compositions may be delivered by several means including pre-planting, post-planting and as a feed additive, drench, external application, pill or by injection.

The term "pharmaceutical composition" as used herein refers to a composition of matter for pharmaceutical use.

The term "pharmaceutically acceptable" means compatible with the treatment of subjects.

The term "nematicidal composition" as used here in refers to a composition of matter for managing one or more nematode infections.

The term "administered" as used herein means administration of an effective amount of a compound, including compounds of Formula (III) or (III-A), or a salt and/or solvate thereof, to a cell either in cell culture or in a subject.

As used herein, the term "effective amount" or "therapeutically effective amount" means an amount effective, at dosages and for periods of time necessary to achieve a desired result. For example, in the context of treating a nematode infection, or a disease, disorder or condition arising from a nematode infection, an effective amount of a compound is an amount that, for example, reduces the nematode infection compared to the nematode infection without administration of the compound. By "reducing the infection", it is meant, for example, reducing the amount of the infectious agent in the subject and/or reducing the symptoms of the infection. The amount of a given compound or composition that will correspond to such an amount will vary depending upon various factors, such as the given compound or composition, the formulation, the route of administration, the type of condition, disease or disorder, the identity of the subject being treated, and the like, but can nevertheless be routinely determined by one skilled in the art.

The terms "to treat", "treating" and "treatment" as used herein and as is well understood in the art, means an approach for obtaining beneficial or desired results, including clinical results. Beneficial or desired clinical results include, but are not limited to, diminishment of extent of nematode infection, stabilization (i.e. not worsening) of the state of the nematode infection, preventing spread of the nematode infection, delay or slowing of infection progression, amelioration or palliation of the nematode infectious state, diminishment of the reoccurrence of nematode infection, diminishment, stabilization, alleviation or amelioration of one or more diseases, disorders or conditions arising from the nematode infection, diminishment of the reoccurrence of one or more diseases, disorders or conditions arising from the nematode infection, and remission of the nematode infection and/or one or more symptoms or conditions arising from the nematode infection, whether partial or total, whether detectable or undetectable. "To treat", "treating" and "treatment" can also mean prolonging survival as compared to expected survival if not receiving treatment. "To treat", "treating" and "treatment" as used herein also include prophylactic treatment. For example, a subject with an early nematode infection is treated to prevent progression, or alternatively a subject in remission is treated to prevent recurrence.

"Palliating" an infection, disease, disorder and/or condition means that the extent and/or undesirable manifestations of an infection, disease, disorder and/or condition are lessened and/or time course of the progression is slowed or lengthened, as compared to not treating the infection, disease, disorder and/or condition.

The term "prevention" or "prophylaxis" and the like as used herein refers to a reduction in the risk or probability of a subject becoming afflicted with a nematode infection and/or a disease, disorder and/or condition arising from a nematode infection or manifesting a symptom associated with a nematode infection and/or a disease, disorder and/or condition arising from a nematode infection.

II. Methods and Uses of the Application

A family of small molecule compounds have been identified that incapacitate parasitic nematodes, and advantageously show evidence of no genetic resistance. This suggests that resistance to these compounds will be less likely to develop in the wild.

The present application includes methods for treating or preventing a nematode infection comprising administering an effective amount of one or more compounds of Formula (III)

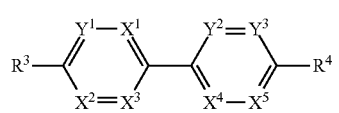

(III)

and/or a pharmaceutically acceptable salt and/or solvate thereof to a subject in need thereof, wherein:
$R^3$ is H, $NR^5R^6$, $C_{2-10}$alkenyl, $C_{2-10}$alkynyl, $C_{1-10}$alkyleneNR$^5$R$^6$; $C_{2-10}$alkenyleneNR$^5$R$^6$ or $C_{2-10}$alkynyleneNR$^5$R$^6$;
$R^4$ is H, OH, halo, $C_{1-10}$alkyl, $C_{2-10}$alkenyl, $C_{2-10}$alkynyl, $OC_{1-10}$alkyl, $OC_{1-10}$halolkyl, $SC_{1-10}$alkyl or $SC_{1-10}$haloalkyl, the latter seven groups being unsubstituted or substituted with CN, or C(O)NH$_2$;
$X^1$, $X^2$, $X^3$, $X^4$ and $X^5$ are independently CR$^7$ or N;
$Y^1$, $Y^2$ and $Y^3$ are independently CR$^8$;
$R^5$ and $R^6$ are independently H or $C_{1-6}$ alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with NR$^9$R$^{10}$; and
$R^9$ and $R^{10}$ are independently H or $C_{1-6}$alkyl.

In one embodiment, the present application includes methods and uses for treating or preventing a nematode infection comprising administering an effective amount of a compound of Formula (III)

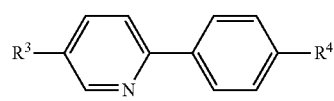

III and/or a pharmaceutically acceptable salt and/or solvate thereof to a subject in need thereof, wherein
$R^3$ is $C_{1-10}$alkyl; and
$R^4$ is OH, halo, $OC_{1-10}$fluoroalkyl or $OC_{1-10}$alkyl, the latter group being unsubstituted or substituted with CN or C(O)NH$_2$.

In some embodiments, the present application includes methods of treating or preventing a disease, disorder or condition arising from a nematode infection comprising administering an effective amount one or more compounds of Formula (III)

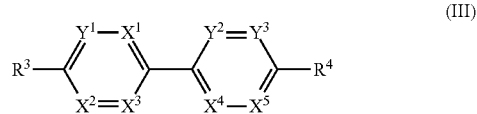

(III)

and/or a pharmaceutically acceptable salt and/or solvate thereof to a subject in need thereof, wherein:
$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;
$R^4$ is H, OH, halo, $C_{1-10}$alkyl, $C_{2-10}$alkenyl, $C_{2-10}$alkynyl, $OC_{1-10}$alkyl, $OC_{1-10}$haloalkynl, $SC_{1-10}$alkyl or $SC_{1-10}$haloalkyl, the latter seven groups being unsubstituted or substituted with CN, or C(O)NH$_2$;
$X^1$, $X^2$, $X^3$, $X^4$ and $X^5$ are independently CR$^7$ or N;
$Y^1$, $Y^2$ and $Y^3$ are independently CR$^8$;
$R^5$ and $R^6$ are independently H or $C_{1-6}$alkyl;
$R^7$ and $R^8$ are independently H, halo, $C_{1-10}$alkyl, $OC_{1-10}$alkyl or $OC_{1-10}$haloalkyl, the latter three groups being unsubstituted or substituted with NR$^9$R$^{10}$; and
$R^9$ and $R^{10}$ are independently H or $C_{1-6}$alkyl.

In some embodiments, the present application includes methods and uses of treating or preventing a disease, disorder or condition arising from a nematode infection comprising administering an effective amount a compound of Formula (III)

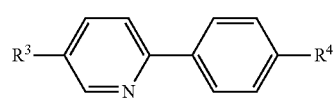

III and/or a pharmaceutically acceptable salt and/or solvate thereof to a subject in need thereof, wherein
$R^3$ is $C_{1-10}$alkyl; and
$R^4$ is OH, halo, $OC_{1-10}$fluoroalkyl or $OC_{1-10}$alkyl, the latter group being unsubstituted or substituted with CN or C(O)NH$_2$.

In some embodiments, the present application includes a use of pharmaceutical compositions comprising one or more compounds of Formula (III), or pharmaceutically acceptable salts and/or solvates thereof, for treating or preventing a nematode infection or a disease, a disorder, or a condition arising from a nematode infection in a subject in need thereof.

In some embodiments, the present application includes methods of treating or preventing a nematode infection comprising administering an effective amount of a nematicidal composition comprising one or more compounds of Formula (III), or pharmaceutically acceptable salts and/or solvates thereof, described herein to a subject in need thereof.

In some embodiments, the present application includes uses of a nematicidal composition comprising one or more compounds of Formula (III), or pharmaceutically acceptable salts and/or solvates thereof, described herein for treating or preventing a nematode infection or a disease, a disorder, or a condition arising from a nematode infection in a subject in need thereof.

In some embodiments, the present application includes a use of one or more compounds of Formula (III), or pharmaceutically acceptable salts and/or solvates thereof, for treating or preventing a nematode infection or a disease, a disorder, or a condition arising from a nematode infection, as well as a use of one or more compounds of Formula (III), or pharmaceutically acceptable salts and/or solvates thereof, for preparation of a medicament for treating or preventing a nematode infection or a disease, a disorder, or a condition arising from a nematode infection. Also included in the present application is one or more compounds of Formula (III), or pharmaceutically acceptable salts and/or solvates thereof, for use in treating or preventing a nematode infection or a disease, a disorder, or a condition arising from a nematode infection.

In some embodiments, one of $X^1$, $X^2$, $X^3$, $X^4$ and $X^5$ is N and the others are independently $CR^7$. In some embodiments $X^3$ is N and $X^1$, $X^2$, $X^4$ and $X^5$ are independently $CR^7$. In some embodiments $X^2$ is N and $X^1$, $X^3$, $X^4$ and $X^5$ are independently $CR^7$. In some embodiments $X^4$ is N and $X^1$, $X^2$, $X^3$ and $X^5$ are independently $CR^7$. In some embodiments $X^5$ is N and $X^1$, $X^2$, $X^3$ and $X^4$ are independently $CR^7$. In some embodiments $X^1$ and $X^3$ are both N and $X^2$, $X^4$ and $X^5$ are independently $CR^7$.

In some embodiments, $R^7$ and $R^8$ are independently H, F, Cl, $C_{1-6}$alkyl, 6alkyl or $OC_{1-6}$haloalkyl, the latter three groups being unsubstituted or substituted with $NR^9R^{10}$. In some embodiments, $R^7$ and $R^8$ are independently H, F, Cl, $C_{1-4}$alkyl, $OC_{1-4}$alkyl, $OC_{1-4}$fluoroalkyl or $C_{1-4}$alkylNR$^9$R$^{10}$. In some embodiments, $R^9$ and $R^{10}$ are independently H or $C_{1-4}$alkyl. In some embodiments, $R^9$ and $R^{10}$ are both H. In some embodiments, one of $R^9$ and $R^{10}$ is H and the other is $CH_3$ or $CH_2CH_3$. In some embodiments, $R^9$ and $R^{10}$ are both $CH_3$.

In some embodiments, $R^7$ and $R^8$ are independently H, F, Cl, $CH_3$, $CH_2CH_3$, $CH_2CH_2CH_3$, $CH_2CH_2CH_2CH_3$, $CH_2NH_2$, $CH_2CH_2NH_2$, $CH_2CH_2CH_2NH_2$, $OCH_3$, $OCHF_2$, $OCH_2F$, $OCHFCl$, $OCF_3$, $OCHCl_2$, $OCHFCl$ or $OCCl_3$. In some embodiments, $R^7$ and $R^8$ are independently H, F, $CH_3$, $CH_2CH_3$, $CH_2CH_2CH_3$, $CH_2NH_2$, $CH_2CH_2NH_2$, $OCH_3$, $OCHF_2$, $OCH_2F$, $OCHFCl$, $OCF_3$, $OCHCl_2$, $OCHFCl$ or $OCCl_3$.

In some embodiments, $R^3$ is H, $NR^5R^6$, $C_{1-8}$alkyl, $C_{2-6}$alkenyl, $C_{2-6}$alkynyl, $C_{1-6}$alkyleneNR$^5R^6$, $C_{2-6}$alkenyleneNR$^5R^6$ or $C_{2-6}$alkynyleneNR$^5R^6$. In some embodiments, $R^5$ and $R^6$ are independently H or $C_{1-4}$alkyl. In some embodiments, $R^5$ and $R^6$ are both H. In some embodiments, one of $R^5$ and $R^6$ is H and the other is $CH_3$ or $CH_2CH_3$. In some embodiments, $R^6$ and $R^6$ are both $CH_3$.

In some embodiments, $R^3$ is H, $NH_2$, $C_{1-8}$alkyl, $C_{2-4}$alkenyl, $C_{2-4}$alkynyl, $C_{1-6}$alkyleneNH$_2$. In some embodiments, $R^3$ is $NH_2$ or $C_{1-6}$alkyleneNH$_2$. In some embodiments, $R^3$ is $NH_2$ or $C_{1-3}$alkyleneNH$_2$. In some embodiments, $R^3$ is $C_{1-8}$alkyl, $C_{2-4}$alkenyl or $C_{2-4}$alkynyl. In some embodiments, $C_{2-4}$alkynyl is —CECCH$_3$. In some embodiments, $R^3$ is $C_{1-8}$alkyl. In some embodiments, $R^3$ is straight chain $C_{1-8}$alkyl. In some embodiments, $R^3$ is branched $C_{1-8}$alkyl. In some embodiments, $R^3$ is H.

In some embodiments, $R^4$ is H, OH, halo, $C_{1-6}$alkyl, $C_{2-6}$alkenyl, $C_{2-6}$alkynyl, $OC_{1-6}$alkyl, $OC_{1-6}$haloalkyl, $SC_{1-6}$alkyl or $SC_{1-6}$haloalkyl, the latter seven groups being unsubstituted or substituted with CN, or $C(O)NH_2$. In some embodiments, $R^4$ is $C_{1-6}$alkyl, $C_{2-6}$alkenyl, $C_{2-6}$alkynyl, $OC_{1-6}$chloroalkyl, $OC_{1-6}$fluorooalkyl, 6chloroalkyl, $SC_{1-6}$fluoroalkyl or $OC_{1-6}$chlorofluoroalkyl. In some embodiments, $R^4$ is $C_{1-6}$alkyl, $C_{2-6}$alkenyl, or $C_{2-6}$alkynyl. In some embodiments, $R^4$ is $C_{1-6}$alkyl. In some embodiments, $R^4$ is OH, $OC_{1-6}$alkyl, $OC_{1-4}$chloroalkyl, $OC_{1-4}$fluorooalkyl, $SC_{1-4}$fluoroalkyl or $OC_{1-4}$chlorofluoroalkyl. In some embodiments, $R^4$ is OH, $OC_{1-6}$alkyl, $OCHF_2$, $OCH_2F$, $OCHFCl$, $OCF_3$, $OCHCl_2$, $OCHFCl$, $CCl_3$, $SCHF_2$, $SCH_2F$, $SCHFCl$, $SCF_3$, $SCHCl_2$, $SCH_2Cl$ or $SCCl_3$. In some embodiments, $R^4$ is OH, $OCH_3$, $OCH_2CH_3$, $OCH_2CH_2CH_3$, $O(CH_2)3CH_3$, $O(CH_2)4CH_3$, $O(CH_2)5CH_3$, $OCHF_2$, $OCH_2F$, $OCHFCl$, $OCF_3$, $OCHCl_2$, $OCHFCl$, $CCl_3$, $SCHF_2$, $SCH_2F$, $SCHFCl$, $SCF_3$, $SCHCl_2$, $SCH_2Cl$ or $SCCl_3$. In some embodiments, $R^4$ is OH, $OCH_3$, $O(CH_2)5CH_3$, $OCHF_2$, $OCH_2F$, $OCHFCl$, $OCF_3$, $OCHCl_2$, $OCHFCl$, $OCCl_3$, $SCHF_2$ or $SCH_2F$. In some embodiments, $R^4$ is OH, $OCH_3$, or $OCHF_2$. In some embodiments, $R^4$ is $C_{1-6}$alkyleneCN, $C_{2-6}$alkenyleneCN, $C_{2-6}$alkynyleneCN, $C_{1-6}$alkyleneCONH$_2$, $C_{2-6}$alkenylene CONH$_2$ or $C_{2-6}$alkynyleneCONH$_2$. In some embodiments, $R^4$ is $C_{1-4}$alkyleneCN, $C_{2-4}$alkenyleneCN, $C_{1-4}$alkyleneCONH$_2$ or $C_{2-4}$alkenylene CONH$_2$. In some embodiments, $R^4$ is $C_{2-4}$alkenyleneCN or $C_{2-4}$alkenyleneCONH$_2$. In some embodiments, $R^4$ is Br, Cl or I. In some embodiments, $R^4$ is H.

In some embodiments, the compound of Formula (III) is selected from

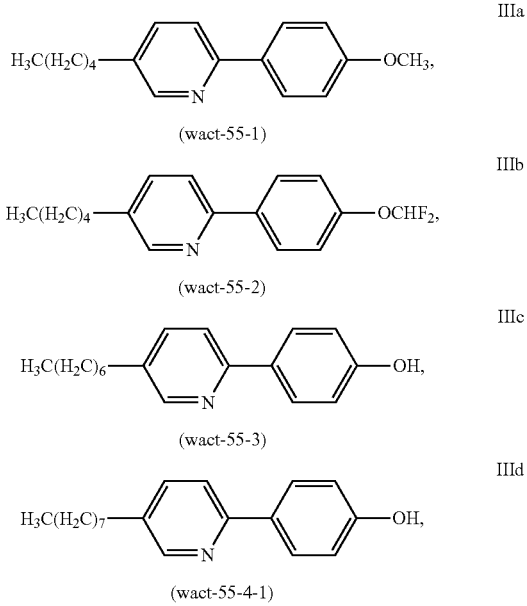

| | |
|---|---|
| ![IIIe] H₃C(H₂C)₄—pyridine—C₆H₄—CH=CH—CN (wact-55-5) | IIIe |
| ![IIIf] H₃C(H₂C)₆—pyridine—C₆H₃(F)—O(CH₂)₅CH₃ (wact-55-6) | IIIf |
| ![IIIg] H₃C(H₂C)₄—pyridine—C₆H₄—CH=CH—CONH₂ (wact-55-7) | IIIg |
| ![IIIh] H₃C(H₂C)₄—pyridine—C₆H₄—OCH₂CH₃ (wact-55-8) | IIIh |
| ![IIIi] H₃C(H₂C)₂—pyridine—C₆H₄—OCHF₂ (wact-55-12-1) | IIIi |
| ![IIIj] H₃C(H₂C)₆—pyridine—C₆H₄—OCH₃ (wact-55-10) | IIIj |
| ![IIIk] H₃C(H₂C)₅—pyridine—C₆H₄—OCH₃ (wact-55-11) | IIIk |
| ![IIIl] H₃C—pyridine—C₆H₄—OCH₃ | IIIl |
| ![IIIn] H₃C(H₂C)₆—pyridine—C₆H₄—OCHF₂ (wact-55-13) | IIIn |
| ![IIIo] H₃C(H₂C)₄—pyridine—C₆H₄—I (wact-55-14) | IIIo |
| ![IIIp] H₃C(H₂C)₄—pyridine—C₆H₄—Br (wact-55-15) | IIIp |
| ![IIIq] H₃C(H₂C)₇—pyrimidine—C₆H₄—OH (wact-55-16) | IIIq |
| ![IIIr] H₂N—pyrimidine—C₆H₄—(CH₂)₅(CH₃) (wact-55-17) | IIIr |
| ![IIIs] H₃C(H₂C)₃—pyrimidine—C₆H₄—Br (wact-55-18) | IIIs |
| ![IIIt] H₃C(H₂C)₇—pyridine—C₆H₃(F)—OH (wact-55-4-2) | IIIt |
| ![IIIu] H₃C(H₂C)₂—pyridine—C₆H₄—OCF₃ (wact-55-9) | IIIu |
| ![IIIv] H₃C(H₂C)₂—pyridine—C₆H₄—OCH₂Cl (wact-55-12-2) | IIIv |
| ![IIIw] H₃C(H₂C)₂—pyridine—C₆H₄—OCHFCl (wact-12-3) | IIIw |
| ![IIIx] H₃C(H₂C)₂—pyridine—C₆H₄—OCHCl₂ (wact-55-12-4) | IIIx |
| ![IIIy] H₃C(H₂C)₂—pyridine—C₆H₄—SCHF₂ (wact-55-12-5) | IIIy |
| ![IIIz] H₃C(H₂C)₂—C₆H₄—C₆H₄—OCHF₂ (wact-55-12-6) | IIIz |

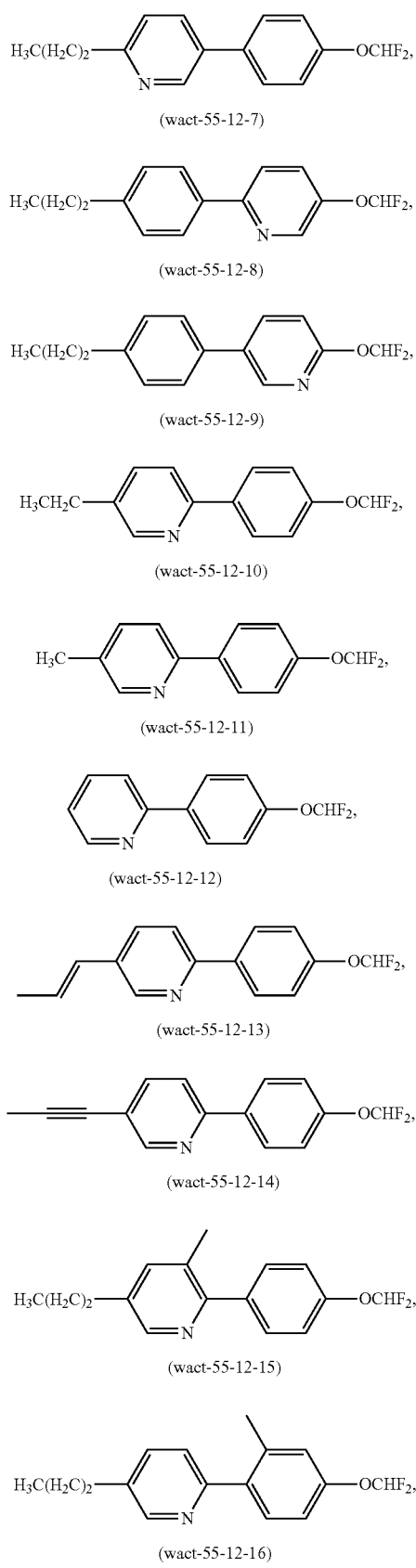
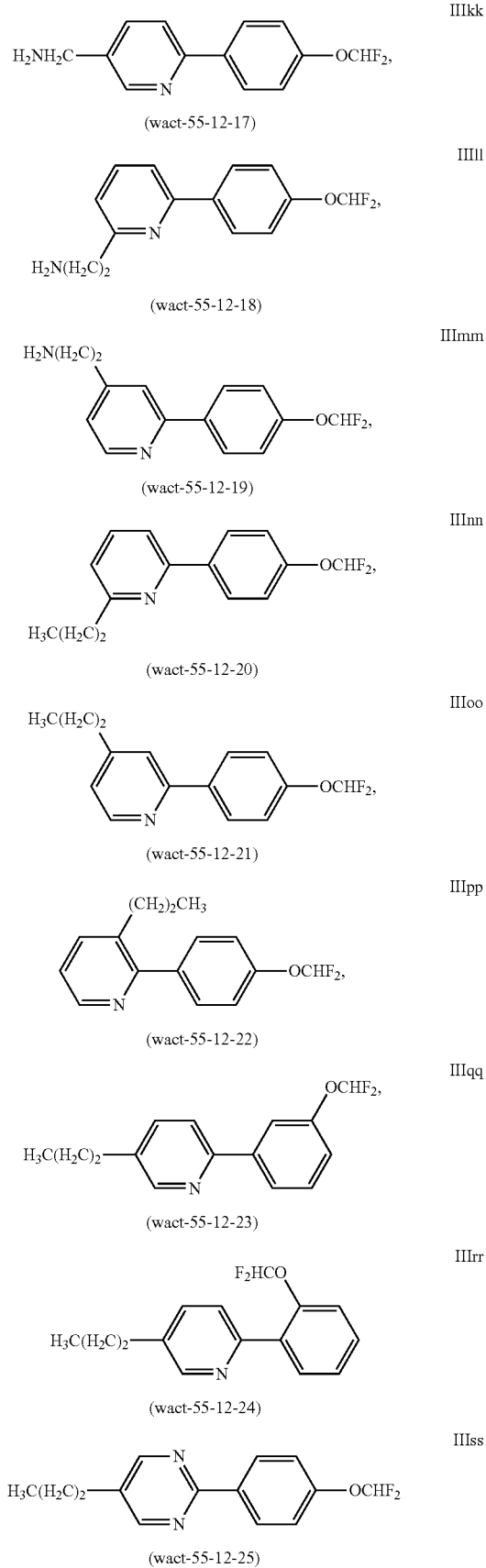

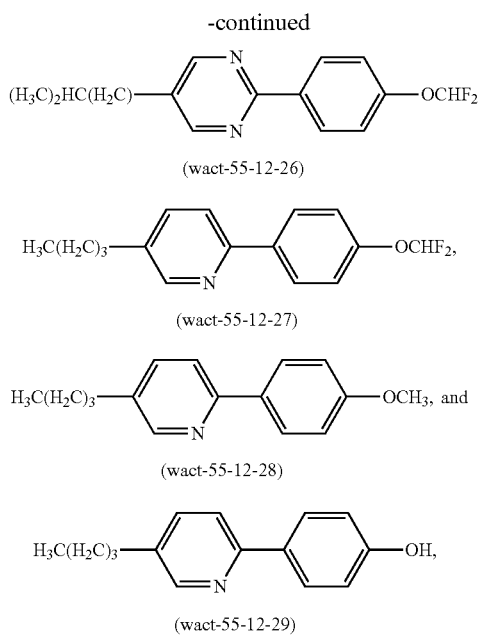

(wact-55-12-26), (wact-55-12-27), (wact-55-12-28), (wact-55-12-29)

or a pharmaceutically acceptable salt and/or solvate thereof.

In some embodiments, the nematode infection is an infection of a nematode of a species selected from *Cooperia oncophora, Haemonchus contortus, Caenorhabditis elegans, Pristionchus pacificus, Phasmarhabditis hermaphrodita, Necator americanis, Trichuris muris, Strongyloides ratti, Meloidogyne incognita* and *Meloidogyne chitwoodi.*

In some embodiments, the nematode infection is an infection of a nematode of a species selected from *Cooperia oncophora, Haemonchus contortus,* and *Caenorhabditis elegans.*

Treatment methods comprise administering to a subject one or more compounds of the application, and optionally consists of a single administration, or alternatively comprises a series of administrations. The length of the treatment period depends on a variety of factors, such as the severity of the infection, disease, disorder or condition, the age of the subject, the dosage of the one or more compounds of the application, the activity of one or more compounds of the application, or a combination thereof.

In an embodiment, the one or more compounds of the application are administered or used as soon as possible after exposure to the nematode. In an embodiment, the one or more compounds of the application are administered or used until treatment of the nematode infection, disease disorder or condition is achieved. For example, until complete elimination of the nematode is achieved, or until the number of nematode has been reduced to the point where the subject's defenses are no longer overwhelmed and can kill any remaining nematode.

In an embodiment, the methods of the present application comprise administering an effective amount of a compound or a composition of the application to a subject selected from humans, mammals, birds, vertebrates, plants, seeds, and soil.

In an embodiment, the uses of the present application of a compound or a composition of the application are in a subject selected from humans, mammals, birds, vertebrates, plants, seeds, and soil.

In some embodiments, the nematode infects plants and the nematicidal composition is administered to the soil or to plants. In some embodiments, the nematicidal composition is administered to soil before planting. In some embodiments, the nematicidal composition is administered to soil after planting. In some embodiments, the nematicidal composition is administered to soil using a drip system. In some embodiments, the nematicidal composition is administered to soil using a drench system. In some embodiments, the nematicidal composition is administered to plant roots or plant foliage (e.g., leaves, stems). In some embodiments the nematicide composition is tilled into the soil or administered in furrow. In some embodiments, the nematicidal composition is administered to seeds. In some embodiments, the nematode parasite infects a vertebrate. In some embodiments, the nematicidal composition is administered to non-human vertebrate. In some embodiments, the nematicidal composition is administered to a human. In some embodiments, the nematicidal composition is formulated as a drench to be administered to a non-human animal. In some embodiments, the nematicidal composition is formulated as an orally administered drug. In some embodiments, the nematicidal composition is formulated as an injectable drug. In some embodiments, the nematicidal composition is formulated for topical applications such as pour-ons, or for the use in tags or collars.

In some embodiments, the methods of the application comprise administering a compound or a composition of the application through one or more means selected from pre-planting, post-planting, as a feed additive, a drench, an external application, a pill and by injection.

In some embodiments, the present application includes methods of reducing the viability or fecundity or slowing the growth or development or inhibiting the infectivity of a nematode using a compound or a composition of the application as described herein.

In some embodiments, the present application includes methods of reducing the viability or fecundity or slowing the growth or development or inhibiting the infectivity of a nematode using a compound or a composition of the application as described herein, the methods comprising administering a compound or a composition of the application to subject selected from a human, a mammal, a bird, a vertebrate in general, a plant, a seed, or soil. In some examples, the bird can be a domesticated fowl; the mammal can be a domesticated animal and/or livestock.

The dosage of the one or more compounds of the application, varies depending on many factors such as the pharmacodynamic properties thereof, the mode of administration, the age, health and weight/mass of the subject, the nature and extent of the symptoms, the frequency of the treatment and the type of concurrent treatment, if any, and the clearance rate in the subject to be treated. One of skill in the art can determine the appropriate dosage based on the above factors. The one or more compounds of the application may be administered initially in a suitable dosage that may be adjusted as required, depending on the response.

Compounds can be tested for anthelmintic activity using methods known in the art. For example, the compound is combined with nematodes, e.g., in a well of microtiter dish, in liquid or solid media or in the soil containing the agent. Staged nematodes are placed on the media. The time of survival, viability of offspring, and/or the movement of the nematodes are measured. An agent with "anthelmintic or anthelminthic or antihelmthic activity" can, for example, reduce the survival time of adult nematodes relative to unexposed similarly staged adults, e.g., by about 20%, 40%, 60%, 80%, or more. In the alternative, an agent with "anthelmintic or anthelminthic or antihelminthic activity" may also cause the nematodes to cease replicating, regenerating, and/or producing viable progeny, e.g., by about 20%, 40%, 60%, 80%, or more. The effect may be apparent immediately or in successive generations.

III. Compositions of the Application

In some embodiments, the present application includes pharmaceutical compositions comprising a pharmaceutically acceptable carrier and one or more compounds of Formula (III)

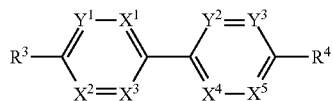
(III)

and/or a pharmaceutically acceptable salt and/or solvate thereof, wherein:

$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneN R$^5$R$^6$ or $C_{2-10}$alkynyleneN R$^5$R$^6$;

$R^4$ is H, OH, halo, $C_{1-10}$alkyl, $C_{2-10}$alkenyl, $C_{2-10}$alkynyl, $OC_{1-10}$alkyl, $OC_{1-10}$haloalkynl, $SC_{1-10}$alkyl or $SC_{1-10}$haloalkyl, the latter seven groups being unsubstituted or substituted with CN, or $C(O)NH_2$;

$X^1$, $X^2$, $X^3$, $X^4$ and $X^5$ are independently $CR^7$ or N;

$Y^1$, $Y^2$ and $Y^3$ are independently $CR^8$;

$R^5$ and $R^6$ are independently H or $C_{1-6}$alkyl;

$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and $R^9$ and $R^{10}$ are independently H or $C_{1-6}$alkyl.

In some embodiments, the present application includes pharmaceutical compositions comprising a pharmaceutically acceptable carrier and a compound of Formula (III)

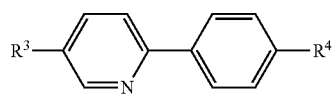
III and/or a pharmaceutically acceptable salt and/or solvate thereof, wherein:

$R^3$ is $C_{1-10}$alkyl; and $R^4$ is OH, halo, $OC_{1-10}$fluoroalkyl or $OC_{1-10}$alkyl, the latter group being unsubstituted or substituted with CN or $C(O)NH_2$; and wherein the compound of Formula (III) is present in an amount effective to treat a nematode infection in a subject in need thereof.

In some embodiments, the present application includes uses of pharmaceutical compositions comprising one or more compounds of Formula (III), or a pharmaceutically acceptable salt and/or solvate thereof, for treating or preventing a nematode infection or a disease, a disorder, or a condition arising from a nematode infection in a subject in need thereof.

In some embodiments, the present application includes a nematicidal composition comprising a carrier and one or more compounds of Formula (III)

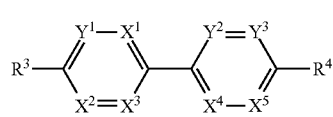
(III)

and/or a pharmaceutically acceptable salt and/or solvate thereof, wherein:

$R^3$ is H, $NR^5R^6$, $C_{2-10}$alkenyl, $C_{2-10}$alkynyl, $C_{1-10}$alkyleneNR$^5$R$^6$, $C_{2-10}$alkenyleneNR$^5$R$^6$ or $C_{2-10}$alkynyleneNR$^5$R$^6$;

$R^4$ is H, OH, halo, $C_{1-10}$alkyl, $C_{2-10}$alkenyl, $C_{2-10}$alkynyl, $OC_{1-10}$alkyl, $OC_{1-10}$haloalkynl, $SC_{1-10}$alkyl or $SC_{1-10}$haloalkyl, the latter seven groups being unsubstituted or substituted with CN, or $C(O)NH_2$;

$X^1$, $X^2$, $X^3$, $X^4$ and $X^5$ are independently $CR^7$ or N;

$Y^1$, $Y^2$ and $Y^3$ are independently $CR^8$;

$R^5$ and $R^6$ are independently H or $C_{1-6}$alkyl;

$R^7$ and $R^8$ are independently H, halo, $C_{1-10}$alkyl, $OC_{1-10}$alkyl or $OC_{1-10}$haloalkyl, the latter three groups being unsubstituted or substituted with $NR^9R^{10}$; and $R^9$ and $R^{10}$ are independently H or $C_{1-6}$alkyl.

In some embodiments, the present application includes a nematicidal composition comprising a carrier and a compound of Formula (III)

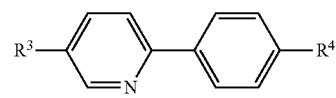
III and/or a salt and/or solvate thereof, wherein:

$R^3$ is $C_{1-10}$alkyl; and $R^4$ is OH, halo, $OC_{1-10}$fluoroalkyl or $OC_{1-10}$alkyl, the latter group being unsubstituted or substituted with CN or $C(O)NH_2$; and wherein the compound of Formula (III) is present in an amount effective to treat a nematode infection in a subject in need thereof.

In some embodiments, the compound of Formula (III) is selected from

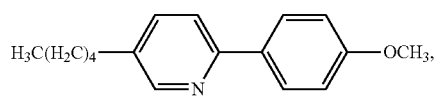
(wact-55-1)
IIIa

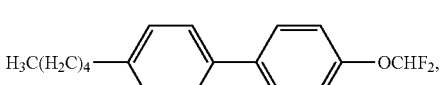
(wact-55-2)
IIIb

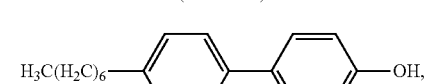
(wact-55-3)
IIIc

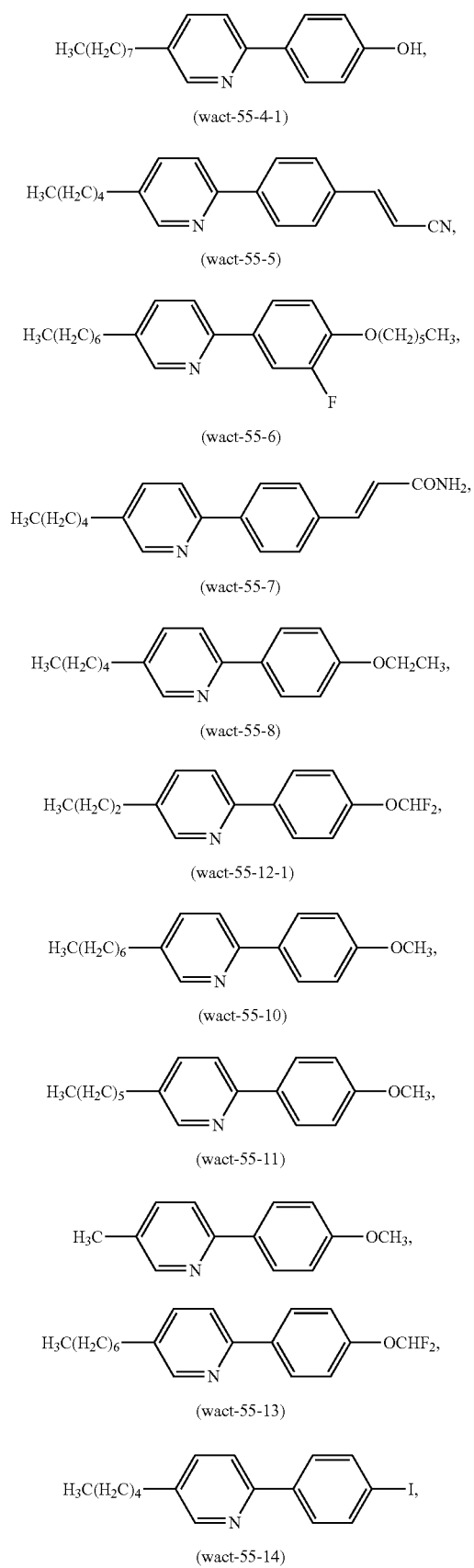
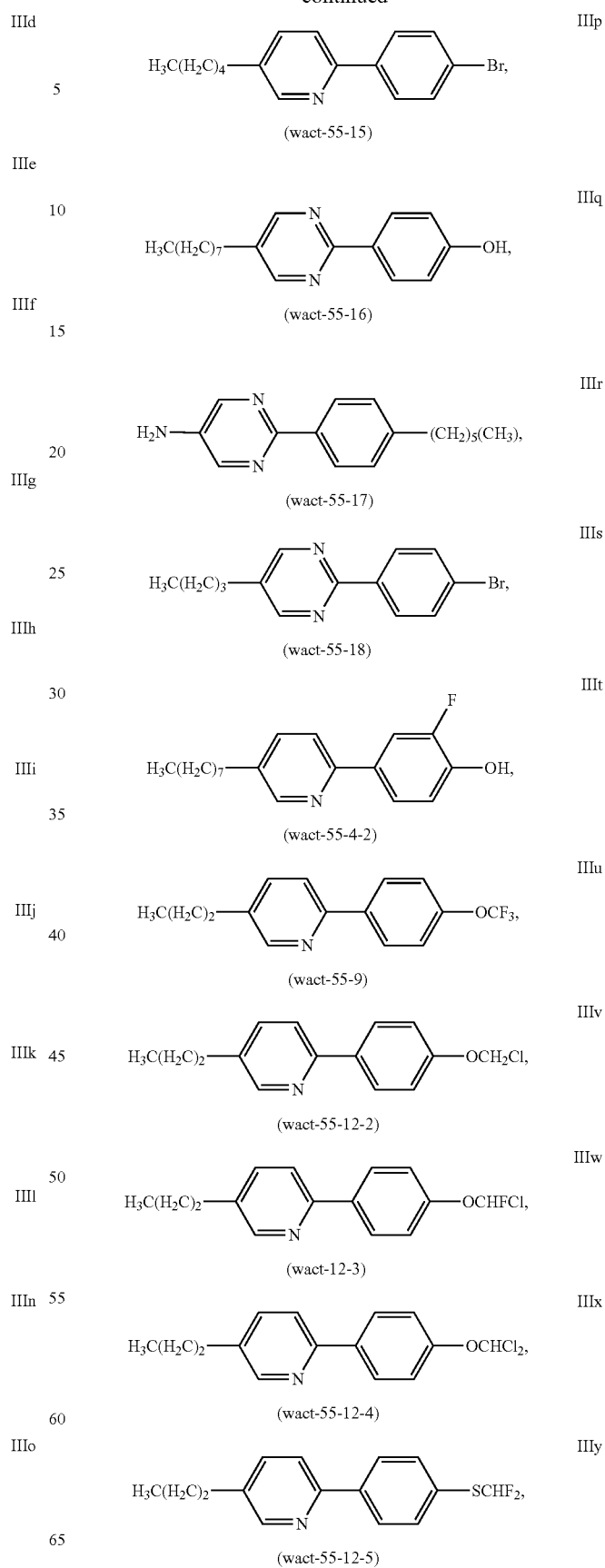

-continued
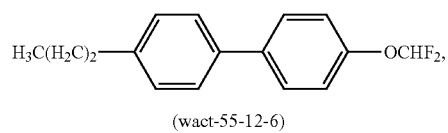
(wact-55-12-6) IIIz
(wact-55-12-7) IIIaa
structures continued:
- (wact-55-12-8) IIIbb
- (wact-55-12-9) IIIcc
- (wact-55-12-10) IIIdd
- (wact-55-12-11) IIIee
- (wact-55-12-12) IIIff
- (wact-55-12-13) IIIgg
- (wact-55-12-14) IIIhh
- (wact-55-12-15) IIIii
-continued
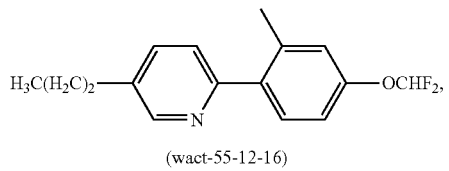
(wact-55-12-16) IIIjj
(wact-55-12-17) IIIkk
- (wact-55-12-18) IIIll
- (wact-55-12-19) IIImm
- (wact-55-12-20) IIInn
- (wact-55-12-21) IIIoo
- (wact-55-12-22) IIIpp
- (wact-55-12-23) IIIqq
- (wact-55-12-24) IIIrr

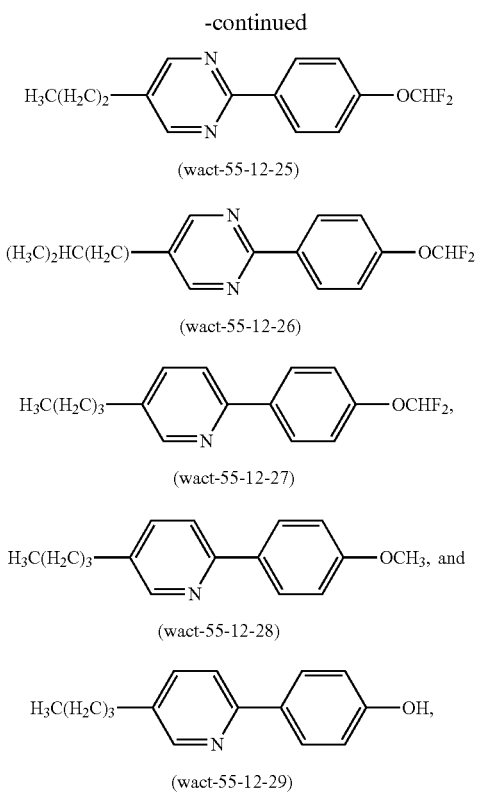

(wact-55-12-25)

(wact-55-12-26)

(wact-55-12-27)

(wact-55-12-28)

(wact-55-12-29)

and/or a pharmaceutically acceptable salt and/or solvate thereof.

In some embodiments, the nematode infection is an infection of a nematode of the following non-limiting, exemplary genera: *Caenorhabditis, Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera*, other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus, Paratrichodorus, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongy hides, Strongylus, Thelazia, Toxascaris, Toxocara, Trichinella, Trichostrongylus, Trichuris, Uncinaria* or *Wuchereria*. In some embodiments, the nematodes are of the genera *Cooperia, Haemonchus, Caenorhabditis, Onchocerca, Brugia, Acanthocheilonema, Dipetalonema, Loa, Mansonella, Parafilaria, Setaria, Stephanofilaria, Wucheria, Pratylenchus, Heterodera, Meloidogyne* or *Paratylenchus*. In some embodiments the nemotodes are of the species *Cooperia oncophora, Haemonchus contortus, Caenorhabditis elegans, Ancylostoma caninum, Haemonchus contortus, Trichinella spiralis, Trichurs muris, Ascaris suum, Toxocara canis, Toxocara cati, Strongyloides ratti, Parastrongyloides trichosuri, Heterodera glycines, Globodera pallida, Meloidogyne javanica, Meloidogyne incognita, Meloidogyne arenaria, Radopholus similis, Longidorus elongatus, Meloidogyne hapla* or *Pratylenchus penetrans*.

In some embodiments, the nematode infection is an infection of a nematode of a species selected from *Cooperia oncophora, Haemonchus contortus, Caenorhabditis elegans Pristionchus pacificus, Phasmarhabditis hermaphrodita, Necator americanis, Trichuris muris, Strongyloides ratti, Meloidogyne incognita* and *Meloidogyne chitwoodi*.

In some embodiments, the nematode infection is an infection of a nematode of a species selected from *Cooperia oncophora, Haemonchus contortus* and *Caenorhabditis elegans*.

In some embodiments, the subject is selected from humans, mammals, birds, vertebrates, plants, seeds, and soil.

In some embodiments, the nematicidal compositions further comprise one or more agricultural excipients.

In some embodiments, the nematicidal compositions further comprise one or more agriculturally acceptable excipients.

For example, in some embodiments, the nematicidal compositions further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15, and mixtures therof.

In some embodiments, the nematicidal composition further comprises a permeation enhancer (e.g., cyclodextrin). In some embodiments, the nematicidal composition further comprises a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil), or mixtures thereof. In some embodiments, the nematicidal composition further comprises another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al, or mixtures thereof. Useful fungicides include, but are not limited to, silthiofam, fludioxonil, myclobutanil, azoxystrobin, chlorothalonil, propiconazole, tebuconazole and pyraclostrobin, or mixtures thereof. In some embodiments, the nematicidal composition may also comprise herbicides (e.g., trifloxysulfuron, glyphosate, halosulfuron) and other chemicals for disease control (e.g., chitosan).

In some embodiments, the application also includes a nematicidal feed for a non-human vertebrate including:

(a) a feed; and (b) a nematicidal composition, of the application.

In some embodiments, the feed is selected from: soy, wheat, corn, sorghum, millet, alfalfa, clover, and rye, and mixtures thereof. Also described are feeds that have been supplemented to include one or more of the compounds of the application. A nematicidal feed for a non-human vertebrate can comprise: (a) an animal feed; and (b) an effective amount of a nematicidal compound of the application.

In some embodiments, the pharmaceutical compositions further comprise one or more pharmaceutically acceptable excipients. Conventional procedures and ingredients for the selection and preparation of suitable pharmaceutical compositions are described, for example, in Remington's Pharmaceutical Sciences (2000-20th edition) and in The United States Pharmacopeia: The National Formulary (USP 24 NF$_{19}$) published in 1999.

For example, the pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

In an embodiment, parenteral administration is by continuous infusion over a selected period of time. Solutions suitable for parenteral administration are prepared by known methods by a person skilled in the art. For example, the compounds of the application are prepared in water optionally mixed with a surfactant such as hydroxypropylcellulose. Dispersions are also prepared in glycerol, liquid polyethylene glycols, DMSO and mixtures thereof with or without alcohol, and in oils. Under ordinary conditions of storage and use, these preparations contain a preservative to prevent the growth of microorganisms.

Compositions for nasal administration are conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which take the form of a cartridge or refill for use with an atomising device. Alternatively, the sealed container is a unitary dispensing device such as a single dose nasal inhaler or an aerosol dispenser fitted with a metering valve, which is intended for disposal after use. Where the dosage form comprises an aerosol dispenser, it contains a propellant, which is, for example, a compressed gas such as compressed air or an organic propellant such as fluorochlorohydrocarbon. In an embodiment, the aerosol dosage forms take the form of a pump-atomizer.

Compositions suitable for buccal or sublingual administration include tablets, lozenges, and pastilles, wherein the active ingredient is formulated with a carrier such as sugar, acacia, tragacanth, gelatin and/or glycerine. Compositions for rectal administration are conveniently in the form of suppositories containing a conventional suppository base such as cocoa butter.

In another embodiment, compounds of the application are orally administered, for example, with an inert diluent or with an assimilable edible carrier, or they are enclosed in hard or soft shell gelatin capsules, or they are compressed into tablets, or they are incorporated directly with the food of a diet. For oral administration, the compounds of the application may be incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In an embodiment, timed-release compositions are, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of lipids, such as cholesterol, stearylamine or phosphatidylcholines.

It is also possible to freeze-dry the compounds of the application and use the lyophilizate obtained, for example, for the preparation of products for injection.

The compounds of the application are either commercially available or may be prepared using methods known in the art.

The formation of a desired compound salt is achieved using standard techniques. For example, the neutral compound is treated with an acid or base in a suitable solvent and the formed salt is isolated by filtration, extraction or any other suitable method. A person skilled in the art would know that salts can only be formed with compounds having basic and/or acidic functional groups, such as a basic nitrogen or an acid amide.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

IV. Compounds of the Application

A family of novel small molecule compounds have been prepared and found to incapacitate parasitic nematodes, and advantageously show no evidence of genetic resistance. Accordingly, the present application includes one or more compounds of Formula (III-A)

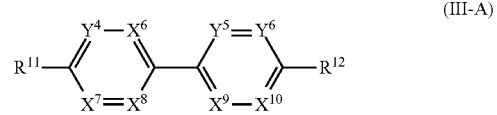

(III-A)

or a pharmaceutically acceptable salt and/or solvate thereof, wherein:

$R^{11}$ is H, $C_{1-4}$alkyl, $C_{2-10}$alkenyl, $C_{2-10}$alkynyl, $C_{1-10}$alkyleneNR$^{13}$R$^{14}$, $C_{2-10}$alkenyleneNR$^{13}$R$^{14}$ or $C_{2-10}$alkynyleneNR$^{13}$R$^{14}$;

$R^{12}$ is H, OH, $C_{1-8}$alkyl, $C_{2-10}$alkenyl, $C_{2-10}$alkynyl, $OC_{1-6}$alkyl, $C_{2-10}$alkenyl, $OC_{2-10}$alkynyl, $OC_{1-10}$haloalkyl, $SC_{1-10}$alkyl or $SC_{1-10}$haloalkyl;

$X^6$, $X^7$, $X^8$, $X^9$ and $X^{10}$ are independently $CR^{15}$ or N;

$Y^4$, $Y^5$ and $Y^6$ are independently $CR^{16}$;

$R^{13}$ and $R^{14}$ are independently H or $C_{1-6}$alkyl;

$R^{15}$ and $R^{16}$ are independently H, halo, $C_{1-6}$alkyl, $C_{1-6}$haloalkyl, $OC_{1-10}$alkyl or $OC_{1-6}$haloalkyl the latter four groups being unsubstituted or substituted with $NR^{17}R^{18}$; and $R^{17}$ and $R^{18}$ are independently H or $C_{1-6}$alkyl; provided the compound is not 2-(4-(trifluoromethoxy)phenyl)-5-propylpyridine or 2-(4-(difluoromethoxy)phenyl)-5-propylpyridine.

In some embodiments, one of $X^6$, $X^7$, $X^8$, $X^9$ and $X^{10}$ is N and the others are independently $CR^{15}$. In some embodiments $X^8$ is N and $X^6$, $X^7$, $X^9$ and $X^{10}$ are independently $CR^{15}$. In some embodiments $X^7$ is N and $X^6$, $X^8$, $X^9$ and $X^{10}$ are independently $CR^{15}$. In some embodiments $X^9$ is N and $X^6$, $X^7$, $X^8$ and $X^{10}$ are independently $CR^{15}$. In some embodiments $X^1$ is N and $X^6$, $X^7$, $X^8$ and $X^9$ are independently $CR^{15}$. In some embodiments, $X^6$ and $X^8$ are both N and $X^7$, $X^9$ and $X^{10}$ are independently $CR^{15}$.

In some embodiments, $R^{15}$ and $R^{16}$ are independently H, F, Cl, $C_{1-6}$alkyl, $OC_{1-6}$alkyl or $OC_{1-6}$haloalkyl, the latter three groups being unsubstituted or substituted with $NR^{17}R^{18}$. In some embodiments, $R^{15}$ and $R^{16}$ are independently H, F, Cl, $C_{1-4}$alkyl, $OC_{1-4}$alkyl, $OC_{1-4}$fluoroalkyl or $C_{1-4}$alkylNR$^{17}R^{18}$. In some embodiments, $R^{17}$ and $R^{18}$ are independently H or $C_{1-4}$alkyl. In some embodiments, $R^{17}$ and $R^{18}$ are both H. In some embodiments, one of $R^{17}$ and $R^{18}$ is H and the other is $CH_3$ or $CH_2CH_3$. In some embodiments, $R^{17}$ and $R^{18}$ are both $CH_3$.

In some embodiments, $R^{15}$ and $R^{16}$ are independently H, F, Cl, $CH_3$, $CH_2CH_3$, $CH_2CH_2CH_3$, $CH_2CH_2CH_2CH_3$, $CH_2NH_2$, $CH_2CH_2NH_2$, $CH_2CH_2CH_2NH_2$, $OCH_3$, $OCHF_2$, $OCH_2F$, $OCHFCl$, $OCF_3$, $OCHCl_2$, $OCH_2Cl$ or $OCCl_3$. In some embodiments, $R^{15}$ and $R^{16}$ are independently H, F, $CH_3$, $CH_2CH_3$, $CH_2CH_2CH_3$, $CH_2NH_2$, $CH_2CH_2NH_2$, $OCH_3$, $OCHF_2$, $OCH_2F$, $OCHFCl$, $OCF_3$, $OCHCl_2$, $OCH_2Cl$ or $OCCl_3$. In some embodiments, $R^{15}$ and $R^{16}$ are independently H, F, $CH_3$, $CH_2CH_3$, $CH_2CH_2CH_3$, $CH_2NH_2$, $CH_2CH_2NH_2$, $OCHF_2$ or $OCH_2F$.

In some embodiments, $R^{11}$ is H, $C_{1-4}$alkyl, $C_{2-6}$alkenyl, $C_{2-6}$alkynyl, $C_{1-6}$alkyleneNR$^{13}R^{14}$, $C_{2-6}$alkenyleneNR$^{13}R^{14}$ or $C_{2-6}$alkynyleneNR$^{13}R^{14}$. In some embodiments, $R^{13}$ and $R^{14}$ are independently H or $C_{1-4}$alkyl. In some embodiments, $R^{13}$ and $R^{14}$ are both H. In some embodiments, one of $R^{13}$ and $R^{14}$ is H and the other is $CH_3$ or $CH_2CH_3$. In some embodiments, $R^{13}$ and $R^{14}$ are both $CH_3$.

In some embodiments, $R^{11}$ is H, $C_{1-4}$alkyl, $C_{2-4}$alkenyl, $C_{2-4}$alkynyl, $C_{1-4}$alkyleneNH$_2$. In some embodiments, $R^{11}$ is $C_{1-3}$alkyleneNH$_2$. In some embodiments, $R^{11}$ is $C_{1-4}$alkyl, $C_{2-4}$alkenyl or $C_{2-4}$alkynyl. In some embodiments, $C_{2-4}$alkynyl is -CECCH$_3$. In some embodiments, $R^{11}$ is $C_{1-4}$alkyl. In some embodiments, $R^{11}$ is straight chain $C_{1-4}$alkyl. In some embodiments, $R^{11}$ is branched $C_{1-4}$alkyl. In some embodiments, $R^{11}$ is H.

In some embodiments, $R^{12}$ is H, OH, $C_{1-6}$alkyl, $C_{2-6}$alkenyl, $C_{2-6}$alkynyl, $OC_{1-6}$alkyl, $OC_{1-6}$haloalkyl, $SC_{1-6}$alkyl or $SC_{1-6}$haloalkyl. In some embodiments, $R^{12}$ is $C_{1-6}$alkyl, $C_{2-6}$alkenyl, $C_{2-6}$alkynyl, $OC_{1-6}$chloroalkyl, $OC_{1-6}$fluoroalkyl, 6chloroalkyl, $SC_{1-6}$fluoroalkyl or $OC_{1-6}$chlorofluoroalkyl. In some embodiments, $R^{12}$ is 4alkyl, $C_{2-4}$alkenyl, or $C_{2-4}$alkynyl. In some embodiments, $R^{12}$ is OH, $OC_{1-6}$alkyl, 4chloroalkyl, $OC_{1-4}$fluorooalkyl, $SC_{1-4}$fluoroalkyl or $OC_{1-4}$chlorofluoroalkyl. In some embodiments, $R^{12}$ is OH, $OCH_3$, $OCHF_2$, $OCH_2F$, $OCHFCl$, $OCF_3$, $OCHCl_2$, $OCH_2Cl$, $OCCl_3$, $SCF_3$, $SCHF_2$ or $SCH_2F$. In some embodiments, $R^{12}$ is OH, $OCH_3$, $OCHF_2$, $OCHFCl$, $OCHCl_2$, $OCH_2Cl$ or $SCHF_2$. In some embodiments, $R^{12}$ is H.

In some embodiments, the compound of Formula (III-A) is selected from

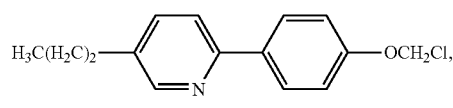

(wact-55-12-2)

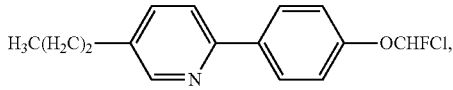

(wact-12-3)

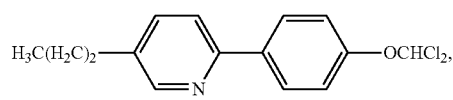

(wact-55-12-4)

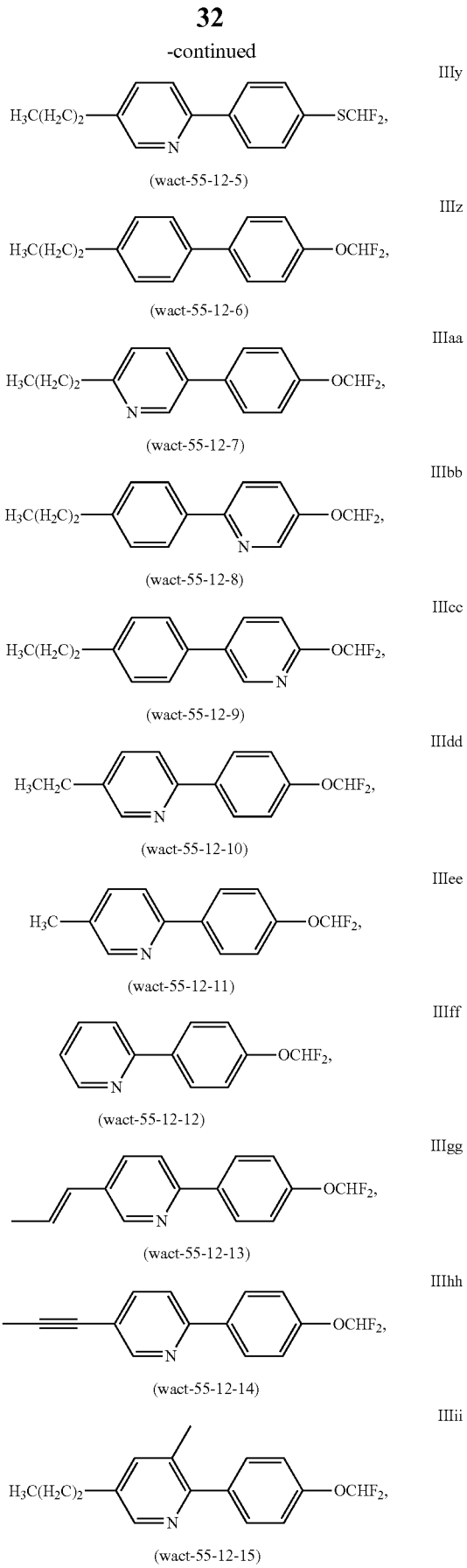

(wact-55-12-5)

(wact-55-12-6)

(wact-55-12-7)

(wact-55-12-8)

(wact-55-12-9)

(wact-55-12-10)

(wact-55-12-11)

(wact-55-12-12)

(wact-55-12-13)

(wact-55-12-14)

(wact-55-12-15)

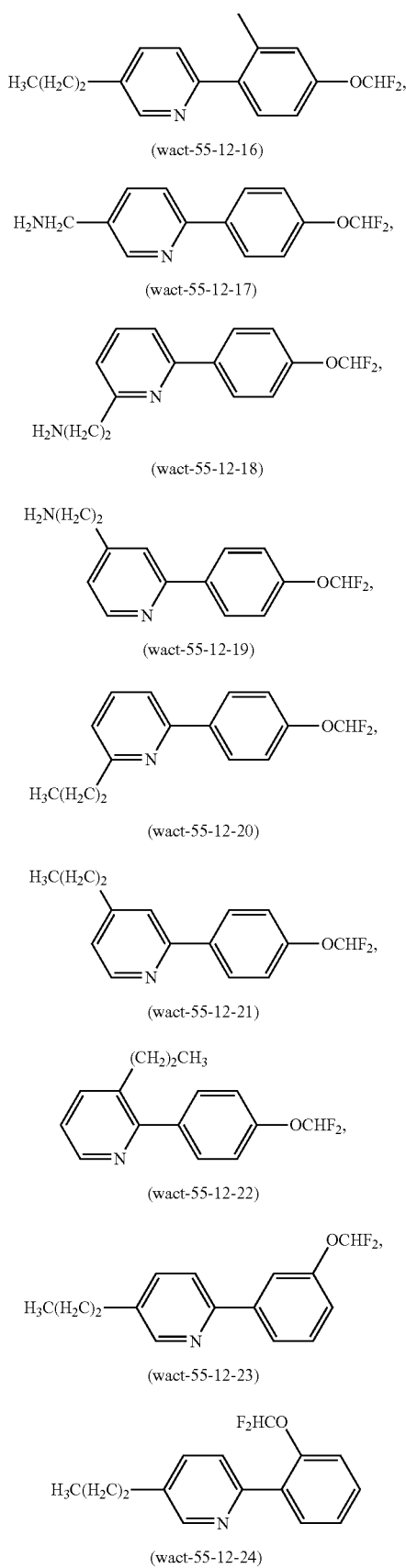
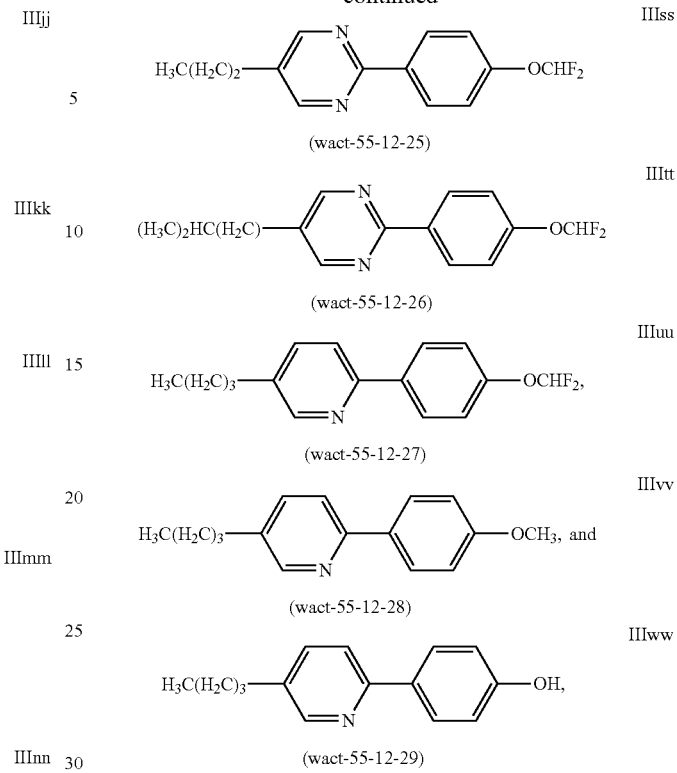

or a pharmaceutically acceptable salt and/or solvate thereof.

In an embodiment, the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art.

Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

V. Methods of Preparing the Compounds of the Application

Compounds of the present application can be prepared by various synthetic processes. The choice of particular structural features and/or substituents may influence the selection of one process over another. The selection of a particular process to prepare a given compound of the application is within the purview of the person of skill in the art. Some starting materials for preparing compounds of the present application are available from commercial chemical sources. Other starting materials, for example as described below, are readily prepared from available precursors using straightforward transformations that are well known in the art. In the Schemes below showing the preparation of compounds of the application, all variables are as defined in Formula (III), unless otherwise stated.

Compounds of Formula (III) or salts and/or solvates thereof, useful in the present application are available from commercial chemical sources or are prepared using methods known in the art.

For example, in some embodiments, compounds of Formula (III) wherein $R^3$ is $C_{1-10}$alkyl or $C_{2-10}$alkenylene are prepared as shown in Scheme 1. Therefore, an aldehyde compound of Formula A wherein L is a leaving group such as a halide (e.g. bromine) is converted to the alkenylene compound of Formula C wherein Alk" is alkyl or alkylenyl by coupling with a suitable phosphonium salt compound of Formula B wherein Alk' is alkyl or alkylenyl and Alk" is one C unit shorter than Alk' under, for example Wittig reaction conditions such as in the presence of a strong base (e.g potassium t-butoxide (KOtBu)) in a suitable solvent (e.g tetrahydrofuran (THF)). The compound of Formula C is then coupled, for example, using a Suzuki cross coupling reaction, with an boronic acid compound of Formula D in the presence of a suitable palladium catalyst (e.g., Pd(OAc)$_2$) and organic base (e.g., diisopropylamine (iPr$_2$NH)) to provide an alkenylene compound of Formula (III) which is optionally reduced to the corresponding alkyl compound of Formula (III) by methods known in the art, for example, catalytic hydrogenation in the presence of a palladium catalyst.

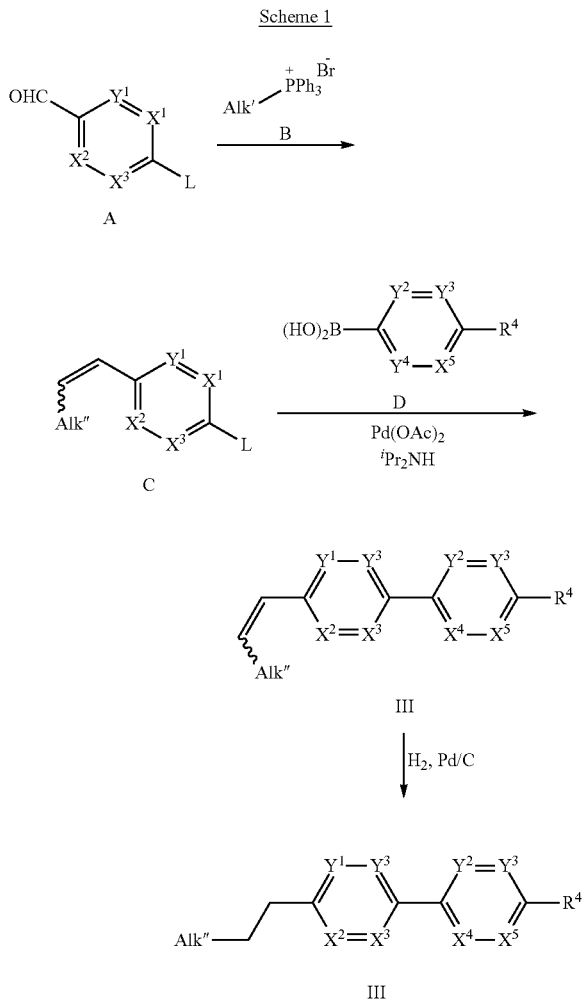

In some embodiments, the compounds of Formula (III) wherein $R^3$ is $OC_{1-10}$alkyl or $OC_{1-10}$haloalkyl and $X^4$ is N are prepared as shown in Scheme 2. Therefore, a compound of Formula E wherein L' is a leaving group (e.g., bromine) is reacted with a phosphonate compound of Formula F wherein L" is a leaving group and Alk''' is an alkyl group or haloalkyl group to provide the ether compound of Formula G. The compound of Formula G is then coupled with a boronic acid compound of Formula D' to provide a compound of Formula (III) as per Scheme 2.

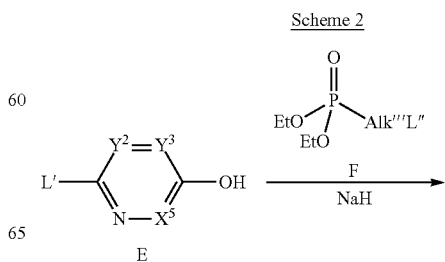

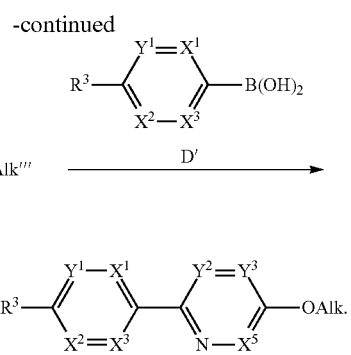

In some embodiments, the compounds of Formula (III) wherein $R^3$ is $OC_{1-10}$alkyl or $OC_{1-10}$haloalkyl and $X^5$ is N are prepared as shown in Scheme 3. Therefore, a compound of Formula H wherein L''' is a leaving group (e.g., bromine) is reacted with a sulfonylacetic acid compound of Formula J wherein Alc is an alkyl group or haloalkyl group to provide the ether compound of Formula K. The compound of Formula K is then coupled with a boronic acid compound of Formula D' to provide a compound of Formula (III) as per Scheme 3.

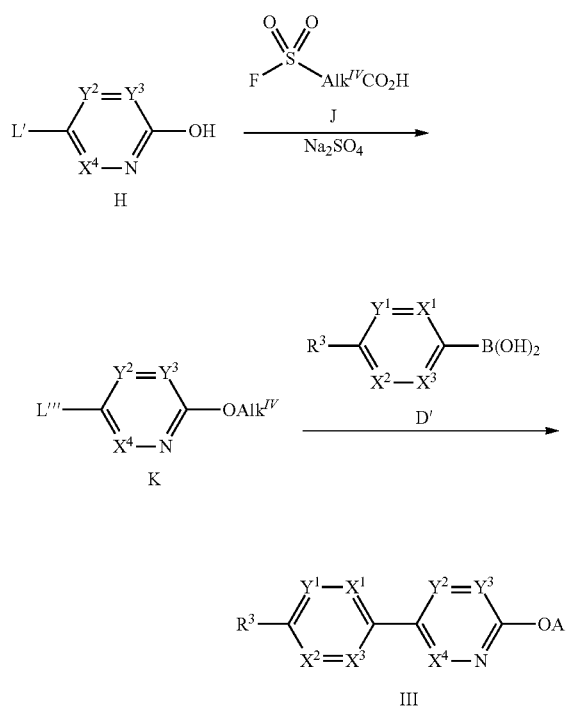

In some embodiments, the compounds of Formula (III) wherein $R^3$ is $C_{2-10}$alkynyl are prepared as shown in Scheme 4. Therefore, a compound of Formula O is prepared by reacting a compound of Formula M wherein $L^{IV}$ and $L^V$ are different leaving groups (e.g., iodine and bromine respectively) with a protected alkynyl compound, for example a triisopropylsilylether (TIPS) alkynyl compound of Formula N. The compound of Formula O is then coupled with a boronic acid compound of Formula D to provide a compound of Formula P as per Scheme 4. The compound of Formula P is deprotected with a suitable reagent (e.g., tetra-n-butylammonium fluoride, TBAF) to provide an alkynyl compound of Formula (III).

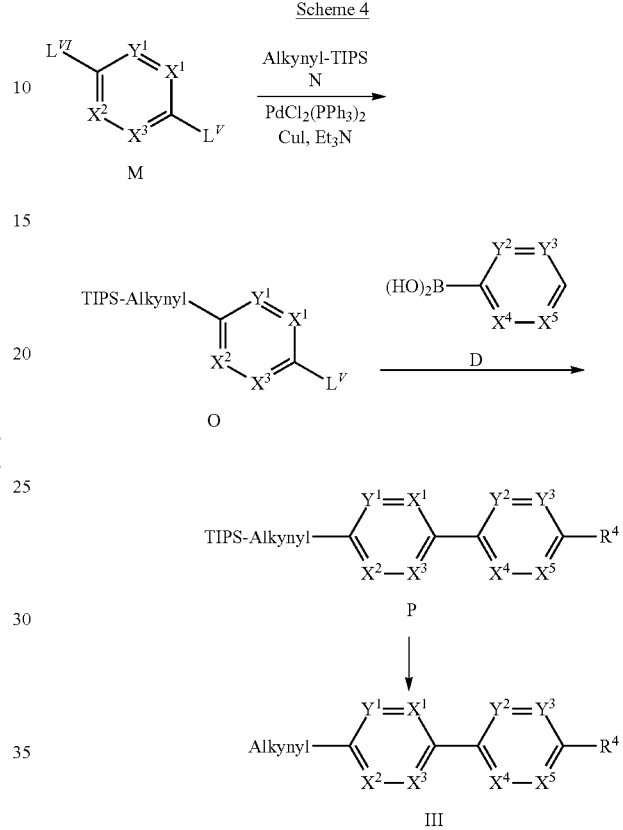

It would be appreciated by a person of skill in the art that when the alkynyl group comprises a terminal alkyne, the alkynyl compound of Formula (III) can be optionally further reacted with a suitable alkylhalide (e.g. methyl iodide) in the presence of a suitable base (e.g., butyl lithium) in a suitable solvent (e.g., THF) to increase the length of the alkynyl group.

In some embodiments, the compounds of Formula (III) wherein $R^3$ is $C_{1-10}$alkyleneNR$^5$R$^6$, $C_{2-10}$alkenyleneNR$^5$R$^6$ or $C_{2-10}$alkynyleneNR$^5$R$^6$ are prepared as shown in Scheme 5. Therefore, a compound of Formula R wherein P is a protecting group (e.g. tert-butyldimethylsilyl (TBS)), Alk$^V$ is $C_{1-10}$alkylene, $C_{2-10}$alkenylene or $C_{2-10}$alkynylene and $L^{VI}$ is a leaving group (e.g., bromine) is prepared from the corresponding alcohol compound of Formula Q by methods that are routine in the art. The compound of Formula R is then coupled with a boronic acid compound of Formula D to provide a compound of Formula S as per Scheme 5. The compound of Formula S is deprotected with a suitable reagent (e.g., tetra-n-butylammonium fluoride, TBAF) and converted to the corresponding bromine compound of Formula T in the presence of a suitable brominating reagent (e.g., N-Bromosuccinimide, NBS). The compound of Formula T is subsequently converted to the amino compound of Formula (III) using methods known in the art, for example the Gabriel synthesis of amines employing phthalimide potassium and hydrazine.

Scheme 5

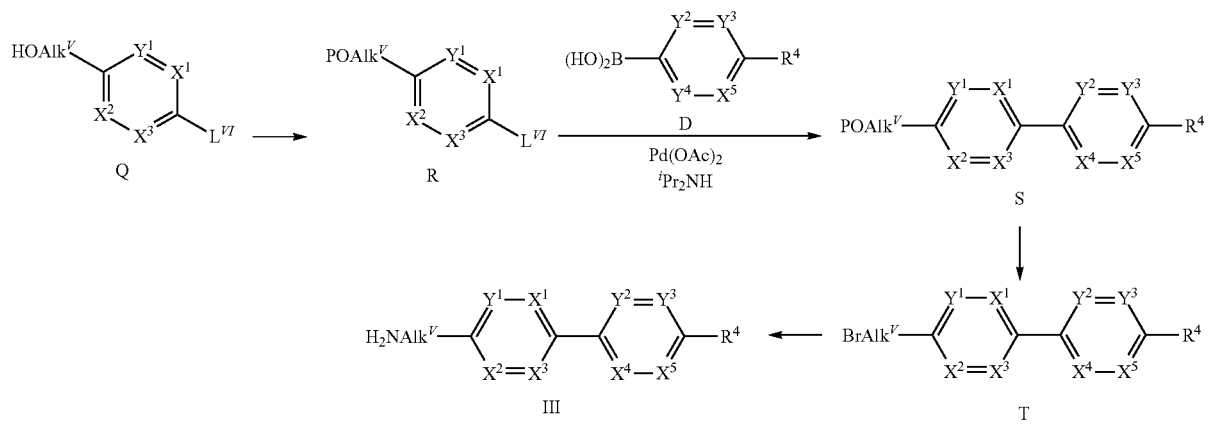

In some embodiments, the compound of Formula Q wherein Alk$^V$ is methylene is obtained by the reduction of the corresponding aldehyde compound of Formula A using methods routine in the art, for example, in the presence of sodium borohydride.

The formation of a desired compound salt is achieved using standard techniques. For example, the neutral compound is treated with an acid or base in a suitable solvent and the formed salt is isolated by filtration, extraction or any other suitable method. A person skilled in the art would know that salts can only be formed with compounds having basic and/or acidic functional groups, such as a basic nitrogen or an acid amide.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

The following non-limiting examples are illustrative of the present application. As is apparent to those skilled in the art, many of the details of the examples may be changed while still practicing the methods, compositions and kits described herein.

EXAMPLES

General Synthetic Methods
a) General Procedure A—Wittig reaction

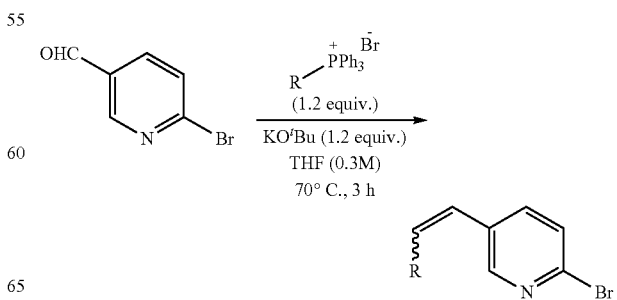

The phosphonium salt (1.2 equiv.) was first dissolved in tetrahydrofuran (THF) (0.3 M). KOtBu (1.2 equiv.) was then added and the mixture was stirred at room temperature for 30 minutes. The pyridinecarboxaldehyde (1 equiv.) was then added in three portions and the reaction was refluxed at 70° C. for 3 hours. The mixture was then allowed to cool to room temperature and was filtered through a Celite® pad eluting with pentanes. The filtrate was concentrated in vacuo and the product (mixture of isomers) was purified by flash column chromatography, eluting with a mixture of EtOAc:pentanes.

b) General Procedure B—Suzuki Reaction (Liu, C.; Zhang, Y.; Liu, N.; Qiu, J. Green Chem. 2012, 14, 2999-3003.)

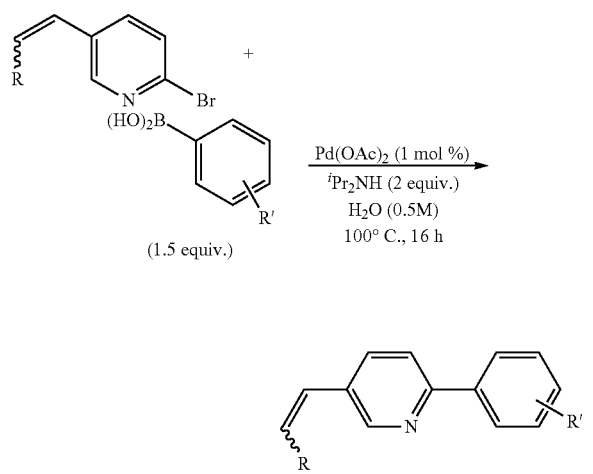

Substituted aryl boronic acid (1.5 equiv.) and Pd(OAc)$_2$ (1 mol %) were added to a mixture of the substituted bromopyridine (1 equiv.) in water (0.5 M). iPr$_2$NH (2 equiv.) was then added and the reaction was refluxed at 100° C. for 16 hours. The mixture was allowed to cool to room temperature and brine was added. The aqueous phase was extracted with ethyl acetate. The combined organics was washed with brine, dried with MgSO$_4$, and concentrated in vacuo. The product was purified by flash column chromatography, eluting with a mixture of EtOAc:pentanes.

c) General Procedure C—Hydrogenation

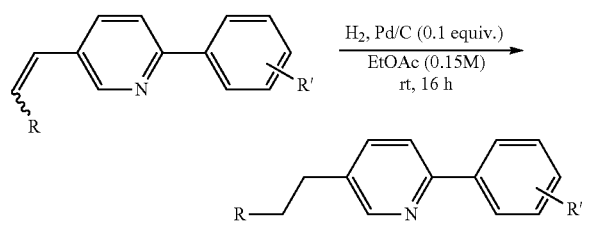

The vinylbiarene was dissolved in EtOAc (0.15 M). Pd/C (3% Pd, total 10 mol % Pd used) was added. Three cycles of evacuation and backfill with argon, followed by H$_2$ from a balloon was carried out. The reaction was stirred at room temperature under a H$_2$ atmosphere (balloon) for 16 hours. The contents of the flask were filtered over a Celite® pad eluting with EtOAc and concentrated in vacuo. The product was purified by flash column chromatography, eluting with a mixture of EtOAc:pentanes.

Example 1: 2-(4-((difluoromethyl)thio)phenyl)-5-propylpyridine [IIIy (wact-55-12-5)]

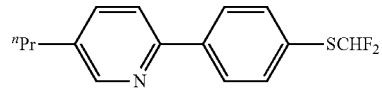

2-(4-((difluoromethyl)thio)phenyl)-5-propylpyridine was synthesized according to General Procedure A, B, and C using 6-bromonicotinaldehyde, ethyltriphenylphosphonium bromide, and (4-((difluoromethyl)thio)phenyl)boronic acid with an overall yield of 21%.

Example 2: 4-(difluoromethoxy)-4'-propyl-1,1'-biphenyl [IIIz (wact-55-12-6)]

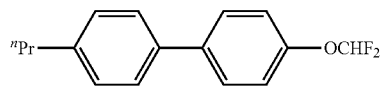

4-(difluoromethoxy)-4'-propyl-1,1'-biphenyl was synthesized according to General Procedure A, B, and C using 4-bromobenzaldehyde, ethyltriphenylphosphonium bromide, and (4-(difluoromethoxy)phenyl)boronic acid.

Example 3: 5-(4-(difluoromethoxy)phenyl)-2-propylpyridine [IIIaa (wact-55-12-7)]

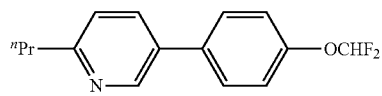

5-(4-(difluoromethoxy)phenyl)-2-propylpyridine was synthesized according to General Procedure A, B, and C using 5-bromopicolinaldehyde, ethyltriphenylphosphonium bromide, and (4-(difluoromethoxy)phenyl)boronic acid with an overall yield of 16%.

Example 4: 5-(difluoromethoxy)-2-(4-propylphenyl)pyridine [IIIbb (wact-55-12-8)]

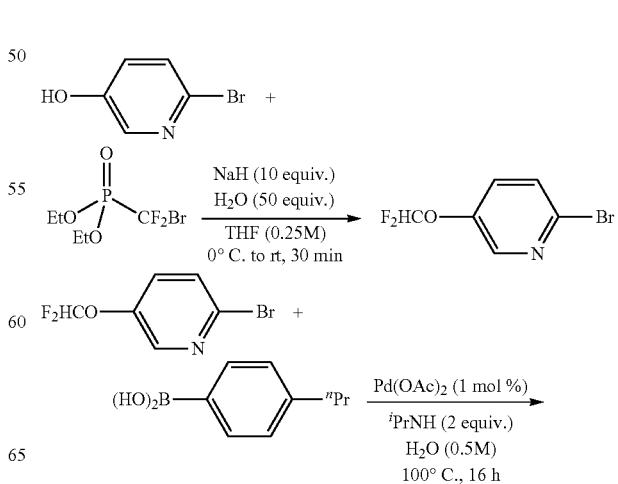

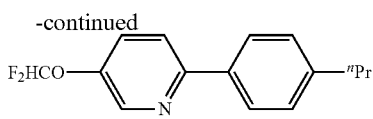

2-bromo-5-(difluoromethoxy)pyridine: The procedure was adapted from Wu and Wu et al. (Geng, Y.; Zhu, M.; Liang, A.; Niu, C.; Li, J.; Zou, D.; Wu, Y.; Wu, Y. Org. Biomol. Chem. 2018, 16, 1807-1811) 6-bromopyridin-3-ol (348 mg, 2 mmol, 1 equiv.) was dissolved in THF (8 mL, 0.25 M) and cooled to 0° C. NaH (800 mg, 20 mmol, 60%, 10 equiv.) was added and the mixture was stirred at 0° C. for 30 minutes. H₂O (1.80 mL, 100 mmol, 50 equiv.) was added dropwise and the mixture was stirred at 0° C. for 10 minutes. Diethyl (bromodifluoromethyl)phosphonate (0.71 mL, 4 mmol, 2 equiv.) was added and the reaction was allowed to stir from 0° C. to room temperature for 30 minutes. H₂O was added and the aqueous phase was extracted with EtOAc. The combined organics was washed with brine, dried with MgSO4, and concentrated in vacuo. The crude mixture was purified by flash column chromatography, eluting with 5% (v/v) EtOAc:pentanes to give the desired compound (161.1 mg, 0.72 mmol, 36%).

5-(difluoromethoxy)-2-(4-propylphenyl)pyridine: Suzuki reaction was carried out to couple Sx (161.1 mg, 0.72 mmol, 1 equiv.) and (4-propylphenyl)boronic acid (177.1 mg, 1.08 mmol, 1.5 equiv.) according to General Procedure B to give the desired compound (140.0 mg, 0.53 mmol, 74%).

Example 5: 2-(difluoromethoxy)-5-(4-propylphenyl) pyridine [IIIcc (wact-55-12-9)]

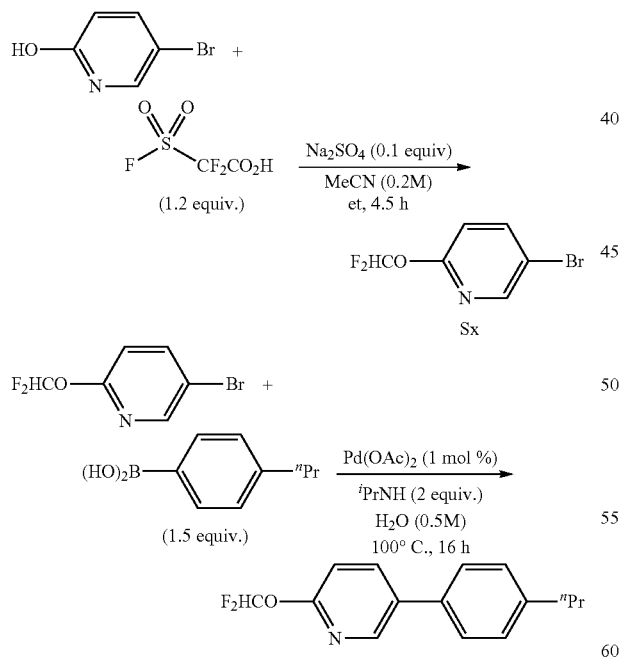

5-bromo-2-(difluoromethoxy)pyridine: The procedure was adapted from Ando et al. (1 Ando, M.; Wada, T.; Sato, N. Org. Lett. 2006, 8, 3805-3808.) 5-bromopyridin-2-ol (870 mg, 5 mmol, 1 equiv.) was dissolved in MeCN (25 mL, 0.2 M). 2,2-difluoro-2-(fluorosulfonyl)acetic acid (0.67 mL, 6 mmol, 1.2 equiv.) was added, followed by Na₂SO₄ (7.1 mg, 0.5 mmol, 0.1 equiv.). The reaction was quenched with saturated NaHCO₃(aq) solution and extracted with EtOAC. The combined organics was washed with brine, dried with MgSO4, and concentrated in vacuo. The crude mixture was purified by flash column chromatography, eluting with a 5 to 10% (v/v) EtOAc:pentanes gradient to give the desired compound (521.9 mg, 2.3 mmol, 47%).

2-(difluoromethoxy)-5-(4-propylphenyl)pyridine: Suzuki reaction was carried out to couple Sx (112.0 mg, 0.5 mmol, 1 equiv.) and (4-propylphenyl)boronic acid (123.0 mg, 0.75 mmol, 1.5 equiv.) according to General Procedure B to give the desired compound (114.0 mg, 0.433 mmol, 87%).

Example 6: 2-(4-(difluoromethoxy)phenyl)-5-ethylpyridine [IIIdd (wact-55-12-10)

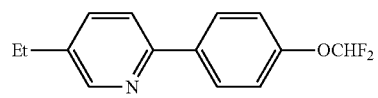

2-(4-(difluoromethoxy)phenyl)-5-ethylpyridine was synthesized according to General Procedure A, B, and C using 6-bromonicotinaldehyde, methyltriphenylphosphonium bromide, and (4-(difluoromethoxy)phenyl)boronic acid with an overall yield of 4%.

Example 7: 2-(4-(difluoromethoxy)phenyl)-5-methylpyridine [IIIee (wact-55-12-11)]

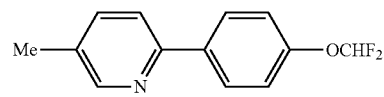

2-(4-(difluoromethoxy)phenyl)-5-methylpyridine was synthesized according to General Procedure B using 2-bromo-5-methylpyridine and (4-(difluoromethoxy)phenyl)boronic acid with a yield of 14%.

Example 8: 2-(4-(difluoromethoxy)phenyl)pyridine [IIIff (wact-55-12-12)]

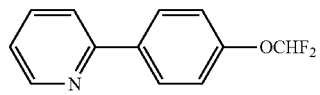 [SMILES: FC(F)Oc1ccc(-c2ccccn2)cc1]

2-(4-(difluoromethoxy)phenyl)pyridine was synthesized according to General Procedure B using 2-bromopyridine and (4-(difluoromethoxy)phenyl)boronic acid with a yield of 31%.

Example 9: 2-(4-(difluoromethoxy)phenyl)-5-(prop-1-yn-1-yl)pyridine [IIIhh (wact-55-12-14)]

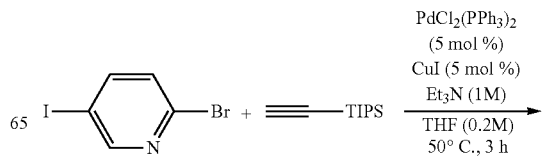

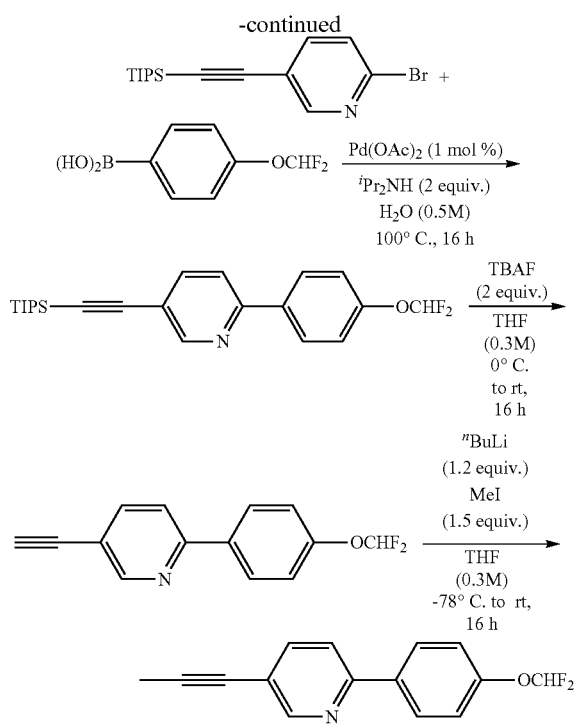

a) 2-bromo-5-((triisopropylsilyl)ethynyl)pyridine
2-bromo-5-iodopyridine (283.4 mg, 1 mmol, 1 equiv.), PdCl$_2$(PPh$_3$)$_2$ (35.1 mg, 0.05 mmol, 5 mol %), and CuI (9.5 mg, 0.05 mmol, 5 mol %) were weighed into a flame-dried round bottom flask. The contents were purged under nitrogen for 5 minutes. THF (6 mL, 0.2 M) was then added to the flask. Et$_3$N (1 mL, 1 M) and ethynyltriisopropylsilane (0.27 mL, 1.2 mmol, 1.2 equiv.) were added subsequently. The reaction was stirred at 50° C. for 3 hours. The mixture was cooled to room temperature and then filtered through celite, eluting with EtOAc. The filtrate was concentrated in vacuo and the crude mixture was purified by flash column chromatography, eluting with 10% (v/v) EtOAc:pentanes to give 2-bromo-5-((triisopropylsilyl)ethynyl)pyridine (235.6 mg, 0.70 mmol, 70%)

b) 2-(4-(difluoromethoxy)phenyl)-5-((triisopropylsilyl)ethynyl)pyridine:
Suzuki reaction was carried out to couple 2-bromo-5-((triisopropylsilyl)ethynyl)pyridine (235.6 mg, 0.70 mmol, 1 equiv.) and (4-(difluoromethoxy)phenyl)boronic acid (0.197 mg, 1.05 mmol, 1.5 equiv.) according to General Procedure B to give 2-(4-(difluoromethoxy)phenyl)-5-((triisopropylsilyl)ethynyl)pyridine (161.9 mg, 0.40 mmol, 58%).

c) 2-(4-(difluoromethoxy)phenyl)-5-ethynylpyridine:
2-(4-(difluoromethoxy)phenyl)-5-((triisopropylsilyl)ethynyl)pyridine (162.0 mg, 0.4 mmol, 1 equiv.) was dissolved in THF (1.3 mL, 0.3 M) and cooled to 0° C. TBAF (0.8 mL, 0.8 mmol, 1 M in THF, 2 equiv.) was added dropwise. The reaction was allowed to stir from 0° C. to room temperature for 16 hours. H$_2$O was added and the aqueous phase was extracted with EtOAc. The combined organics was washed with brine, dried with MgSO$_4$, and concentrated in vacuo. The crude mixture was purified by flash column chromatography, eluting with a 5 to 10% (v/v) EtOAc:pentanes gradient to give 2-(4-(difluoromethoxy)phenyl)-5-ethynylpyridine (76.5 mg, 0.31 mmol, 78%).

e) 2-(4-(difluoromethoxy)phenyl)-5-(prop-1-yn-1-yl)pyridine:

2-(4-(difluoromethoxy)phenyl)-5-ethynylpyridine (77.0 mg, 0.31 mmol, 1 equiv.) was dissolved in THF (1.0 mL, 0.3 M) and cooled to −78° C. nBuLi (0.15 mL, 0.37 mmol, 2.5 M in hexane, 1.2 equiv.) was added dropwise. The mixture was stirred at −78° C. for 1 hour. Iodomethane (0.03 mL, 0.47 mmol, 1.5 equiv.) was added dropwise. The reaction was allowed to stir from −78° C. to room temperature for 16 hours. The reaction was quenched with saturated NH$_4$Cl (aq) solution and extracted with EtOAC. The combined organics was washed with brine, dried with MgSO$_4$, and concentrated in vacuo. The crude mixture was purified by flash column chromatography, eluting with a 2.5 to 5% (v/v) EtOAc:pentanes gradient to give 2-(4-(difluoromethoxy)phenyl)-5-(prop-1-yn yl)pyridine (28.3 mg, 0.11 mmol, 35%).

Example 10: (6-(4-(difluoromethoxy)phenyl)pyridin-3-yl)methanamine [IIIkk, wact-55-12-17,]

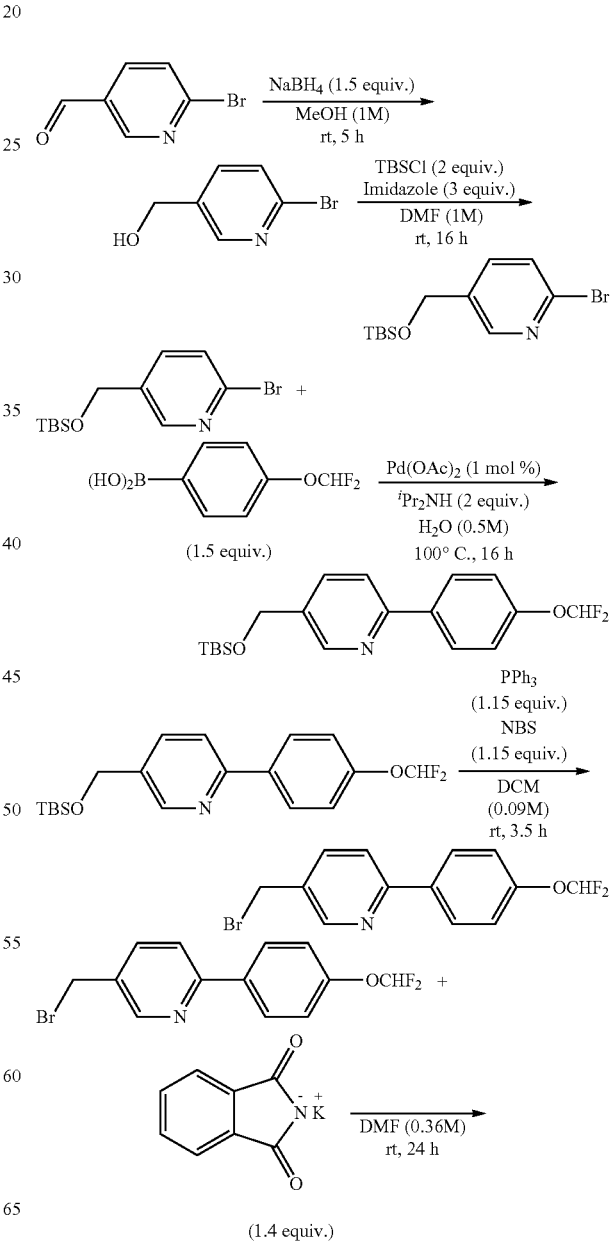

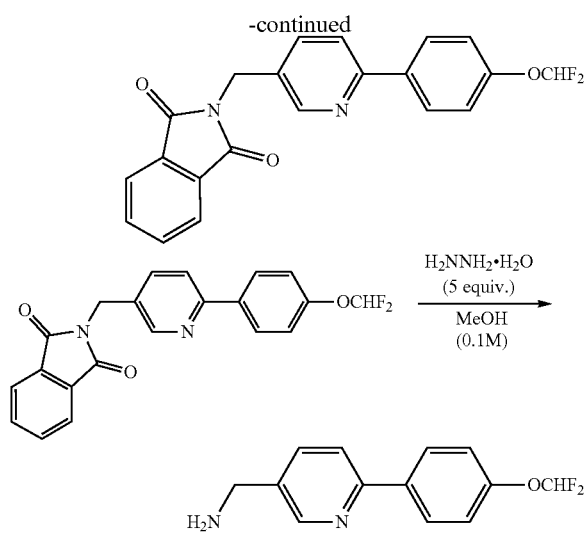

a) (6-bromopyridin-3-yl)methanol:

6-bromonicotinaldehyde (1.302 g, 7 mmol, 1 equiv.) was dissolved in MeOH (7 mL, 1 M). NaBH$_4$ (397.0 mg, 10.5 mmol, 1.5 equiv.) was added in three portions. The reaction was stirred at room temperature for 5 hours. The mixture was then cooled to 0° C. and 1 M HCl was added dropwise until bubbling seized, followed with dilution of the mixture with H$^2$O. The aqueous phase was extracted with EtOAc. The combined organics was washed with brine, dried with MgSO4, and concentrated in vacuo. The crude mixture was purified by flash column chromatography, eluting with a 50 to 60% (v/v) EtOAc:pentanes gradient to give (6-bromopyridin-3-yl)methanol (1.2859 g, 6.84 mmol, 98%).

b) 2-bromo-5-(((tert-butyldimethylsilyl)oxy)methyl)pyridine:

(6-bromopyridin-3-yl)methanol (884.0 mg, 4.7 mmol, 1 equiv.) was dissolved in DMF (4.7 mL, 1 M) and cooled to 0° C. TBSCI (1.4160 g, 9.4 mmol, 2 equiv.) was added followed by imidazole (960.0 mg, 14.1 mmol, 3 equiv.). The reaction was allowed to stir from 0° C. to room temperature for 16 hours. H$_2$O was added to the mixture and the aqueous phase was extracted with EtOAc. The combined organics was washed with brine, dried with MgSO4, and concentrated in vacuo. The crude mixture was purified by flash column chromatography, eluting with a 1 to 2% (v/v) EtOAc:pentanes gradient to give 2-bromo-5-(((tert-butyldimethylsilyl)oxy)methyl)pyridine (1.0952 g, 3.63 mmol, 77%).

c) 5-(((tert-butyldimethylsilyl)oxy)methyl)-2-(4-(difluoromethoxy)phenyl)pyridine:

Suzuki reaction was carried out to couple 2-bromo-5-(((tert-butyldimethylsilyl)oxy)methyl)pyridine (1.0900 g, 3.63 mmol, 1 equiv.) and (4-(difluoromethoxy)phenyl)boronic acid (1.0200 g, 5.45 mmol, 1.5 equiv.) according to General Procedure B to give 5-(((tert-butyldimethylsilyl)oxy)methyl)-2-(4-(difluoromethoxy)phenyl)pyridine (751.6 mg, 1.98 mmol, 54%).

d) (6-(4-(difluoromethoxy)phenyl)pyridin-3-yl)methanol:

5-(((tert-butyldimethylsilyl)oxy)methyl)-2-(4-(difluoromethoxy)phenyl)pyridine (751.6 mg, 1.98 mmol, 1 equiv.) was dissolved in THF (6.6 mL, 0.3 M) and cooled to 0° C. TBAF (2.38 mL, 2.38 mmol, 1 M in THF, 1.2 equiv.) was added dropwise. The reaction was allowed to stir from 0° C. to room temperature for 16 hours. H$_2$O was added to the mixture and the aqueous phase was extracted with EtOAc. The combined organics was washed with brine, dried with MgSO$_4$, and concentrated in vacuo. The crude mixture was purified by flash column chromatography, eluting with a 50 to 60% (v/v) EtOAc:pentanes gradient to give (6-(4-(difluoromethoxy)phenyl)pyridin-3-yl)methanol (363.0 mg, 1.45 mmol, 73%).

e) 5-(bromomethyl)-2-(4-(difluoromethoxy)phenyl)pyridine:

(6-(4-(difluoromethoxy)phenyl)pyridin-3-yl)methanol (363.0 mg, 1.45 mmol, 1 equiv.) was dissolved in dichloromethane (DCM) (16.11 mL, 0.09 M). PPh$_3$ (438.0 mg, 1.67 mmol, 1.15 equiv.) followed by NBS (297.2 mg, 1.67 mmol, 1.15 equiv.) were added.

The reaction was stirred at room temperature for 3.5 hours. H$_2$O was added to the mixture and the aqueous phase was extracted with EtOAc. The combined organics was washed with brine, dried with MgSO4, and concentrated in vacuo. The crude mixture was purified by flash column chromatography, eluting with a 15% (v/v) EtOAc:pentanes to give 5-(bromomethyl)-2-(4-(difluoromethoxy)phenyl)pyridine (349.5 mg, 1.11 mmol, 77%).

f) 2-((6-(4-(difluoromethoxy)phenyl)pyridin-3-yl)methyl)isoindoline-1,3-dione:

5-(bromomethyl)-2-(4-(difluoromethoxy)phenyl)pyridine (349.5 mg, 1.11 mmol, 1 equiv.) was dissolved in DMF (3.1 mL, 0.36 M). Phthalimide potassium salt (438.0 mg, 1.67 mmol, 1.15 equiv.) was added. The reaction was stirred at room temperature for 24 hours. H$_2$O was added to the mixture and the aqueous phase was extracted with EtOAc. The combined organics was washed with brine, dried with MgSO$_4$, and concentrated in vacuo. The crude mixture was purified by flash column chromatography, eluting with a 20 to 25% (v/v) EtOAc:pentanes gradient to give 2-((6-(4-(difluoromethoxy)phenyl)pyridin-3-yl)methyl)isoindoline-1,3-dione (262.2 mg, 0.69 mmol, 62%).

g) (6-(4-(difluoromethoxy)phenyl)pyridin-3-yl)methanamine:

2-((6-(4-(difluoromethoxy)phenyl)pyridin-3-yl)methyl)isoindoline-1,3-dione (262.2 mg, 0.69 mmol, 1 equiv.) was dissolved in MeOH (6.9 mL, 0.1 M). Hydrazine hydrate (0.26 mL, 3.56 mmol, 50-60%, 5 equiv.) was added. The reaction was refluxed at 70° C. for 4 hours. The mixture was cooled to room temperature and filtered through Celite, eluting with MeOH. The filtrate was concentrated in vacuo. H$_2$O (7 mL) was added, followed by 1 M KOH (1.75 mL). The aqueous phase was extracted with DCM. The combined organics was dried with MgSO$_4$ and then concentrated in vacuo to give (6-(4-(difluoromethoxy)phenyl)pyridin-3-yl)methanamine (131.4 mg, 0.53 mmol, 76%).

Example 11: 2-(4-(difluoromethoxy)phenyl)-6-propylpyridine [IIInn (wact-55-12-20)]

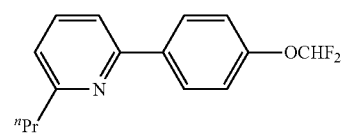

2-(4-(difluoromethoxy)phenyl)-6-propylpyridine was synthesized according to General Procedure A, B, and C using 6-bromopicolinaldehyde, ethyltriphenylphosphonium bromide, and (4-(difluoromethoxy)phenyl)boronic acid with an overall yield of 18%.

Example 12: 2-(4-(difluoromethoxy)phenyl)-4-propylpyridine [IIIoo (wact-55-12-21)]

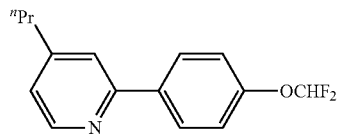

2-(4-(difluoromethoxy)phenyl)-4-propylpyridine was synthesized according to General Procedure A, B, and C using 2-bromoisonicotinaldehyde, ethyltriphenylphosphonium bromide, and (4-(difluoromethoxy)phenyl)boronic acid with an overall yield of 9%.

Example 13: 2-(4-(difluoromethoxy)phenyl)-3-propylpyridine [IIIpp (wact-55-12-22)]

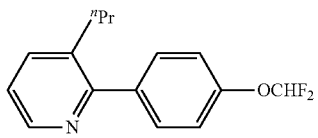

2-(4-(difluoromethoxy)phenyl)-3-propylpyridine was synthesized according to General Procedure A, B, and C using 2-bromonicotinaldehyde, ethyltriphenylphosphonium bromide, and (4-(difluoromethoxy)phenyl)boronic acid with an overall yield of 6%.

Example 14: 2-(3-(difluoromethoxy)phenyl)-5-propylpyridine [IIIqq (wact-55-12-23)]

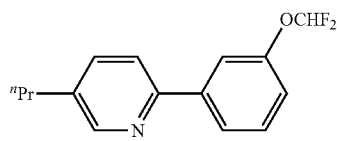

2-(3-(difluoromethoxy)phenyl)-5-propylpyridine was synthesized according to General Procedure A, B, and C using 6-bromonicotinaldehyde, ethyltriphenylphosphonium bromide, and (3-(difluoromethoxy)phenyl)boronic acid with an overall yield of 21%.

Example 15: 2-(4-(difluoromethoxy)phenyl)-5-propylpyrimidine [IIIss (wact-55-12-25)]

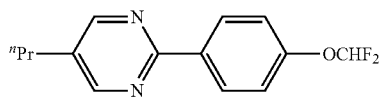

Pd(OAc)$_2$ (3.4 mg, 0.015 mmol, 5 mol %), PPh$_3$ (7.9 mg, 0.03 mmol, 10 mol %), K2CO3 (124.4 mg, 0.9 mmol, 3 equiv.) and (4-(difluoromethoxy)phenyl)boronic acid (84.6 mg, 0.45 mmol, 1.5 equiv.) were added to a flamed-dried flask. The mixture was purged with nitrogen for 5 minutes. Dioxane (0.55 mL, 0.55 M) and H$_2$O (0.14 mL, 2.18 M) were added, followed by 2-chloro-5-propylpyrimidine (0.04 mL, 0.3 mmol, 1 equiv.). The reaction was then refluxed at 100° C. for 16 hours. H$_2$O was added to the mixture and the aqueous phase was extracted with EtOAc. The combined organics was washed with brine, dried with MgSO$_4$, and concentrated in vacuo. The crude mixture was purified by flash column chromatography, eluting with a 2.5 to 5% (v/v) EtOAc:pentanes gradient to give 2-(4-(difluoromethoxy)phenyl)-5-propylpyrimidine (68.5 mg, 0.26 mmol, 86%).

Example 16: 2-(4-(difluoromethoxy)phenyl)-5-isobutylpyridine [IIItt (wact-55-12-26)]

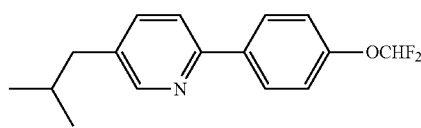 [SMILES: CC(C)Cc1ccc(-c2ccc(OC(F)F)cc2)nc1]

2-(4-(difluoromethoxy)phenyl)-5-isobutylpyridine was synthesized according to General Procedure A, B, and C using 6-bromonicotinaldehyde, isopropyltriphenylphosphonium iodide, and (4-(difluoromethoxy)phenyl)boronic acid with an overall yield of 23%.

Example 17: 5-butyl-2-(4-(difluoromethoxy)phenyl)pyridine [IIIuu (wact-55-12-27)]

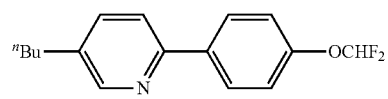

5-butyl-2-(4-(difluoromethoxy)phenyl)pyridine was synthesized according to General Procedure A, B, and C using 6-bromonicotinaldehyde, propyltriphenylphosphonium bromide, and (4-(difluoromethoxy)phenyl)boronic acid with an overall yield of 32%.

Example 18: 5-butyl-2-(4-methoxyphenyl)pyridine [IIIvv (wact-55-12-28)]

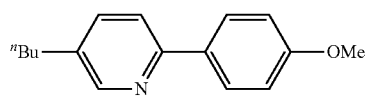

5-butyl-2-(4-methoxyphenyl)pyridine was synthesized according to General Procedure A, B, and C using 6-bromonicotinaldehyde, ethyltriphenylphosphonium bromide, and (4-methoxyphenyl)boronic acid with an overall yield of 41%.

Example 19: 4-(5-butylpyridin-2-yl)phenol [IIIww (wact-55-12-29)]

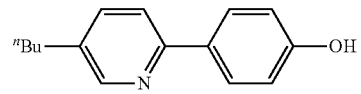

4-(5-butylpyridin-2-yl)phenol was synthesized according to General Procedure A, B, and C using 6-bromonicotinaldehyde, ethyltriphenylphosphonium bromide and (4-(benzyloxy)phenyl)boronic acid with an overall yield of 31%.

Biological Studies

Example 20: Screening of Compounds

Because of their dependence on a host, parasitic nematodes are difficult to culture, maintain and sustain. Therefore, to screen for antithelmintic compounds, the non-parasitic nematode, *C. elegans*, was used as a model system, then compound leads were investigated in parasitic nematodes.

Molecules that can modulate the egg-laying rate of the *C. elegans* (which can be done in medium-throughput fashion) were identified first and then the hits' ability to disrupt worm locomotion was examined using lower-throughput techniques. Egg-laying is a convenient system with which to interrogate neuromuscular control because it's digital output (an egg is either laid or not) can be easily quantified. Wild type hermaphrodites carry 10-15 eggs in their uterus and lay ~one egg per hour in the liquid (control) buffer used for liquid worm culture. Egg-laying is principally regulated by cholinergic and serotonergic signaling via conserved receptors.

To identify egg-laying (Egl) modulators, a medium-throughput line-scanning microscope capable of imaging a 96 well plate in just over 2 minutes was used. From the resulting images, image analysis software to count the number of eggs laid per adult per hour in each well was used. Small molecules at a final concentration of 60 µM were screened, which is a technically convenient concentration where most molecules stay in solution. This may be considered a high concentration for most screening platforms, but is suitable for *C. elegans* because of the nematode's robust xenobiotic defenses.

A collection of 486 synthetic small molecules that have previously shown some effect on worm growth was screened. These molecules are from Chembridge Inc., are drug-like in their physico-chemical properties, and have relatively uncharacterized bioactivity. To identify Egl-stimulators, small molecules were screened in a benign control buffer. To identify Egl-inhibitors, molecules were screened in the background of 2.5 mM serotonin plus 7.7 mM nicotine, which is a cocktail that was empirically determined to induce robust egg-laying in liquid media. Molecules that reproducibly ($p<0.05$) modulate egg-laying two fold greater than control conditions were considered 'stimulators', and molecules that modulate egg-laying two fold less than stimulating conditions were considered 'inhibitors'.

In the above-described assay, 31 stimulators and 33 inhibitors of egg-laying were identified. A structural comparison of these hits using a Tanimoto™/FP2 similarity cutoff of 0.55 or greater revealed that many of the Egl-modulators belong to structurally-similar families. A network was generated using a Tanimoto™ chemical similarity cut-off of 55%. Molecules that share structural similarity typically modulate egg laying similarly, suggesting a shared mechanism of action.

The ability of the 64 Egl hits to modulate the normal sinusoidal locomotion of wild type *C. elegans* was then examined. The animal's behaviour over the course of several hours was manually monitored while the animal moved atop a solid agar substrate containing the small molecule. Many different genes govern the sinusoidal locomotion of wild type *C. elegans*, but their mutation can lead to qualitatively distinct locomotory phenotypes. Hence, a distinct locomotory response to a small molecule can be suggestive of its mechanism of action.

Figure 1:
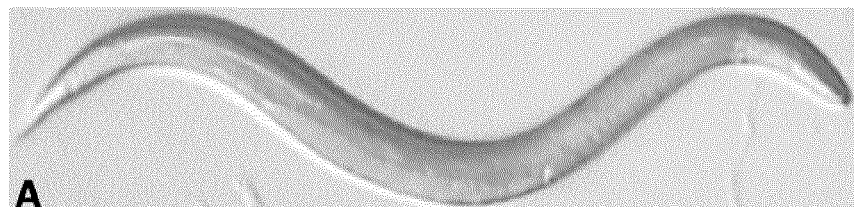
Figure 1:
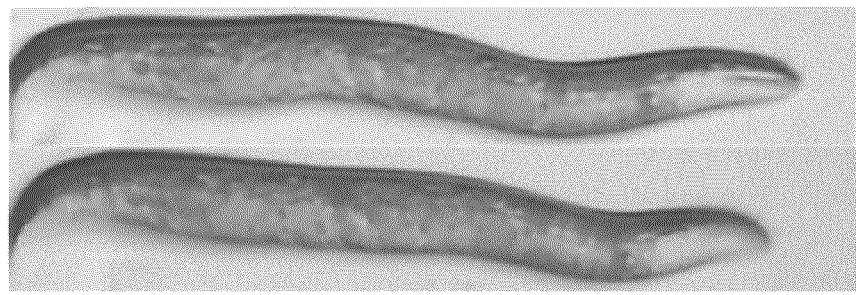

Compared to the normal phenotype of the worm as shown in FIG. 1 panel A, 8 molecules that induce simultaneous anterior and posterior contraction (called a 'rubber-band' phenotype) were identified; 3 molecules that cause animals to turn along their circumferential axis (ca a 'shaker' phenotype) were identified; 3 molecules that cause the animal to coil like a snake (called a 'coiler' phenotype) were identified; 2 molecules that induce jerky uncoordination (called jerky-unc) were identified; 3 molecules that disrupt reverse locomotion were identified; and 3 that induce paralysis were identified.

Figure 2:
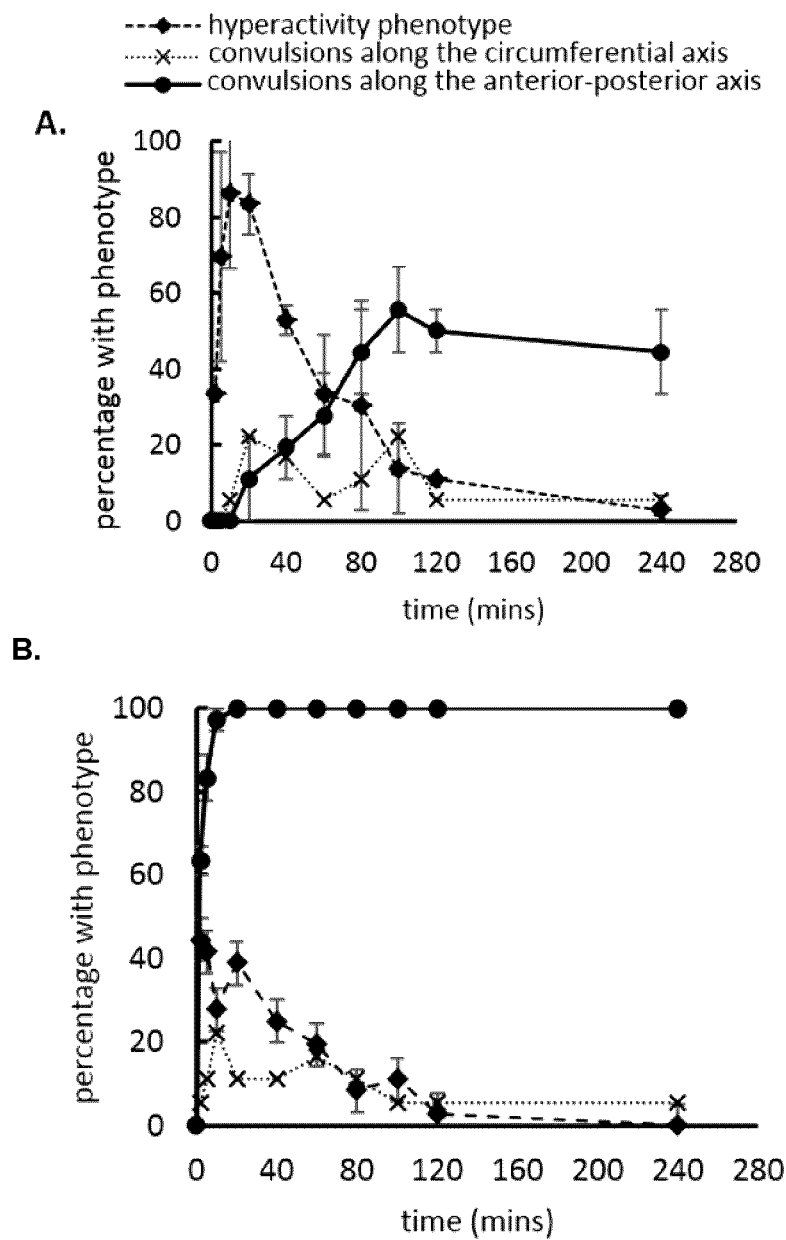

Wact-55 (exemplary compound IIIa) induced a rubber-band phenotype where the body shows an anterior-posterior convulsion leading to a shortening of the body, as shown in FIG. 1 panel B (0.5 second time-lapse). Previous phylogenetic bioactivity analysis suggests that the activity of wact-55 (Compound IIIa) might be restricted to nematodes. The rubber-band phenotype that is induced by wact-55 (compound IIIa) is consistent with the agonism of a nicotinic acetylcholine receptor (nAChR). Wact-55 also induces several motor behaviours, including initial rapid movement followed by convulsions and paralysis (FIG. 2). By six hours, dead animals are evident.

Adult wild type worms were picked onto solid agar containing various concentrations of the respective wact-55 analogs. Worms are scored for the indicated phenotype (see legend); convulsions along the circumferential axis is characterized as the 'shaker' phenotype in *C. elegans*; convulsions along the anterior-posterior axis is characterized as the 'rubber-band' phenotype in *C. elegans*. 18 young-adult animals were scored at each time-point for rubber-band (animals spontaneously contract or do so upon touch on the nose with a platinum wire), hyperactive movement (observing rapid lateral nose movement) and shaker (spontaneous circumferential rotations). Phenotypes were not mutually exclusive (i.e. animals could demonstrate all phenotypes). Data are showing the mean number of animals with each phenotype.

Example 21: Cytotoxicity of Exemplary Compound IIIa

Figure 3:
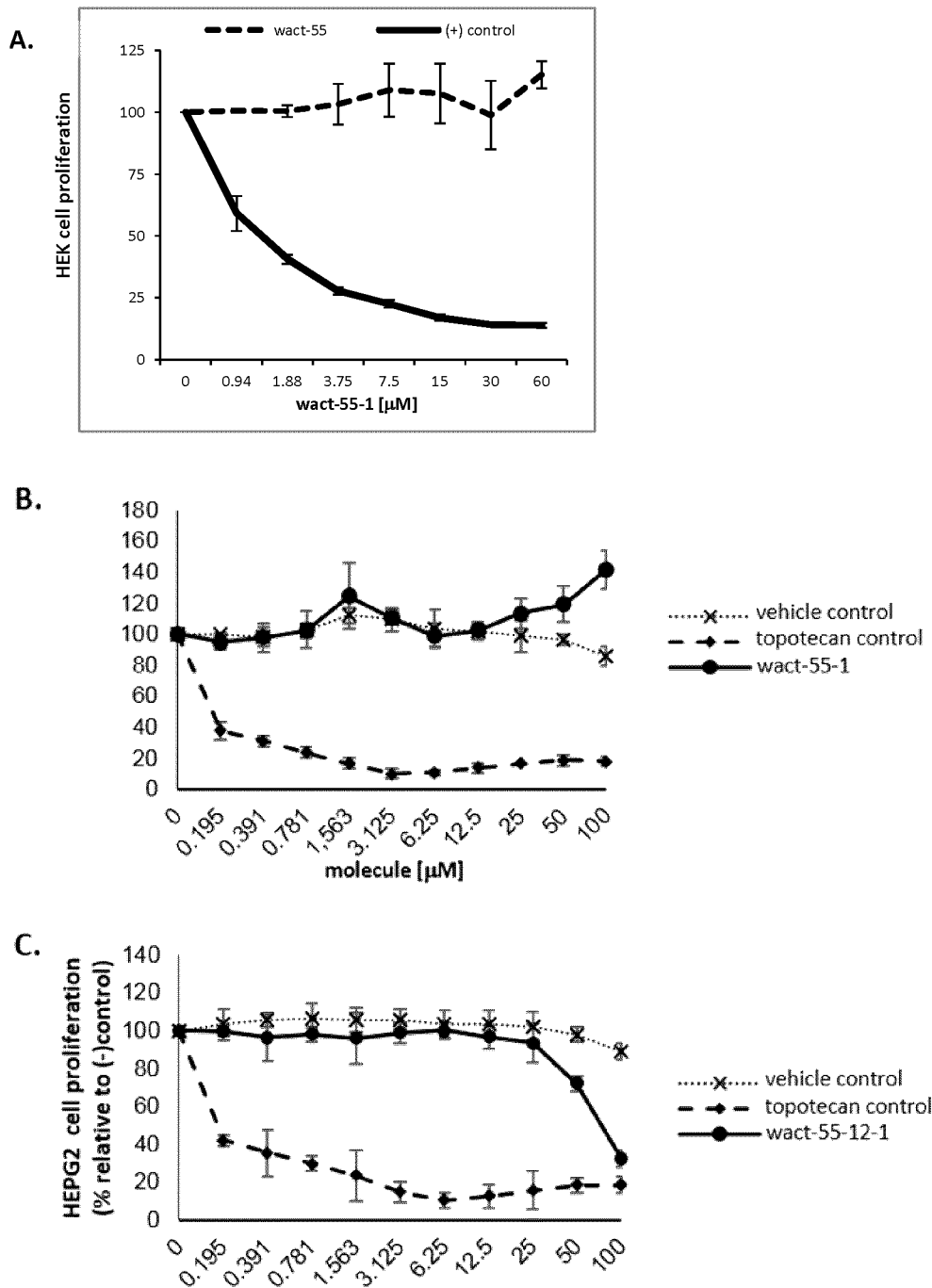

The cytotoxicity of exemplary compound IIIa was investigated by measuring human-derived HEPG2 or human-derived HEK293 cell proliferation in a dose-response analysis and no effect was found on HEPG2 or HEK293 cell proliferation by exemplary compound II la (Wact-55-1) or IIIi (Wact-55-12-1) as shown in FIG. 3. A cytotoxic formulation was used as positive control. Experiments were performed in triplicates on different days. Cell viability was assess using a standard Celltiter Blue™ Cell Viability Assay (Promega). Compounds were added to cells in 96-well plates at time zero and cell viability assessed in 48 hours. Error bars indicate standard deviation.

Figure 4:
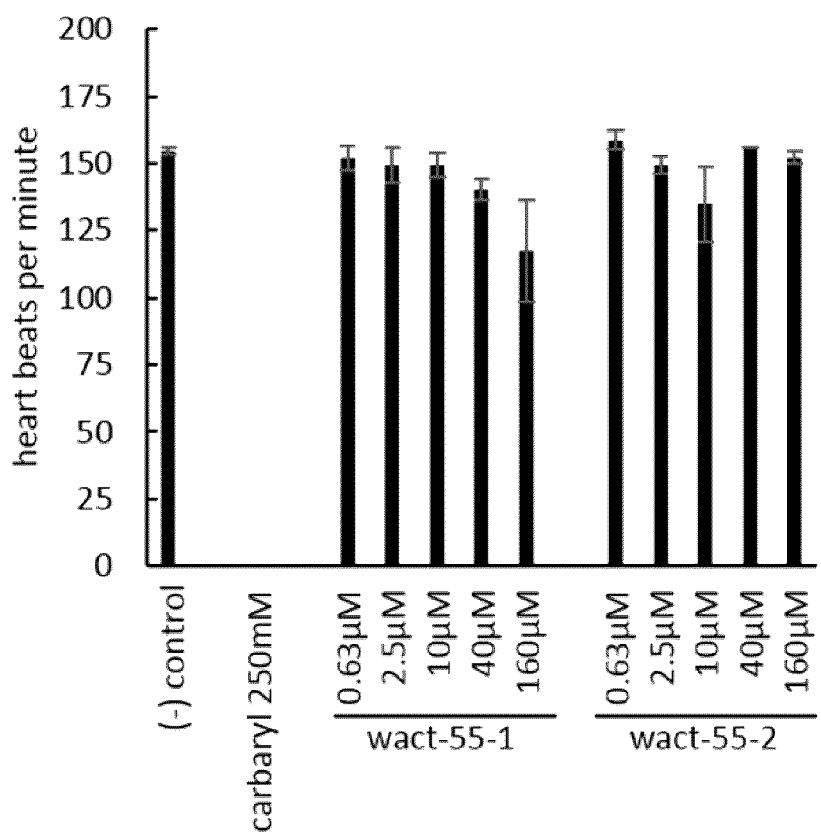

The ability of exemplary compound IIIa (wact-55-1) to disrupt the embryonic and larval development of zebrafish (*D. rerio*) was also investigated and little-to-no effects at the highest concentrations tested was found (160 µM) (FIG. 4). Zebrafish provide a highly sensitive platform to investigate whether bioactive molecules disrupt vertebrate development. These data show that exemplary compound IIIa (wact-55-1) is a promising and potentially safe anthelmintic lead molecule.

Example 22: Mechanism of Exemplary Compound IIIa as Ach Signaling Agonist (a) *C. elegans* cannot be easily Mutated to Resist compound IIIa:

Exemplary compound IIIa (wact-55) is part of the worm active library because it kills (LD100) *C. elegans* at concentrations of 7.5 μM or less. The standard procedure used for an antihelmintic bioactive small molecule of interest is to perform a genetic screen with randomly mutagenized *C. elegans* to isolate resistant mutants. Mutant genes that confer resistance often encode the target or the targeted pathway of a bioactive molecule. 190,000 first generation ($F_1$) and 200,000 second generation ($F_2$) animals from randomly mutagenized parents/grandparents were screened for those that could survive the lethal effects of compound IIIc. No IIIc-resistant mutants resulted. While this campaign did not reveal exemplary compound IIIa (wact-55)'s mechanism of action, the failure to generate resistance suggests that nematodes in the wild will have difficulty evolving resistance to the lethal effects of exemplary compound IIIa (wact-55).

(b) Exemplary Compound IIIa Phylogenetic Bioactive Profile:

Whether exemplary compound IIIa might be effective against parasitic nematodes was explored. It was shown that exemplary compound IIIa kills nematode parasites of cows and sheep (*C. oncophora, H. Contortis*, respectively) in ex-vivo assays. Inhibition of ES pore secretion of natural products is a key mechanism by which anthelmintics clear gastric parasitic nematodes. These data show that exemplary compound IIIa can incapacitate a variety of parasitic worm species.

Figure 5:
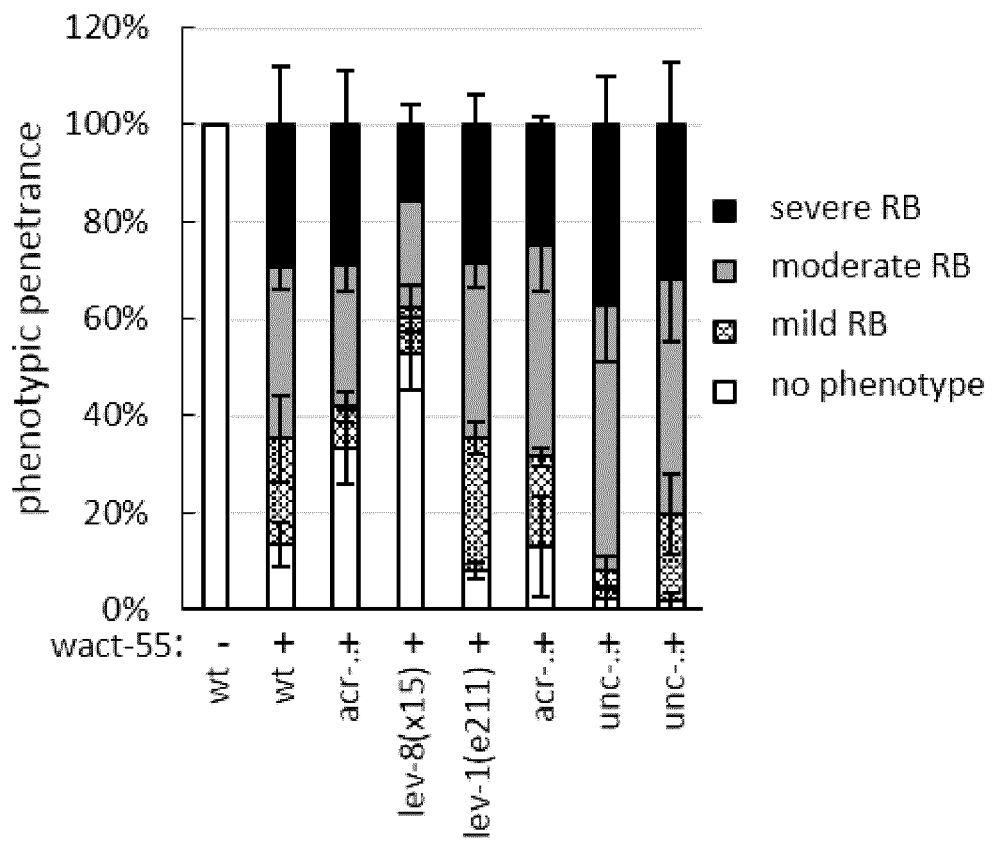
FIG. 5 shows the percentage of worms showing mutated nAChR (indicated on the X axis) to resist the rubber-band phenotype induced by exemplary compound IIIa (wact-55). RB means rubber-band phenotype.

(c) Exemplary Compound IIIa modulates the nervous system:

The rubber-band phenotype of exemplary compound IIIa is similar to a number of gain-of-function mutants in a small number of genes, including that of the non-alpha nicotinic acetylcholine receptor (nAChR) subunit ACR-2. The ability of a small set of nAChR subunit loss-of-function mutants to suppress the locomotory phenotype that is induced by exemplary compound IIIa was surveyed. It was found that loss-of-function in ACR-2 and LEV-8, but not other nAChR subunits, can partially suppress the rubber-band phenotype induced by exemplary compound IIIa (FIG. 5). This partial resistance is not inconsistent with the inability to isolate mutants that resist the lethality of exemplary compound IIIa; the deletion of multiple receptor subtypes may be needed to confer resistance to exemplary compound IIIa's lethal effects. Regardless, the chemical-genetic results are consistent with exemplary compound IIIa agonizing nAChRs.

Figure 6:
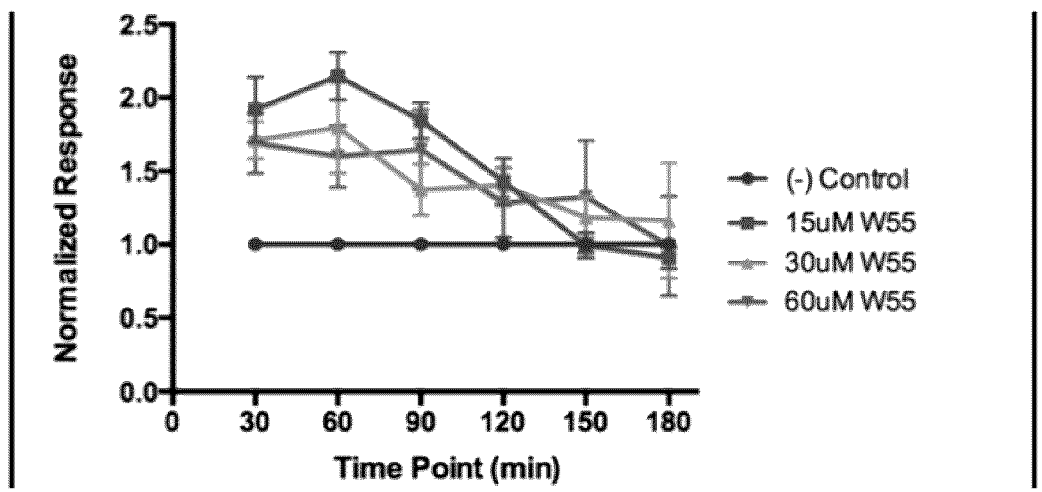
FIG. 6 shows Microtracker analysis data, demonstrating exemplary compound IIIa's (wact-55 or W55) suppression of unc-17(e2475) paralysis.

The idea that exemplary compound IIIa is a nAChR agonist was tested in two additional ways. First, whether exemplary compound IIIa phenotypically interacts with aldicarb was examined. Aldicarb inhibits ACh esterase, which catabolizes ACh at the synapse. Aldicarb treatment therefore increases ACh abundance at the synaptic cleft, and in turn, induces paralysis. If exemplary compound IIIa agonizes nAChRs, then aldicarb should enhance the effects of exemplary compound IIIa and that is what was observed ($p<0.001$). Second, whether exemplary compound IIIa can suppress some of the movement defects that are induced by a genetic deficiency in ACh signaling was tested. The unc-17(e245) mutant is deficient in loading synaptic vesicles with ACh and are consequently severely uncoordinated. It was found that exemplary compound IIIa is able to rescue some of the movement defects of unc-17(e245) mutants ($p<0.001$). This is shown in FIG. 6, where Microtracker analysis using Microtracker™ (Phylum Biotech) shows detect wact-55 (compounds IIIa)'s ability to suppress the movement defects of the unc-17 mutant. Microtracker analysis measures worm movement via the interruption of infrared light beams in 96 well plate format. Together, this data supports the idea that exemplary compound IIIa agonizes nAChRs.

Example 22 Preliminary Structural Activity Relationship (SAR) and Bioactivity of Exemplary Compounds of Formula (III)

In an effort to increase exemplary compound IIIa's potency and understand the substructural elements that are important for its bioactivity, a preliminary structure-activity relationship (SAR) analysis was conducted (Table 1). Seven commercially available analogs of exemplary compound IIIa were tested for their ability to induce locomotory defects in *C. elegans*. Exemplary compound IIIb, was found to be approximately two fold more potent than wact-55-1 (Table 1).

In Table 1, Activity indicates percentage of animals that exhibit the rubber-band phenotype at 60 μM of the indicated compound after crawling for 80 minutes on solid substrate. If a penetrant phenotype is observed, a dose-response analysis is performed; the $EC_{50}$ is shown.

TABLE 1

Preliminary SAR of exemplary compounds of Formula (III)

| Compound | $R^3$ | $R^4$ | Activity | $EC_{50}$ (μM) |
|---|---|---|---|---|
| IIIa (wact 55-1) | $(CH_2)_4CH_3$ | $OCH_3$ | 74.6 +/− 3.2 | 29.8 |
| IIIb (wact 55-2) | $(CH_2)_4CH_3$ | $OCHF_2$ | 83.3 +/− 5.6 | 15.4 |
| IIIc (wact 55-3) | $(CH_2)_6CH_3$ | OH | 0 +/− 0 | — |
| IIId (wact 55-4-1) | $(CH_2)_7CH_3$ | OH | 0 +/− 0 | >60 |
| IIIe (wact 55-5) | $(CH_2)_4CH_3$ | CH=CH—CN | 16.7 +/− 11.1 | 26.0 |
| IIIf (wact 55-6) | $(CH_2)_6CH_3$ | $O(CH_2)_5CH_3$ | 0 +/− 0 | — |
| IIIg (wact 55-7) | $(CH_2)_4CH_3$ | $CH=CHC(O)NH_2$ | 0 +/− 0 | — |
| IIIh (wact 55-8) | $(CH_2)_4CH_3$ | $OCH_2CH_3$ | 2.8 +/− 2.8 | — |
| IIIi (wact 55-12-1) | $(CH_2)_2CH_3$ | $OCHF_2$ | 100 +/− 0 | 5.5 |
| IIIj (wact 55-10) | $(CH_2)_6CH_3$ | $OCH_3$ | 5.6 +/− 5.6 | >60 |
| IIIk (wact 55-11) | $(CH_2)_5CH_3$ | $OCH_3$ | 0 +/− 0 | — |
| IIIl | $CH_3$ | $OCH_3$ | TBD | |
| IIIn (wact 55-13) | $(CH_2)_6CH_3$ | $OCHF_2$ | 1.9 +/− 1.9 | >60 |
| IIIo (wact 55-14) | $(CH_2)_4CH_3$ | I | 9.3 +/− 4.9 | >60 |
| IIIp (wact 55-15) | $(CH_2)_4CH_3$ | Br | 18.5 +/− 13.4 | >60 |

TBD = to be determined

Example 23: Exemplary Compound IIIa (wact-55) kills *C. elegans* via a Potentially Novel Mechanism Relative to Commercial Nematicides Existing anthelmintics and nematicides do not induces rubber-band type of convulsions. Regardless, whether the mechanism by which the exemplary compound IIIa (wact-55) scaffold kills *C. elegans* is the same as the mechanism by which characterized nematicides and anthelmintics kill *C. elegans* was tested. A collection of nine *C. elegans* mutant strains that are each resistant to each of nine different classes of nematicides/anthelmintics (FIG. 7) was assembled. These nine strains resisted were not able to resist wact-55 (FIG. 7). This suggests that exemplary compound IIIa (wact-55) has a distinct mechanism of action from the nine different classes of nematicides/anthelmintics that the respective mutants resist.

Example 24: Exemplary Compound IIIa (wact-55-1) Induces Motor Defects by Enhancing Dense Core Vesicle Release The hyperactive locomotion and increased egg-laying rate induced by exemplary compound IIIa (wact-55) are phenotypes shared with mutants that increase diacylglycerol (DAG) production. DAG is a key second messenger produced in response to G-protein (Gq) activation. Gq is called EGL-30 in worms. Activation of EGL-30/Gq stimulates EGL-8, a phospholipase C ortholog, to convert PIP2 lipids into DAG. DAG activates protein kinase C (PKC-1), which in turn, promotes the fusion of dense core vesicles (DCVs) to the plasma membrane and the release of DCV contents into the synaptic cleft (simply referred to here as DCV release') (FIG. 8). DCVs modulate the post-synaptic cell via their bioamine and neuropeptide contents.

Whether exemplary compound IIIa (wact-55) treatment increases DAG production by using a strain of worms that expresses GFP in response to DAG was investigated. Exemplary compound IIIa (wact-55-1) was found to increase GFP expression >50-fold in this strain (p<0.001), suggesting that wact-55 may lead to increased DAG production (FIG. 9)

Whether PMA (phorbol myristate acetate, a cell-permeable DAG mimetic) can induce rubber-band (RB) convulsions like wact-55 was tested. Concentrations of PMA that are 4-fold higher than the minimum concentration that induces robust GFP expression in the DAG reporter strain fail to induced a RB phenotype. This suggests that DAG-production alone cannot account for exemplary compound IIIa (wact-55) activity.

Given the relationship between exemplary compound IIIa (wact-55-1), DAG, and DCVs, whether the exemplary compound IIIa (wact-55-1)-induced phenotype is modulated when components that regulate DCV release are disrupted by mutation was tested. Exemplary compound IIIa (wact-55-1) was found to interact with all mutants tested in a manner consistent with exemplary compound IIIa (wact-55-1)'s modulation of the DAG-DCV pathway (FIGS. 8 and 10). For example, a hypomorphic mutant of egl-30 reduces DAG production and also partially suppresses exemplary compound IIIa (wact-55-1) activity (FIG. 10). A hypomorphic mutant of goa-1 increases DAG production and also enhances exemplary compound IIIa (wact-55-1) activity (FIG. 10).

Exemplary compound IIIa (Wact-55-1) interactions with mutants of CaMKII (calcium/calmodulin-dependent protein kinase II) are of particular note. Wild-type CaMKII (called UNC-43 in worms) negatively regulates DCV release (FIG. 8). Strong reduction-of-function (RF) mutations of unc-43 elicit a rubber-band phenotype and are the only mutants among regulators of DCV release to do so. Also, unc-43(RF) mutants have an egg-laying constitutive phenotype, just like exemplary compound IIIa (wact-55-1). Gain-of-function (GF) alleles of unc-43 are nearly paralyzed. unc-43 (RF) mutants were found to dramatically enhance the wact-55-1 RB phenotype, while the unc-43 (GF) mutant suppresses the wact-55-1 RB phenotype (FIG. 10). Furthermore, exemplary compound IIIa (wact-55-1) can rescue the immobility of UNC-43 (GF) mutants in a dose-dependent manner (not shown). Together, these data suggest that exemplary compound IIIa (wact-55-1) may inhibit the activity of UNC-43/CaMKII or a component that acts close to UNC-43/CaMKII (FIG. 8).

Given that unc-43 (RF) mutants lead to increased DCV release, whether wact-55 treatment also leads to increased DCV release was tested. A strain of worms that expresses a Venus-fused neuropeptide in neurons was used. NLP-21:: Venus is packaged into DCVs of motor neurons and has been a useful marker of DCVs. Similar to unc-43 (RF) mutants, exemplary compound IIIa (wact-55)-treated worms have dramatically fewer intense Venus-puncta than controls (p<0.001) (FIG. 11). This data further supports the model that exemplary compound IIIa (wact-55) generates convulsions via excess DCV release.

Example 25: Exemplary Compound IIIa (wact-55-1) Kills Parasitic Nematodes

The ability of exemplary compound IIIa (wact-55-1) analogs to kill both free-living and parasitic nematode species was tested (Table 2). Exemplary compound IIIa (wact-55) analogs were tested against free-living nematodes (*C. elegans* and *Pristionchus pacificus*), several parasites of animals (*Phasmarhabditis hermaphrodita*, a parasite of slugs; *Haemonchus contortus*, a parasite of ruminants; *Cooperia oncophora*, another parasite of ruminants; *Necator americanis*, a hookworm nematode that parasitizes humans; *Trichuris muris*, a whipworm nematode that parasitizes mice and is highly related to human whipworm; *Strongyloides ratti*, an intestinal nematode parasite of rodents that is highly related to human *Strongyloides*) and nematode parasites of plants, including *Meloidogyne incognita* and *Meloidogyne chitwoodi*. Many exemplary compound IIIa (wact-55-1) analogs were able to kill the parasitic nematodes of animals and that two of the exemplary compound IIIa (wact-55-1) analogs tested killed the parasitic nematodes of plants Table 2. Together, these data indicate the utility of the compounds of the application to kill parasitic nematodes of animals and plants.

TABLE 2

| | free-living | | | | | parasites of animals | | |
| --- | --- | --- | --- | --- | --- | --- | --- | --- |
| Compound I.D. | C. elegans acute motor phene [a] | C. elegans (L1 viability) [b] | C. elegans (dauer viability) [c] | C. elegans (adult viability) [c] | P. pacificus (L1 viability) [c] | P. hermaphrodita (L1 viability) [d] | C. onchophora (egg viability) [e] | H. contortus (egg viability) [e] |
| IIIa (wact-55-1) | 60 | 7.5 | 60 | 60 | 7.5 | 3.8 | 7.5 | 7.5 |
| IIIb (wact-55-2) | 30 | 15 | 30 | np | 7.5 | 3.8 | | |
| IIIc (wact-55-3) | np | 15 | np | 30 | 15 | 7.5 | | |
| IIId (wact-55-4-1) | np | 15 | np | np | 15 | 7.5 | | |
| IIIt (wact-55-4-2) | | | | | | | | |
| IIIe (wact-55-5) | np | 3.8 | np | 60 | 1.9 | 7.5 | | |
| IIIf (wact-55-6) | np | np | np | np | np | 3.8 | | |
| III (wact-55-7) | np | np | np | np | np | np | | |
| IIIh (wact-55-8) | np | 7.5 | 30 | np | 3.8 | 3.8 | | |
| IIIu (wact-55-9) | np | np | 60 | np | 60 | 60 | | |

TABLE 2-continued

| Compound I.D. | | | | | | |
|---|---|---|---|---|---|---|
| IIIj (wact-55-10) | np | np | np | np | np | np |
| IIIk (wact-55-11) | np | 30 | np | np | 3.8 | 3.8 |
| IIIi (wact-55-12-1) | 15 | 60 | np | np | 30 | 30 |
| IIIy (wact-55-12-2) | | | | | | |
| IIIw (wact-55-12-3) | | | | | | |
| IIIx (wact-55-12-4) | | | | | | |
| IIIy (wact-55-12-5) | 30 | 30 | | | | |
| IIIz (wact-55-12-6) | 60 | 30 | 60 | np | | 7.5 |
| IIIaa (wact-55-12-7) | 15 | 30 | | | | |
| IIIbb (wact-55-12-8) | 15 | 60 | | | | |
| IIIcc (wact-55-12-9) | 60 | 60 | | | | |
| IIIdd (wact-55-12-10) | 15 | 30 | 30 | np | 15 | 15 |
| IIIee (wact-55-12-11) | 60 | 60 | | | | |
| IIIff (wact-55-12-12) | 60 | np | np | np | 60 | 60 |
| IIIgg (wact-55-12-13) | | | | | | |
| IIIhh (wact-55-12-14) | 15 | 7.5 | | | | |
| IIIii (wact-55-12-15) | | | | | | |
| IIIjj (wact-55-12-16) | | | | | | |
| IIIkk (wact-55-12-17) | np | np | | | | |
| IIIll (wact-55-12-18) | | | | | | |
| IIImm (wact-55-12-19) | | | | | | |
| IIInn (wact-55-12-20) | np | np | np | np | 30 | 60 |
| IIIoo (wact-55-12-21) | 60 | 60 | np | np | 30 | 30 |
| IIIpp (wact-55-12-22) | np | np | np | np | np | 60 |
| IIIqq (wact-55-12-23) | 60 | 60 | np | np | 30 | 15 |
| IIIrr (wact-55-12-24) | | | | | | |
| IIIss (wact-55-12-25) | | | | | | |
| IIItt (wact-55-12-26) | 60 | 30 | | | | |
| IIIuu (wact-55-12-27) | 30 | 15 | | | | |
| IIIvv (wact-55-12-28) | 60 | 15 | | | | |
| IIIww (wact-55-12-29) | | | | | | |
| IIIn (wact-55-13) | np | np | np | np | np | 7.5 |
| IIIo (wact-55-14) | np | np | np | np | 15 | 15 |
| IIIp (wact-55-15) | np | np | np | np | 7.5 | 7.5 |
| IIIq (wact-55-16) | np | 30 | | | | |
| IIIr (wact-55-17) | np | 7.5 | | | | |
| IIIs (wact-55-18) | np | 7.5 | | | | |

| | parasites of animals | | | plant parasites | | | | |
|---|---|---|---|---|---|---|---|---|
| Compound I.D. | *Necator americanis* (L3 viability) [f] | *Trichuris muris* (adult viability) [g] | *Strongyloides r.* (adult viability) [h] | *M. incognita* (J2 viability in vitro) [i] | *M. chitwoodi* (J2 viability in vitro) [i] | *M. incognita* (Quick Soil Test) [j] | *M. incognita* (Egg Hatch Rate) [k] | *M. incognita* (Hatching Mobility) [k] |
| IIIa (wact-55-1) | np | 25 | 25 | 45 | 45 | 45 | 45 | 45 |
| IIIb (wact-55-2) | 10 | 25 | 25 | np | | 45 | np | 45 |
| IIIc (wact-55-3) | 10 | 25 | 25 | 45 | | 45 | 45 | 45 |
| IIId (wact-55-4-1) | 10 | 25 | 25 | 45 | | np | 45 | 45 |
| IIIt (wact-55-4-2) | | | | | | | | |
| IIIe (wact-55-5) | 10 | 25 | 25 | np | | 45 | np | 45 |
| IIIf (wact-55-6) | 10 | 25 | 25 | | | | | |
| III (wact-55-7) | 10 | 25 | 25 | | | | | |
| IIIh (wact-55-8) | 10 | 25 | 25 | np | | 45 | 45 | 45 |
| IIIu (wact-55-9) | 10 | 25 | 25 | | | | | |
| IIIj (wact-55-10) | 10 | 25 | 25 | | | | | |
| IIIk (wact-55-11) | 10 | 25 | 25 | np | | 45 | np | 45 |
| IIIi (wact-55-12-1) | np | 25 | 25 | 45 | 45 | 45 | 45 | 45 |
| IIIy (wact-55-12-2) | | | | | | | | |
| IIIw (wact-55-12-3) | | | | | | | | |
| IIIx (wact-55-12-4) | | | | | | | | |
| IIIy (wact-55-12-5) | | | | np | | 45 | 45 | 45 |
| IIIz (wact-55-12-6) | | | | np | | 45 | np | 45 |
| IIIaa (wact-55-12-7) | | | | 45 | | 45 | 45 | 45 |
| IIIbb (wact-55-12-8) | | | | np | | 45 | 45 | 45 |
| IIIcc (wact-55-12-9) | | | | np | | 45 | np | 45 |
| IIIdd (wact-55-12-10) | | | | | | | | |
| IIIee (wact-55-12-11) | | | | np | | 45 | 45 | 45 |
| IIIff (wact-55-12-12) | | | | 45 | | 45 | 45 | 45 |
| IIIgg (wact-55-12-13) | | | | | | | | |
| IIIhh (wact-55-12-14) | | | | np | | 45 | 45 | 45 |
| IIIii (wact-55-12-15) | | | | 45 | | | | |
| IIIjj (wact-55-12-16) | | | | | | | | |
| IIIkk (wact-55-12-17) | | | | np | | 45 | np | np |
| IIIll (wact-55-12-18) | | | | | | | | |
| IIImm (wact-55-12-19) | | | | | | | | |
| IIInn (wact-55-12-20) | | | | | | | | |
| IIIoo (wact-55-12-21) | | | | np | | 45 | np | 45 |
| IIIpp (wact-55-12-22) | | | | | | | | |
| IIIqq (wact-55-12-23) | | | | np | | 45 | np | np |

TABLE 2-continued

| | | | | | | | |
|---|---|---|---|---|---|---|---|
| IIIrr (wact-55-12-24) | | | | | | | |
| IIIss (wact-55-12-25) | | | | np | 45 | 45 | 45 |
| IIItt (wact-55-12-26) | | | | np | 45 | 45 | np |
| IIIuu (wact-55-12-27) | | | | np | 45 | np | 45 |
| IIIw (wact-55-12-28) | | | | 45 | 45 | 45 | 45 |
| IIIww (wact-55-12-29) | | | | | | | |
| IIIn (wact-55-13) | np | 25 | 25 | 45 | 45 | np | 45 |
| IIIo (wact-55-14) | 10 | 25 | 25 | np | np | np | 45 |
| IIIp (wact-55-15) | 10 | 25 | 25 | np | 45 | np | 45 |
| IIIq (wact-55-16) | | | | 45 | 45 | 45 | 45 |
| IIIr (wact-55-17) | | | | 45 | 45 | 45 | 45 |
| IIIs (wact-55-18) | | | | 45 | 45 | 45 | 45 |

[a] *C. elegans* acute motor phenotype: In compounds 55-12-6, 55-12-9, 55-12-12, 55-12-21 and 55-12-23 the concentration at which 10-50% of the animals exhibit convulsion/paralysis phenotypes) is reported. In other compounds, the lowest concentration at which 50% of the young adult animals exhibit convulsion/paralysis phenotypes is reported. Assays were performed by placing young adult animals on solid substrate and behaviour was quantified after 80 minutes of incubation.
[b] *C. elegans* viability assay was conducted with a three day protocol. In compounds 55-11, 55-12-21 and 55-12-23 the lowest concentration tested in which at greater than 20% of animals (relative to no-drug controls) were dead after 72 hours is reported. In other compounds-the lowest concentration tested in which at least 80% of animals (relative to no-drug controls) were dead after 72 hours in the compound is reported.
[c] Notation is the same as bullet point "b" above. Specifically, all compounds show the lowest concentration tested in which at least 80% of animals (relative to no-drug controls) were dead after 72 hours, with the the following exception: *C. elegans* (dauer viability)-compounds 55-2, 55-8, 55-9 and 55-12-6 show the concentration where 10-20% death is exhibited relative to no-drug controls and *P. pacificus* compound 55-12-20 indicates the lowest concentration tested in which at greater than 20% of animals (relative to no-drug controls) were dead after 72 hours.
[d] *Phasmarhabditis hermaphrodita* is a nematode parasite of slugs; Same annotation as bullet point "b" above. All compounds show the lowest concentration tested in which at least 80% of animals (relative to no-drug controls) were dead after 72 hours with the exception of compounds 55-6, 55-12-20 and 55-12-22, which show the lowest concentration tested in which at greater than 20% of animals (relative to no-drug controls) were dead after 72 hours.
[e] *Cooperia oncophora* and *Haemonchus contortus* are nematode parasites of ruminants; Same annotation as bullet point "b" above. Compounds show the lowest concentration tested in which at least 80% of animals (relative to no-drug controls) were dead after 72 hours.
[f] *Necator americanis* is a human hookworm nematode parasite; assay was done using 10 uM of the compound; compounds 55-2, 55-3, 55-4-1, 55-5, 55-8, 55-10, 55-11, 55-14 and 55-15->80% death; other compounds->20% and <80% death. All analyses done after a 72 hour incubation.
[g] *Trichuris muris* is a whipworm nematode parasite of mice that is highly related to human whipworm; assay was done using 25 uM of the compound; compounds 55-6, 55-7 and 55-14->80% death; other compounds->20% and <80% death. All analyses done after a 72 hour incubation.
[h] *Strongyloides ratti* is an intestinal nematode parasite of rodents that is highly related to human Strongyloides; assay was done using 25 uM of the compound; compounds 55-2, 55-3, 55-5, 55-8, 55-10, 55-11, 55-12-1, 55-13 and 55-14->80% death; other compounds->20% and <80% death. All analyses done after a 72 hour incubation.
[i] *Meloidogyne incognita* and *Meloidogyne chitwoodi* are plant parasitic nematodes; the in vitro assay was done using 45 uM of the compound; compounds 55-1, 55-3, 55-12-1, 55-12-7, 55-16 and 55-18->80% death; other compounds->20% and <80% death. All analyses done after either 48 or 72 hours of incubation.
[j] *Meloidogyne incognita* Quick Soil test: 45 uM of each compound, ~2000 J2a per plant; technical duplicate (H2O quadruplicate); number of J2s counted in 1 mL of blended root tissue; worms and drug are in the soil for 24 hours before planting the tomatoe. After planting they are left for 3 more days. So worms are in soil for 4 days total. Compounds 55-3, 55-5, 55-12-12, 55-12-21, 55-12-28, 55-13 and 55-17->80% killing; compounds 55-8, 55-12-1, 55-12-5, 55-12-7, 55-12-8, 55-12-9, 55-12-11, 55-12-14, 55-12-17, 55-12-25, 55-12-27, 55-12-28, 55-15, 55-16 and 55-18->20% and <80% killing, other compounds-10-20% killing.
[k] *Meloidogyne incognita* egg-hatch assay: ~50 eggs plated per well; average of 3 technical replicates; 45 uM of each compound, General Protocols for Biological Studies
a) *C. elegans* Strains and Culture Methods All the animals were cultured using standard methods at 20° C. (Brenner, 1974), except for the temperature-sensitive MJ69 [emb-8(hc69)ts] strain, which was initially cultivated at 15° C., before being shifted to 25° C. for the final two days. The N2 (wild-type) strain of *Caenorhabditis elegans* was obtained from the *C. elegans* Genetic Center (University of Minnesota). Mutant strains were also obtained from the *C. elegans* Genetic Center. The unc-17(md414), unc-17 (e327) and unc-17(e795) strains were provided by J. Rand from the University of Oklahoma.

b) *C. elegans* Motor Phenotype Analyses: Screen of the 64 Egg-Laying Modifiers for Locomotory Defects Locomotor phenotype analyses were done in 24-well plates with 1 mL of MYOB substrate (Burns et al., 2006) seeded with 25 µL of OP50 *Escherichia coli* on each well. Each compound was added to the MYOB substrate before pouring to achieve desired concentration after diffusion through the media. The final concentration of dimethyl sulfoxide (DMSO) in each of the wells was 1° A v/v. Young adult or fourth-staged larval worms are transferred into each well using a platinum wire pick. A dissection microscope (Leica MZ 125) was used to visualize the movement of worms on the solid substrate.

Using wild-type worms, the locomotory defects induced by each compound were analyzed after 30, 60, 120, and 240 min of exposure to 30 µM and 60 µM concentrations. The specific locomotor phenotype was noted, and a qualitative assessment of the severity was made based on the degree of locomotor incapacitation and penetrance of the phenotype. 'Severe' indicates a strong perturbation and high penetrance, 'moderate' indicates a strong phenotype with low penetrance or a weak phenotype that is highly penetrant, and 'mild' indicates a weak phenotype that has low penetrance. The 'shrinker' phenotype describes animals that contract and shorten longitudinally. 'Shaker' describes a phenotype where animals rotate on their longitudinal axis. The toiler' phenotype describes worms that assume a tightly wound posture. 'Jerky-unc' animals are unable to make smooth motions, and often exhibit abrupt stops and starts. 'Reversal-defective' animals fail to back normally when prodded on the nose. Paralysis was distinguished from death by the presence of pharyngeal pumping. The chemical-genetic interaction analyses of the wact-45 family of compounds where done using a total of 18 worms that were scored as exhibiting either 'no phenotype', 'jerky-Um', 'coiled', or 'paralyzed'.

c) *C. elegans* Motor Phenotype Analyses: Analyses of wact-55-Induced Locomotory Defects ~25 young adult animals of each indicated strain were picked using a platinum wire onto 2% MYOB agar containing the indicated drug condition with 1% DMSO. Animals were incubated for 80 minutes and scored for rubber-band phenotype; animals that appeared rigidly paralyzed (unable to generate a sinusoidal waveform) demonstrating spontaneous shortening of the body along the longitudinal axis or upon a gentle touch on the nose were scored as 'rubber-band'. 18 animals were scored per trial; data are the mean response of 2-3 replicates showing the standard error of the mean.

d) Analysis of Dense Core Vesicle Release in *C. elegans*

Young adult KG2430 animals expressing the CelS56 transgene were incubated on 2% MYOB agar in 24-well plates containing the indicated drug condition with 1% DMSO for 4 hours. After incubation, animals were fixed on microscope slides with a 50 uL 1% agar pad with 5 uL of 100 mM tetramisole in H2O. Animals were imaged using a Leica DMI 6000B microscope with a KSU confocal scanner unit equipped with an Applied Scientific Instrumentation MS-2000 microcontroller. A 6 µM Z-stack with 0.2 µM step (30 slices) was captured in GFP (400 ms exposure), RFP (600 ms exposure) and DIC channels (50 ms exposure) imaging each individual channel's Z-stack before moving to the next channel; 561 nm (green) and 491 nm (red) excitation lasers were used (Gen 5.0 Cobalt lasers). Dorsal DA6/DB6 axons were imaged and maximal projections of the GFP channel were generated; axonal segments were manually cropped by hand and the mean pixel intensity of the GFP channel along the axonal segment was calculated. Boxplots were generated using R (RStudio) using the ggplot2 data visualization package with an overlying stripchart showing each calculated mean pixel intensity value. 16 animals for each condition were captured over 3 separate imaging sessions per each drug treatment; images were captured no later than 30 minutes after fixing.

e) HEK293 Cell Proliferation Assay

HEK293 cells were seeded into 96 well plates, at 5000 cells per well, in 100 mL total volumes of DMEM/10% FBS/1% PS media and grown overnight at 37° C. in the presence of 5% CO2. Compounds (0.5 mL volumes from appropriate source plates) were then added to cells, and growth was continued for an additional 48 hours. Following growth, 10 mL of CellTiter-Blue Viability reagent (Promega) was added to each well, and plates were incubated for an additional 4 hours at 37° C. in the presence of 5% CO2. Fluorescence measurements (560 nm excitation/590 nm emission) were then performed using a CLARIOstar Plate Reader (BMG Labtech) to quantify reagent reduction and estimate cell viability.

f) HEPG2 Cell Proliferation Assay

Hep G2 cells were counted using a haemocytometer, diluted, and seeded in 384-well plates to a final density of $5 \times 10^4$ cells/mL in 100 uL of RPMI-1640 medium supplemented with 10% heat inactivated fetal bovine serum (Gibco) and 1.2× Antibiotic-Antimycotic (Gibco). Cells were incubated at 37° C. with 5% $CO_2$ for 24 hours. Subsequently, a 2-fold dilution series of test compound was added to cells at a final volume of 200 uL and incubated at 37° C. with 5% $CO_2$ for 72 hours. After 72 hours, Alamar Blue (Invitrogen) was added to the Hep G2 cells at a final concentration of 0.5× and plates were incubated at 37° C. for 4 hours. Fluorescence was measured at Ex560 nm/Em590 nm and corrected for background from the medium. All assays were performed in technical triplicates and in at least two biological replicates.

g) Small Molecule Assays with Zebrafish

The analysis of vertebrate bioactivity was carried out in the zebrafish (Danio rerio) at 4 days post-fertilization (4 dpf). Zebrafish were maintained and handled under the guidance and approval of the Canadian Council on Animal Care and the Hospital for Sick Children Laboratory Animal Services. Three wild-type (TLAB) embryos were analyzed in each well of a 24-well plate containing 1 mL of E3 medium (5 mM NaCl, 0.17 mM KCl, 0.33 mM CaCl2, 0.33 mM MgSO4). Drug compounds were added to each well to reach final concentrations of 160 μM, 40 μM, 10 μM, 2.5 μM and 0.625 μM (0.5% v/v DMSO), as well as a DMSO control well. The fish were examined for phenotypes after 30 minutes (single drug) or 10 minutes (combined drugs) of drug exposure using a Zeiss standard dissection microscope. Heart rate, tail and trunk circulation, pooling of blood, and movement were recorded. Atrial and ventricular heartbeats were counted separately for a time of 15 seconds. A fish was marked with a 'no heartbeat' phenotype after two consecutive 15 second-periods of no heartbeats. A 'no movement' phenotype was assigned when there was no movement even after physical stimulation with forceps. Biological replicates were performed for each compound at each concentration and condition.

h) Small Molecule Analyses with the Animal Parasites C. oncophora and H. contortus Fresh cattle and sheep faeces containing eggs of an ivermectin-resistant strain of C. onchophora and the MHco3 (ISE) strain of H. contortus respectively, were kindly supplied by Dr Doug Colwell and Dawn Gray (Lethbridge Research Station, Agriculture and Agri-Food Canada). Experimental infections used to generate this material were carried out using established methods and were approved by the Lethbridge AAFC Animal Care committee and conducted under animal use license ACC1407. Cattle faeces containing C. onchophora eggs were stored anaerobically at 4 C for a maximum of 3 weeks, whereas sheep faeces containing H. contortus eggs were stored at 20C for no more than 48 h before harvesting eggs for use. Eggs were isolated from faeces using a standard saturated salt flotation method immediately before each egg hatch assay. Approximately 100 eggs suspended in 100 ml of water were added to each well of a 96-well plate, and the wactive library chemicals were screened at two different concentrations (7.5 and 60 μM, 0.6% DMSO v/v). Baseline egg hatch rates were determined in DMSO control wells ~48 h after the initial set-up of the assay by the addition of iodine tincture to stop development. Plates having DMSO control wells with hatch rates >70% were assayed on a semiquantitative gradient of '−' to '+++', where '−' wells had a hatch rate of <10%, and '+++' wells had a hatch rate close to wild type (usually >80%). A dissection microscope was used for visualization purposes. Chemicals were considered bioactive if they consistently had a '−' in more than one trial, with 'very very strong' assigned to compounds that were 90-100% lethal at 7.5 μM in all replicates, 'very strong' if the same was true at 60 μM, 'strong' if replicates had a hatch rate between 10 and 50%, 'medium' if replicates had a 50-80% hatch rate and 'weak' if only one replicate was between 50 and 80% hatch rate. A molecule was considered 'lethal' if it exhibited 'very very strong' or 'very strong' bioactivity.

The invention claimed is:

1. A method of treating or preventing a nematode infection comprising administering an effective amount of a compound of Formula (III):

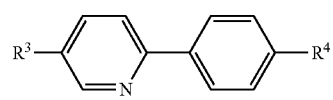

(III)

and/or a pharmaceutically acceptable salt and/or solvate thereof to a subject in need thereof, wherein:
$R^3$ is $C_{1-10}$alkyl; and
$R^4$ is OH, halo, $OC_{1-10}$fluoroalkyl or $OC_{1-10}$alkyl, the group being unsubstituted or substituted with CN or $C(O)NH_2$.

2. The method of claim 1, wherein the compound of Formula (III) is selected from

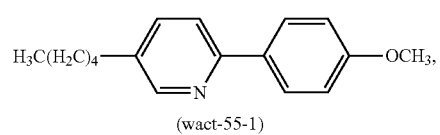

IIIa (wact-55-1)

(wact-55-2) IIIb: H₃C(H₂C)₄-pyridine-C₆H₄-OCHF₂, (wact-55-3) IIIc: H₃C(H₂C)₆-pyridine-C₆H₄-OH, (wact-55-4-1) IIId: H₃C(H₂C)₇-pyridine-C₆H₄-OH, (wact-55-8) IIIh: H₃C(H₂C)₄-pyridine-C₆H₄-OCH₂CH₃, (wact-55-12-1) IIIi: H₃C(H₂C)₂-pyridine-C₆H₄-OCHF₂, (wact-55-10) IIIj: H₃C(H₂C)₆-pyridine-C₆H₄-OCH₃, (wact-55-11) IIIk: H₃C(H₂C)₅-pyridine-C₆H₄-OCH₃, (wact-55) IIIl: H₃C-pyridine-C₆H₄-OCH₃, (wact-55-13) IIIn: H₃C(H₂C)₆-pyridine-C₆H₄-OCHF₂, (wact-55-14) IIIo: H₃C(H₂C)₄-pyridine-C₆H₄-I, (wact-55-15) IIIp: H₃C(H₂C)₄-pyridine-C₆H₄-Br, (wact-55-9) IIIu: H₃C(H₂C)₂-pyridine-C₆H₄-OCF₃, (wact-55-12-2) IIIv: H₃C(H₂C)₂-pyridine-C₆H₄-OCH₂Cl, (wact-12-3) IIIw: H₃C(H₂C)₂-pyridine-C₆H₄-OCHFCl, (wact-55-12-4) IIIx: H₃C(H₂C)₂-pyridine-C₆H₄-OCHCl₂, (wact-55-12-10) IIIdd: H₃CH₂C-pyridine-C₆H₄-OCHF₂, (wact-55-12-11) IIIee: H₃C-pyridine-C₆H₄-OCHF₂, (wact-55-12-26) IIItt: (H₃C)₂HC(H₂C)-pyridine-C₆H₄-OCHF₂, (wact-55-12-27) IIIuu: H₃C(H₂C)₃-pyridine-C₆H₄-OCHF₂, (wact-55-12-28) IIIvv: H₃C(H₂C)₃-pyridine-C₆H₄-OCH₃, and (wact-55-12-29) IIIww: H₃C(H₂C)₃-pyridine-C₆H₄-OH, or a pharmaceutically acceptable salt and/or solvate thereof.

3. The method of claim 1, wherein the nematode infection is an infection of a nematode of a species selected from *Cooperia oncophora, Haemonchus contortus, Caenorhabditis elegans, Pristionchus pacificus, Phasmarhabditis hermaphrodita, Necator americanis, Trichuris muris, Strongyloides ratti, Meloidogyne incognita* and *Meloidogyne chitwoodi*.

4. The method of claim 1, wherein $R^3$ is $C_{1-8}$alkyl.

5. The method of claim 1, wherein $R^4$ is OH, OCH₃, or OCHF₂.

6. The method of claim 1, wherein the subject is selected from a plant, a seed and soil.

7. A method of treating or preventing a nematode infection comprising administering an effective amount of a composition comprising a pharmaceutically acceptable carrier and a compound of Formula (III), and/or a pharmaceutically acceptable salt and/or solvate thereof, as defined in claim 1, to a subject in need thereof.

8. The method of claim 7, wherein the subject is selected from a plant, a seed and soil.

9. The method of claim 8, comprising administering the composition through one or more means selected from pre-planting, post-planting, as a feed additive, a drench, an external application, a pill and by injection.

10. The method of claim 7, wherein the compound of Formula (III) is selected from:

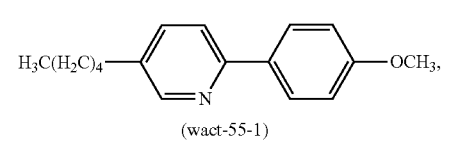
(wact-55-1)
IIIa

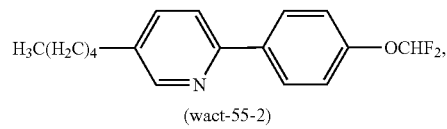
(wact-55-2)
IIIb

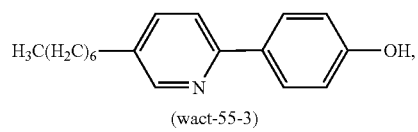
(wact-55-3)
IIIc

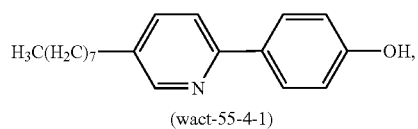
(wact-55-4-1)
IIId

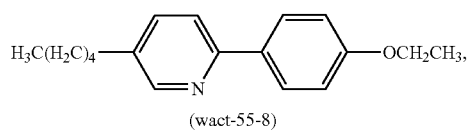
(wact-55-8)
IIIh

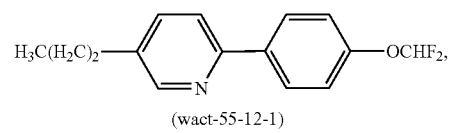
(wact-55-12-1)
IIIi

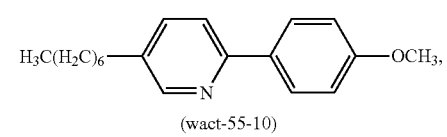
(wact-55-10)
IIIj

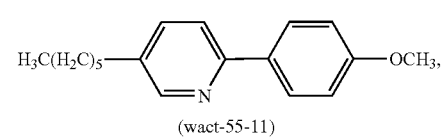
(wact-55-11)
IIIk

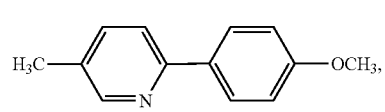
(wact-55-12)?
IIIl

-continued

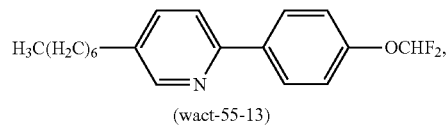
(wact-55-13)
IIIn

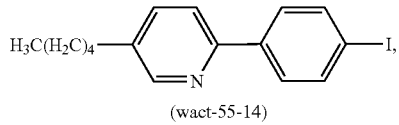
(wact-55-14)
IIIo

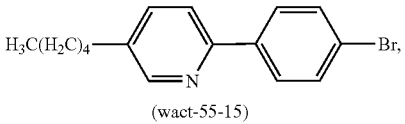
(wact-55-15)
IIIp

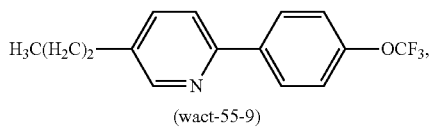
(wact-55-9)
IIIu

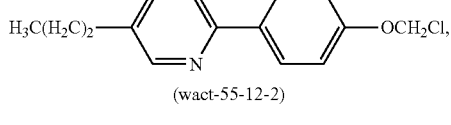
(wact-55-12-2)
IIIv

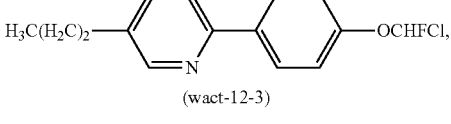
(wact-12-3)
IIIw

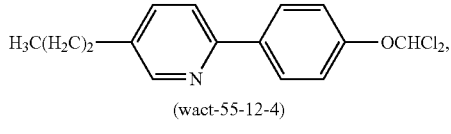
(wact-55-12-4)
IIIx

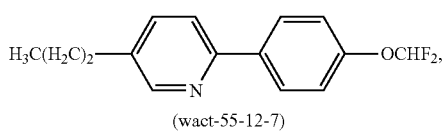
(wact-55-12-7)
IIIaa

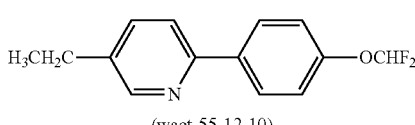
(wact-55-12-10)
IIIdd

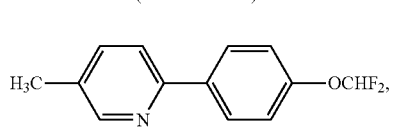
(wact-55-12-11)
IIIee

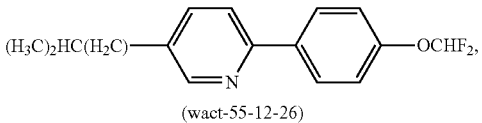
(wact-55-12-26)
IIItt

-continued

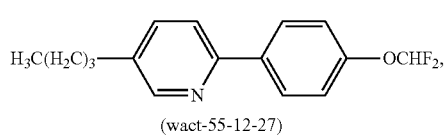
(wact-55-12-27) IIIuu

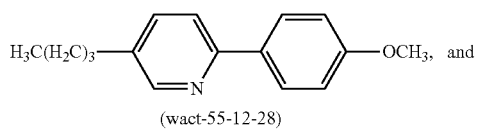
(wact-55-12-28) IIIvv, and

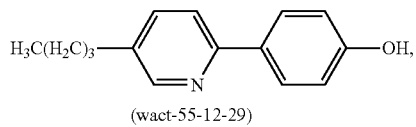
(wact-55-12-29) IIIww or a pharmaceutically acceptable salt and/or solvate thereof.

11. The method of claim 7, wherein the nematode infection is an infection of a nematode of a species selected from *Cooperia oncophora, Haemonchus contortus, Caenorhabditis elegans, Pristionchus pacificus, Phasmarhabditis hermaphrodita, Necator americanis, Trichuris muris, Strongyloides ratti, Meloidogyne incognita* and *Meloidogyne chitwoodi*.

12. The method of claim 7, wherein $R^3$ is $C_{1-8}$alkyl.

13. The method of claim 7, wherein $R^4$ is OH, $OCH_3$, or $OCHF_2$.

* * * * *